(12) United States Patent
Wagner et al.

(10) Patent No.: US 10,238,655 B2
(45) Date of Patent: *Mar. 26, 2019

(54) DIHYDROINDENE AND TETRAHYDRONAPHTHALENE COMPOUNDS

(71) Applicant: ARIZONA BOARD OF REGENTS ON BEHALF OF ARIZONA STATE UNIVERSITY, Scottsdale, AZ (US)

(72) Inventors: Carl E. Wagner, Glendale, AZ (US); Pamela A. Marshall, Peoria, AZ (US); Peter W. Jurutka, Scottsdale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/878,297

(22) Filed: Jan. 23, 2018

(65) Prior Publication Data

US 2018/0207156 A1    Jul. 26, 2018

Related U.S. Application Data

(60) Provisional application No. 62/449,501, filed on Jan. 23, 2017.

(51) Int. Cl.
| | | |
|---|---|---|
| A61K 31/10 | (2006.01) | |
| A61P 25/28 | (2006.01) | |
| A61P 35/00 | (2006.01) | |
| A61K 31/136 | (2006.01) | |
| A61K 31/192 | (2006.01) | |
| A61K 31/196 | (2006.01) | |
| A61K 31/505 | (2006.01) | |

(52) U.S. Cl.
CPC ............ A61K 31/505 (2013.01); A61K 31/10 (2013.01); A61K 31/136 (2013.01); A61K 31/192 (2013.01); A61K 31/196 (2013.01); A61P 25/28 (2018.01); A61P 35/00 (2018.01)

(58) Field of Classification Search
CPC ......... A61P 25/28; A61P 35/00; C07D 311/74
USPC ........................................................ 514/249
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,762,844 A | 8/1988 | Grohe et al. |
| 4,820,508 A | 4/1989 | Wortzman |
| 4,826,984 A | 5/1989 | Berlin et al. |
| 4,938,949 A | 7/1990 | Borch et al. |
| 4,980,509 A | 12/1990 | Maignan |
| 4,992,478 A | 2/1991 | Geria |
| 5,006,550 A | 4/1991 | Chandraratna |
| 5,414,156 A | 5/1995 | Cho et al. |
| 5,587,367 A | 12/1996 | Reuchert |
| 5,672,710 A | 9/1997 | Beard et al. |
| 5,780,676 A | 7/1998 | Boehm et al. |
| 5,962,731 A | 10/1999 | Boehm et al. |
| 5,981,776 A | 11/1999 | Diaz et al. |
| 6,137,002 A | 10/2000 | Fisher |
| 6,162,815 A | 12/2000 | Bernardon |
| 6,172,112 B1 | 1/2001 | Brouillette et al. |
| 6,258,775 B1 | 7/2001 | Bernardon et al. |
| 6,291,677 B1 | 9/2001 | Vasudevan |
| 6,303,785 B1 | 10/2001 | Vasudevan |
| 6,313,107 B1 | 11/2001 | Vasudevan |
| 6,545,049 B1 | 4/2003 | Canan-Koch et al. |
| 6,586,460 B1 * | 7/2003 | Berlin .................. C07D 311/58 514/432 |
| 6,596,758 B1 | 7/2003 | Brunet et al. |
| 7,655,699 B1 | 2/2010 | Boehm |
| 8,101,662 B2 | 1/2012 | Chandraratna |
| 8,389,538 B2 | 3/2013 | Kakuta et al. |
| 8,460,576 B2 | 6/2013 | Kurisawa et al. |
| 8,475,775 B1 | 7/2013 | Brouillette |
| 9,174,917 B2 * | 11/2015 | Wagner ................... C07C 63/66 |
| 9,193,672 B2 | 11/2015 | Yu |
| 9,573,906 B2 * | 2/2017 | Wagner ................ C07D 239/28 |

(Continued)

FOREIGN PATENT DOCUMENTS

| | | |
|---|---|---|
| EP | 0637297 B1 | 8/2000 |
| EP | 1180520 A1 | 2/2002 |

(Continued)

OTHER PUBLICATIONS

Love; J Clin Pathol 2006, 59, 1151-1159. (Year: 2006).*

(Continued)

*Primary Examiner* — Daniel R Carcanague

(74) *Attorney, Agent, or Firm* — Viksnins Harris Padys Malen LLP

(57) ABSTRACT

The invention provides compounds of formula I:

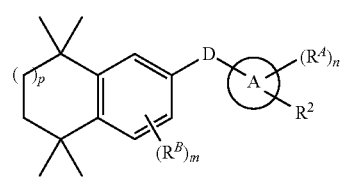

and salts thereof, as well as pharmaceutical compositions comprising such compounds. The compounds are useful for treating cancers, Alzheimer's disease, and conditions associated with demyelination.

11 Claims, 2 Drawing Sheets

(56) References Cited

U.S. PATENT DOCUMENTS

| | | | |
|---|---|---|---|
| 9,596,758 B2 | 3/2017 | Tatsuta | |
| 9,908,856 B2* | 3/2018 | Wagner | C07D 249/18 |
| 10,005,741 B2 | 6/2018 | Wagner et al. | |
| 2003/0008273 A1 | 1/2003 | Perlmann et al. | |
| 2003/0135053 A1 | 7/2003 | Bernardon | |
| 2005/0038098 A1* | 2/2005 | Tachdjian | C07D 277/34 514/406 |
| 2006/0106072 A1* | 5/2006 | Boehm | C07C 63/49 514/355 |
| 2007/0129392 A1 | 6/2007 | Hong et al. | |
| 2007/0185055 A1 | 8/2007 | Jiang et al. | |
| 2010/0010084 A1 | 1/2010 | Yu | |
| 2010/0029689 A1 | 2/2010 | Hopper | |
| 2010/0105728 A1 | 4/2010 | Lagu | |
| 2010/0120742 A1 | 5/2010 | Kakuta | |
| 2010/0144821 A1 | 6/2010 | Carter et al. | |
| 2011/0253936 A1 | 10/2011 | Kurisawa et al. | |
| 2012/0309833 A1* | 12/2012 | Wagner | C07C 63/66 514/569 |
| 2014/0343079 A1* | 11/2014 | Wagner | C07D 239/28 514/256 |
| 2016/0263189 A1 | 9/2016 | Burstein | |
| 2016/0338981 A1* | 11/2016 | Marshall | A61K 31/192 |
| 2017/0008859 A1* | 1/2017 | Wagner | A61K 31/505 |
| 2017/0182046 A1* | 6/2017 | Wagner | A61K 31/505 |
| 2018/0065936 A1 | 3/2018 | Wagner et al. | |
| 2018/0072697 A1 | 3/2018 | Wagner et al. | |
| 2018/0141921 A1 | 5/2018 | Wagner et al. | |
| 2018/0207125 A1* | 7/2018 | Wagner | A61K 31/352 |
| 2018/0207126 A1* | 7/2018 | Wagner | A61K 31/352 |
| 2018/0207156 A1* | 7/2018 | Wagner | A61K 31/505 |

FOREIGN PATENT DOCUMENTS

| | | | |
|---|---|---|---|
| JP | 11-503472 A | 3/1999 | |
| JP | H11343263 A | 12/1999 | |
| JP | 2001522350 A | 11/2001 | |
| JP | 2002515025 A | 5/2002 | |
| JP | 2010111588 A | 5/2010 | |
| JP | 2013052386 A | 3/2013 | |
| JP | 2014076953 A | 5/2014 | |
| JP | 5784045 B2 | 10/2017 | |
| WO | 1993021146 A1 | 10/1993 | |
| WO | 1994015902 A1 | 7/1994 | |
| WO | WO-9807716 A2 * | 2/1998 | C07C 69/94 |
| WO | 1998045242 A1 | 10/1998 | |
| WO | 1999051562 A1 | 10/1999 | |
| WO | 1999056740 A1 | 11/1999 | |
| WO | 2000064260 A1 | 11/2000 | |
| WO | 2002018361 A2 | 3/2002 | |
| WO | 2002049632 A1 | 6/2002 | |
| WO | 2002086062 A3 | 10/2002 | |
| WO | 2004058762 A1 | 7/2004 | |
| WO | 2004093809 A2 | 11/2004 | |
| WO | 2005058803 A1 | 12/2004 | |
| WO | 2005000233 A2 | 1/2005 | |
| WO | 2005011573 A2 | 2/2005 | |
| WO | 2005013949 A2 | 2/2005 | |
| WO | 2005058301 A1 | 6/2005 | |
| WO | 2005058798 A2 | 6/2005 | |
| WO | 2006036394 A2 | 4/2006 | |
| WO | 2007022437 A2 | 2/2007 | |
| WO | 2007063681 A1 | 6/2007 | |
| WO | 2008025965 A2 | 3/2008 | |
| WO | 2008105386 A1 | 9/2008 | |
| WO | 2010096264 A2 | 8/2010 | |
| WO | 2011006157 A2 | 1/2011 | |
| WO | 2011062017 A1 | 5/2011 | |
| WO | 2011103321 A1 | 8/2011 | |
| WO | 2013040227 A2 | 3/2013 | |
| WO | 201356232 A2 | 4/2013 | |
| WO | 2015109318 A2 | 7/2015 | |
| WO | 2015130973 A1 | 9/2015 | |
| WO | WO2015130973 * | 9/2015 | |
| WO | 2016140979 A1 | 9/2016 | |

OTHER PUBLICATIONS

Lippert; ChemMedChem 2009, 4, 1143-1152. (Year: 2009).*
Boehm; J. Med. Chem. 1995, 38, 3146-3155. (Year: 1995).*
Chemical Abstracts STN Registry Database; record for RN 1207107-44-5, entered into the database on Feb. 22, 2010. (Year: 2010).*
Nadeem; World J Neurol 2015, 5, 5-16. (Year: 2015).*
Santin; J. Med. Chem. 2009, 52, 3150-3158. (Year: 2009).*
Brown; J. Med. Chem. 2004, 47, 1008-1017. (Year: 2004).*
Spruce; J. Med. Chem. 1991, 34, 430-439. (Year: 1991).*
Spruce; J. Med. Chem. 1987 30, 8, 1474-1482. (Year: 1987).*
Lubet, et al., "Chemopreventive efficacy of Targretin in rodent models of urinary bladder, colon/intestine, head and neck and mammary cancers", Oncol Rep 27(5), 1400-1406 (2012).
Luettich, et al., "Systems toxicology approaches enable mechanistic comparison of spontaneous and cigarette smoke-related lung tumor development in the A/J mouse model", Interdiscip Toxicol 7(2), 73-84 (2014).
Mangelsdorf, et al., "A direct repeat in the cellular retinol-binding protein type II gene confers differential regulation by RXR and RAR", Cell 66, 555-561 (1991).
Mangelsdorf, et al., "The RXR heterodimers and orphan receptors", Cell 83, 841-850 (1995).
Marshall, et al., "Analysis of differential secondary effects of novel rexinoids: select rexinoid X receptor ligands demonstrate differentiated side effect profiles", Pharma Res Per 3(2), e00122 (2015).
Marshall, "Using *Saccharomyces cerevisiae* to Test the Mutagenicity of Household Compounds: An Open Ended Hypothesis-Driven Teaching Lab", CBE-LSE 6, 307-315 (2007).
McFarland et al., "Low Dose Bexarotene Treatment Rescues Dopamine Neurons and Restores Behavioral Function in Models of Parkinson's Disease", ACS Chemical Neuroscience 4(11), 1430-1438 (2013).
McFarland, "Pimavanserin, a 5-HT2A inverse agonist, reverses psychosis-like behaviors in a rodent model of Parkinson's disease", Behav. Pharmacol. 22, 681-692 (2011).
Michellys, et al., "Design and Synthesis of Novel RXR-Selective Modulators with Improved Pharmacological Profile.", Bioorg Med Chem Lett 13, 4070-4075 (2003).
Michellys, "Design, synthesis and structure-activity relationship of novel RXR-selective modulators.", Bioorg Med Chem Lett 14, 1593-1598 (2004).
Michellys, et al., "Design, synthesis, and structure-activity relationship studies of novel 6,7-locked-[7-(2-alkoxy-3,5-dialkylbenzene)-3-methylocta]-2,4,6-trienoic acids.", J Med Chem 46, 4087-4103 (2003).
Michellys, et al., "Novel (2E,4E,6Z)-7-(2-alkoxy-3,5-dialkylbenzene)-3-methylocta-2,4,6-trienoic acid retinoid X receptor modulators are active in models of type 2 diabetes.", J Med Chem 46, 2683-2696 (2003).
Miller, et al., "Initial clinical trial of a selective retinoid X receptor ligand, LGD1069", J. Clin. Oncol. 15, 790-795 (1997).
Morishita, et al., "Retinoid X Receptor Ligands with Anti-Type 2 Diabetic Activity", https://www.ncbi.nlm.nih.gov/pubmed/27320332 (2017).
Morris, et al., "AutoDock4 and AutoDockTools4: Automated Docking with Selective Receptor Flexibility", J. Comput. Chem. 30(16), 2785-2791 (2009).
Mortelmans, "The Amse *Salmonella*/microsome mutagenicity assay", Mutat Res 455, 29-60 (2000).
Muccio, et al., "Conformationally Defined Retinoic Acid Analogues. 4. Potential New Agents for Acute Promyelocytic and Juvenile Myelomonocytic Leukemias", Journal of Medicinal Chemistry 41(10), 1679-1687 (1998).
Mukherjee, et al., "Sensitization of diabetic and obese mice to insulin by retinoid X receptor agonists", Nature 386, 407-410 (1997).

(56) References Cited

OTHER PUBLICATIONS

Murthy, et al., "LXR/RXR activation enhances basolateral efflux of cholesterol in CaCo-2 cells", J. Lipid Res. 43, 1054-1064 (2002).
Nahoum, et al., "Modulators of the structural dynamics of the retinoid X receptor to reveal receptor function.", Proc Natl Acad Sci 104, 17323-17328 (2007).
Nakatsuka, et al., "RXR antagonism induces G0/G1 cell cycle arrest and ameliorates obesity by up-regulating the p53-p21Cip1 pathway in adipocytes", The Journal of Pathology 226, 784-795 (2012).
Nakayama, et al., "Discovery of a Potent Retinoid X Receptor Antagonist Structurally Closely Related to RXR Agonist NEt-3IB", ACS Med Chem Lett 2(12), 896-900 (2011).
Natrajan, et al., "Retinoid X receptor activation reverses age-related deficiencies in myelin debris phagocytosis and remyelination", Brain 138 (Pt 12), 3581-3597 (2015).
Nunez, et al., "Retinoid X receptor alpha controls innate inflammatory responses through the up-regulation of chemokine expression", Proc Natl Acad Sci USA 107(23), 10626-10631 (2010).
O'Boyle, et al., "Open Babel: An open chemical toolbox", J. Cheminf. 3(33), 14 pages (2011).
Ohsawa, et al., "Mechanism of Retinoid X Receptor Partial Agonistic Action of 1-(3,5,5,8,8-Pentamethyl-5,6,7,8-tetrahydro-2-naphthyl)-1H-benzotriazole-5-carboxylic Acid and Structural Development To Increase Potency", J. Med. Chem. 56, 1865-1877 (2013).
Ohta, et al., "Diphenylamine-based retinoid antagonists: regulation of RAR and RXR function depending on the N-substituent", Bioorganic & Medicinal Chemistry 19, 2501-2507 (2011).
Ohta, et al., "Potent Retinoid Synergists with a Diphenylamine Skeleton", Biological & Pharmaceutical Bulletin 21(5), 544-546 (1998).
Okayama University, "Synthesis of novel homeostasis modulators by "Westernized Kampo Medicine"—Retinoid X Receptor Partial-Agonists Exert Anti-type 2 Diabetes Effects with Less Adverse Effects than Full-Agonists—", Okayama University eBulletin 7, pp. 20-21 (Jun. 2014).
Olefsky, "Nuclear Receptor Minireview Series", J. Biol. Chem. 276(40), 36863-36864 (2001).
Ordentlich, et al., "Identification of the antineoplastic agent 6-mercaptopurine as an activator of the orphan nuclear hormone receptor Nurr1", J. Biol. Chem. 278(27), 24791-24799 (2003).
Pangborn, et al., "Safe and Convenient Procedure for Solvent Purification", Organometallics 15, 1518-1520 (1996).
Parry, et al., "A Boronated Benzamide as Melanoma-Seeking Agent", Bioorg Med Chem Lett 7(3), 361-364 (1997).
Perlmann, et al., "A novel pathway for vitamin a signaling mediated by RXR heterodimerization with NGFI-B and NURR1", Genes & Dev. 9, 769-782 (1995).
Perlmann, "Retinoid Metabolism: a balancing act", Nature Genetics 31, 7-8 (2002).
Prado-Garcia, et al., "Tumor-induced CD8+ T-cell dysfunction in lung cancer patients", Clin Dev Immunol 2012, Article ID 741741, 11 pages, doi: 10.1155/2012/741741 (2012).
Prince, et al., "Bexarotene capsules and gel for previously treated patients with cutaneous T-cell lymphoma: Results of the Australian patients treated on phase II trials.", Australasian Journal of Dermatology 42, 91-97 (2001).
Pubchem, CID-58901647, create date Aug. 19, 2012.
Qing, et al., "A Suzuki Coupling Approach to Trifluoromethyl Derivative of Targretin (LGD 1069).", Bioorganic & Medicinal Chemistry. 17(16), 2117-2120 (1997).
Rendi, et al., "The selective estrogen receptor modulator arzoxifene and the rexinoid LG100268 cooperate to promote transforming growth factor beta-dependent apoptosis in breast cancer", Cancer Res 64(10), 3566-3571 (2004).
Repa, et al., "Regulation of mouse sterol regulatory element-binding protein-1c gene (SREBP-1c) by oxysterol receptors, LXRalpha and LXRbeta", Genes Dev 14(22), 2819-2830 (2000).
Rigas, "Emerging role of rexinoids in non-small cell lung cancer: focus on bexarotene", Oncologist 10, 22-33 (2005).
Rizvi, et al., "A Phase I study of LGD1069 in adults with advanced cancer", Clin. Cancer Res. 5, 1658-1664 (1999).
Sacchetti, et al., "Nurr1 enhances transcription of the human dopamine transporter gene through a novel mechanism", J. Neurochem. 76, 1565-1572 (2001).
Safaryn, et al., "A convenient synthesis of (±) ascochlorin", Tetrahedron 42(10), 2635-2642 (1986).
Saijo, et al., "A Nurr1/CoREST pathway in microglia and astrocytes protects dopaminergic neurons from inflammation induced death", Cell 137, 47-59 (2009).
Sakaki, et al., "Synthesis and Structure-activity Relationship of Nocel RXR antagonists: orally active antidiabetic and antiobesity agents.", Bioorg Med Chem Lett 17, 4804-4807 (2007).
Sakurada, et al., "Nurr1, an orphan nuclear receptor, is a transcriptional activator of endogenous tyrosine hydroxylase in neural progenitor cells derived from the adult brain", Development 126, 4017-4026 (1999).
Sanders, et al., "A Phase 1 Clinical Study of the Retinoid X Receptor (RXR) Selective Agonist IRX4204 in Patients with Early Parkinson's Disease (PD) (P2.342)", http://n.neurology.org/content/86/16_Supplement/P2.342 , First published Apr. 4, 2016.
Schimmel, et al., "4.5 kb of the rat tyrosine hydroxylase 5' flanking sequence directs tissue specific expression during development and contains consensus sites for multiple transcription factors", Mol. Brain Res. 74,1-14 (1999).
Adams, et al., "Discovery of GSK1070916, a Potent and Selective Inhibitor of Aurora B/C Kinase", J. Med. Chem. 53, 3973-4001 (2010).
Altucci, et al., "RAR and RXR modulation in cancer and metabolic disease.", Nature Rev Drug Discovery 6, 793-810 (2007).
Amoutzias, "A protein interaction atlas for the nuclear receptors: properties and quality of a hub-based dimerisation network", BMC Syst. Biol. 1, 34, 12 pages (2007).
Assaf, "Minimizing adverse side-effects of oral bexarotene in cutaneous T-cell lymphoma: an expert opinion.", Br. J. Dermatol. 155, 261-266 (2006).
Atigadda, et al., "Conformationally Defined Retinoic Acid Analogues. 5. Large-Scale Synthesis and Mammary Cancer Chemopreventive Activity for (2E,4E,6Z,8E)-8-(3',4'-Dihydro-1'(2'H)-naphthalen-1'-ylidene)-3,7-dimethyl-2,4,6-octatrienoic Acid (9cUAB30)", Journal of Medicinal Chemistry 46(17), 3766-3769 (2003).
Atigadda, et al., "Methyl substitution of a rexinoid agonist improves potency and reveals site of lipid toxicity", Journal of Medicinal Chemistry 57(12), 5370-5380 (2014).
Batie, et al., "Synthesis and biological evaluation of halogenated curcumin analogs as potential nuclear receptor selective agonists", Bioorganic Med Chem 21(3), 693-702 (2013, epub 2012).
Blumenschein, et al., "Phase III trial comparing carboplatin, paclitaxel, and bexarotene with carboplatin and paclitaxel in chemotherapy-naive patients with advanced or metastatic non-small-cell lung cancer: Spirit II", J Clin Oncol 26(11), 1879-1885 (2008).
Boehm, et al., "Synthesis and Structure-Activity Relationships of Novel Retinoid X Receptor-Selective Retinoids.", Journal of Medicinal Chemistry 37, 2930-2941 (1994).
Brown, et al., "Combination Chemoprevention of HER2/neu-Induced Breast Cancer Using a Cyclooxygenase-2 Inhibitor and a Retinoid X Receptor-Selective Retinoid", Cancer Prev Res (Phila) 1(3), 208-214 (2008).
Bruson, et al., "Cycli-Alkylation of Aromatic Compounds by the Friedel and Crafts Reaction", J Am Chem Soc 62(1), 36-44 (1940).
Caetano, et al., "IL6 Blockade Reprograms the Lung Tumor Microenvironment to Limit the Development and Progression of K-ras-Mutant Lung Cancer", Cancer Res 76(11), 3189-3199 (2016).
Cao, et al., "The Rexinoids LG100268 and LG101506 Inhibit Inflammation and Suppress Lung Carcinogenesis in A/J Mice", Cancer Prev Res (Phila) 9(1), 105-114 (2016, epub 2015).
Carpentier, "The glucocorticoid receptor is a co-regulator of the orphan nuclear receptor Nurr1", J. Neurochem. 104, 777-789 (2008).
Cesario, et al., "Differentiation and growth inhibition mediated via the RXR:PPARgamma heterodimer in colon Cancer", cancer Letters 240(2), 225-233 (2006).
Chu, "Nurr1 in Parkinson's disease and related disorders", J. Comp. Neurol. 494, 495-514 (2006).

(56) References Cited

OTHER PUBLICATIONS

Claudel, et al., "Reduction of atherosclerosis in apolipoprotein E knowout mice by activation of the retinoid X receptor", PNAS 98 (5), 2610-2615 (2001).
Cramer, et al., "ApoEdirected therapeutics rapidly clear β-amyloid and reverse deficits in AD mouse models", Science 335, 1503-1506 (2012).
Crunkhorn, "RXR agonist reverses Alzheimer's disease", Nature Reviews Drug Discovery 11, 271 (2012).
Dai, et al., "Liver X receptor β protects dopaminergic neurons in a mouse model of Parkinson disease", Proc. Natl. Acad. Sci. U.S.A. 109, 13112-13117 (2012).
Daiss, et al., "Synthesis, Crystal Structure Analysis, and Pharmacological Characterization of Disila-bexarotene, a Disila-Analogue of the RXR-Selective Retinoid Agonist Bexarotene.", Organometallics 24, 3192-3199 (2005).
Danziger, "Automated Site-Directed Drug Design: A General Algorithm for Knowledge Acquisition about Hydrogen-Bonding Regions at Protein Surfaces", Proceedings of the Royal Society of London, Series B, Biological Sciences, 236 (1283), 101-113 (1989).
Dawson, et al., "Conformational effects on retinoid receptor selectivity. 2. Effects of retinoid bridging group on retinoid X receptor activity and selectivity.", J Med Chem 38, 3368-3383 (1995).
Dawson, et al., "sp2-Bridged Diaryl Retinoids: Effects of Bridge-Region Substitution on Retinoid X Receptor (RXR) Selectivity", Bioorganic & Medicinal Chemistry Letters 10, 1307-1310 (2000).
Dawson, et al., "The Receptor-DNA Determines the Retinoid Response: a Mechanism for the Diversification of the Ligand Signal.", Molecular and Cellular Biology 16(8), 4137-4146 (1996).
Dimick, et al., "On the Meaning of Affinity: Cluster Glycoside Effects and Concanavalin A.", J Am Chem Soc 121, 10286-10296 (1999).
Dragnev, et al., "A Proof-of-Principle Clinical Trial of Bexarotene in Patients with Non-Small Cell Lung Cancer", Clin. Cancer Res. 13, 1794-1800 (2007).
Dragnev et al., "Bexarotene plus erlotinib suppress lung carcinogenesis independent of KRAS mutations in two clinical trials and transgenic models", Cancer Prev Res (Phila) 4(6), 818-828 (2011).
Dubois, et al., "Identification of a potent agonist of the orphan nuclear receptor Nurr1", ChemMedChem 1, 955-958 (2006).
Duvic, et al., "BexaroteneWorldwide Study Group. Bexarotene is effective and safe for treatmentof refractory advanced-stage cutaneous T-cell lymphoma: multinationalphase II-III trial results", J. Clin. Oncol. 19, 2456-24571 (2001).
Edelman, et al., "Phase II trial of the novel retinoid, bexarotene, and gemcitabine plus carboplatin in advanced non-small-cell lung cancer", J Clin Oncol 23(24), 5774-5778 (2005).
Egea, et al., "Molecular recognition of agonist ligands by RXRs", Mol. Endocrinol. 16, 987-997 (2002).
Esteva, et al., "Multicenter Phase II Study of Oral Bexarotene for Patients With Metastatic Breast Cancer", Journal of Clinical Oncology 21(6), 999-1006 (2003).
Evans, et al., "Nuclear Receptors, RXR, and the Big Bang", Cell 157(1), 255-266 (2014).
Fantini, et al., "Bexarotene Blocks Calcium-Permeable Ion Channels Formed by Neurotoxic Alzheimer's beta-Amyloid Peptides", ACS Chemical Neuroscience 5(3), 216-224 (2014).
Farmer, et al., "Aza-retinoids as novel retinoid X receptor-specific agonists", Bioorg. Med. Chem. Lett. 16, 2352-2356 (2006).
Faul, et al., "Synthesis of Novel Retinoid X Receptor-Selective Retinoids.", J Org Chem 66, 5772-5782 (2001).
Feng-Ling, et al., "A Suzuki Coupling Approach to Trifluoromethyl Derivative of Targretin (LGD 1069)", Bioorganic and Medicinal Chemistry Letters, 7 (16), 2117-2120 (1997).
Field, et al., "LXR/RXR ligand activation enhances basolateral efflux of beta-sitosterol in CaCo-2 cells", J. Lipid Res. 45, 905-913 (2004).
Forman, et al., "Unique response pathways are established by allosteric interactions among nuclear hormone receptors", Cell 81, 541-550 (1995).

Friling, et al., "Activation of Retinoid X Receptor increases dopamine cell survival in models for Parkinson's disease", BMC Neurosci. 10, 146-153 (2009).
Fujii, et al., "Effect of a retinoid X receptor partial agonist on airway inflammation and hyperresponsiveness in a murine model of asthma", Respir Res 18(23), 10 pages (2017).
Fujii, et al., "Metabolic inactivation of retinoic acid by a novel P450 differentially expressed in developing mouse embryos.", The EMBO Journal 16(14), 4163-4173 (1997).
Fujii, et al., "Modification at the acidic domain of RXR agonists has little effect on permissive RXR-heterodimer activation", Bioorganic & Medicinal Chemistry Letters 20, 5139-5142 (2010).
Furmick, et al., "Modeling, synthesis and biological evaluation of potential retinoid X receptor-selective agonists: novel halogenated analogues of 4-[1-(3,5,5,8,8-pentamethy1-5,6,7,8-tetrahydro-2-naphthyl)ethynyl]benzoic acid (bexarotene)", ChemMedChem 7(9), 1551-1566 (2012).
Galleguillos, "Nurr1 regulates RET expression in dopamine neurons of adult ratmidbrain", J. Neurochem. 114, 1158-1167 (2010).
Gandi, "Reactions of Some Aromatic Nitro Compounds with Alkali Metal Amides.", J Org Chem 44(25), 4705-4707 (1979).
Garcia, et al., "Pyrazine arotinoids with inverse agonist activities on the retinoid and rexinoid receptors", ChemBioChem 10, 1252-1259 (2009).
Gernert, et al., "Design and Synthesis of Fluorinated RXR Modulators.", Bioorg Med Chem Lett 13, 3191-3195 (2003).
Gorelik, et al., "Susceptibility of Various Strains of Mice to Urethan-Induced Lung Tumors and Depressed Natural Killer Cell Activity", J Natl Cancer Inst 67(6), 1317-1322 (1981).
Gorman, et al., "In vitro metabolic characterization, phenotyping, and kinetic studies of 9cUAB30, a retinoid X receptor-specific retinoid", Drug Metabolism & Disposition 35(7), 1157-1164 (2007).
Grenningloh, et al., "Cutting Edge: Inhibition of the Retinoid X Receptor (RXR) Blocks T Helper 2 Differentiation and Prevents Allergic Lung Inflammation", J. Immunol. 176, 5161-5166 (2006).
Grubbs, et al., "9cUAB30, an RXR specific retinoid, and/or tamoxifen in the prevention of methylnitrosourea-induced mammary cancers", Cancer Letters 201, 17-24 (2003).
Guibert, et al., "KRAS Mutations in Lung Adenocarcinoma: Molecular and Epidemiological Characteristics, Methods for Detection, and Therapeutic Strategy Perspectives", Curr Mol Med 15(5), 418-432 (2015).
Hansen, et al., "The low-toxicity 9-cis UAB30 novel retinoid down-regulates the DNA methyltransferases and has anti-telomerase activity in human breast cancer cells", International Journal of Oncology 30(3), 641-650 (2007).
Heck, et al., "Modeling, Synthesis, and Biological Evaluation of Potential Retinoid X Receptor (RXR)-Selective Agonists: Analogues of 4-[1-(3,5,5,8,8-Pentamethyl-5,6,7,8-tetrahydro-2-naphthyl)ethynyl]benzoic Acid (Bexarotene) and 6-(Ethyl(5,5,8,8-tetrahydronaphthalen-2-y", J Med Chem 59(19), 8924-8940 (2016).
Heller, et al., "Synthetic retinoids in dermatology.", Canadian Medical Association Journal 132(10), 1129-1136 (1985).
Heo, et al., "Effect of bexarotene on differentiation of glioblastoma multiforme compared with ATRA", Clin Exp Metastasis 33(5), 417-429 (2016).
Hermanson, et al., "Nurr1 regulates dopamine synthesis and storage in MN9Ddopamine cells", Exp. Cell Res. 288, 324-334 (2003).
Hintermann, et al., "Identification of a series of highly potent activators of the Nurr1 signaling pathway", Bioorg. Med. Chem. Lett. 17,193-196 (2007).
Huang, et al., "Retinoid X receptor gamma signaling accelerates CNS remyelination", Nature Neuroscience 14, 45-53 (2011).
Huang, et al., "Studies on the structure-activity relationship of retinoids—Hansch analysis and 3DQSAR studies on specific ligands of retinoid X receptor", CAS Scifinder Abstract 33, 442-448 (1998).
Iriki, et al., "The cell-cell interaction between tumor-associated macrophages and small cell lung cancer cells is involved in tumor progression via STAT3 activation", Lung Cancer 106, 22-32 (2017).
Jackman, et al., "Impact of epidermal growth factor receptor and KRAS mutations on clinical outcomes in previously untreated

(56) References Cited

OTHER PUBLICATIONS non-small cell lung cancer patients: results of an online tumor registry of clinical trials", Clin Cancer Res 15(16), 5267-5273 (2009).

Jin, et al., "Reaction mechanism of synthesizing hydroxyterepthalic acid monoester with high selectivity and its application", Huagong Xuebao (Chinese Edition with English Abstract) 63(10), 3337-3344 (2012).

Jong, et al., "Conformational effects on retinoid recepetor selectivity. 1. Effect of 9-double bond geometry on retinoid X receptor activity.", J Med Chem 36, 2605-2613, (1993).

Jurutka, et al., "Modeling, synthesis, and biological evaluation of potential retinoid X receptor (RXR) selective agonists: novel analogues of 4-[1-(3,5,5,8,8-pentamethyl-5,6,7,8-tetrahydro-2-naphthyl)ethynyl]benzoic acid (bexarotene) and (E)-3-(3-(1,2,3,4-tetrahydro-1,1,4,", Journal of Medicinal Chemistry 56, 8432-8454 (2013).

Kadkhodaei, et al., "Nurr1 is required formaintenance of maturing and adult midbrain dopamine neurons", J. Neurosci. 29, 15923-15932 (2009).

Kagechika, et al., "Retinobenzoic acids. 1. Structure-activity relationships of aromatic amides with retinoidal activity", J. Med Chem 31, 2182-2192 (1988).

Kakuta, et al., "RXR Partial Agonist CBt-PMN Exerts Therapeutic Effects on Type 2 Diabetes without the Side ffects of RXR Full Agonists", ACS Medicinal Chemistry Letters 3, 427-432 (2012).

Kakuta, "Western-style Chinese (Kampo) medicine targeting retinoid X receptors (RXRs)", 248th ACS National Meeting, MEDI 102, San Francisco, CA. (Aug. 10-14, 2014).

Kamphorst, et al., "Proliferation of PD-1+CD8 T cells in peripheral blood after PD-1-targeted therapy in lung cancer patients", Proc Natl Acad Sci USA 114(19), 4993-4998 (2017).

Kapetanovic, et al., "Murine Oncogenicity and Pharmacokinetics Studies of 9-cis-UAB30, an RXR Agonist, for Breast Cancer Chemoprevention", International Journal of Toxicology 29(2), 157-164 (2010).

Kawata, et al., "RXR partial agonist produced by side chain repositioning of alkoxy RXR full agonist retains antitype 2 diabetes activity without the adverse effects", J Med Chem 58(2), 912-926 (2015, epub 2014).

Keenan, et al., "Conformational Preferences in a Benzodiazepine Series of Potent Nonpeptide Fibrinogen Receptor Antagonists.", J Med Chem 42, 545-559, (1999).

Khuri, et al., "Multi-Institutional Phase I/II Trial of Oral Bexarotene in Combination With Cisplatin and Vinorelbine in Previously Untreated Patients With Advanced Non-Small-Cell Lung Cancer", Journal of Clinical Oncology 19, 2626-2637 (2001).

Kiick et al., "Incorporation of azides into recombinant proteins for chemoselective modification by the Staudinger igation", Proc. Natl. Acad. Sci. U.S.A. 99(1), 19-24 (2002).

Kishi, et al., "Significance of the progesterone receptor and epidermal growth factor receptor, but not the estrogen receptor, in chemically induced lung carcinogenesis in female A/J mice", Oncol Lett 8(6), 2379-2386 (2014).

Kobayashi, et al., "Positron emission tomography to elucidate pharmacokinetic differences of regioisomeric retinoid x receptor agonists", ACS Med Chem Lett 6(3), 334-338 (2015).

Koch, et al., "Identification of the First Retinoid X Receptor Homodimer Antagonist", J Med Chem 39(17), 3229-3234 (1996).

Koch, et al., "Synthesis of Retinoid X Receptor-Specific Ligands That Are Potent Inducers of Adipogenesis in 3T3-L1 Cells", Journal of Medicinal Chemistry 42, 742-750 (1999).

Kolesar, et al., "A pilot, first-in-human, pharmacokinetic study of 9cUAB30 in healthy volunteers", Cancer Prevention Research 3(12), 1565-1570 (2010).

Kowanetz, et al., "Granulocyte-colony stimulating factor promotes lung metastasis through mobilization of Ly6G+Ly6C+ granulocytes", Proc Natl Acad Sci USA 107(50), 21248-21255 (2010).

La Vista-Picard, et al., "The receptor-DNA complex determines the retinoid response: a mechanism for the diversification of the ligand signal.", Molecular and Cellular Biology 16(8), 4137-4146 (1996).

Lagu, et al., "RXR-LXR heterodimer modulators for the potential treatment of dyslipidemia", Bioorganic & Medicinal Chemistry Letters 17, 3497-3503 (2007).

Le, "Decreased NURR1 gene expressionin patients with Parkinson's disease", J. Neurol. Sci. 273, 29-33 (2008).

Le, "Mutations in NR4A2 associated withfamilial Parkinson disease", Nat. Genet. 33, 85-89 (2003).

Lehmann, et al., "Retinoids selective for retinoid X receptor pathways.", Science 258, 1944-1946 (1992).

Leid, et al. "Multiplicity Generates Diversity in the Retinoic Acid Signaling Pathways", Trends Biochem. Sci. 17, 427-433 (1992).

Lerner, et al. "Bexarotene as add-on to antipsychotic treatment in schizophrenia patients: a pilot open-label trial.", Clinical Neuropharmacology 31(1), 25-33 (2008).

Lerner, et al., "The retinoid X receptor agonist bexarotene relieves positive symptoms of schizophrenia: a 6-week, randomized, double-blind, placebo-controlled multicenter trial", The Journal of Clinical Psychiatry 74(12), 1224-1232 (2013).

Li, et al. "Functional Evidence for Retinoid X Receptor (RXR) as a Nonsilent Partner in the Thyroid Hormone Receptor/RXR Heterodimer", Mol. Cell. Biol. 22, 5782-5792 (2002).

Liby et al. "A new rexinoid, NRX194204, prevents carcinogenesis in both the lung and mammary gland", Clin Cancer Res 13(20), 6237-6243 (2007).

Liby, et al. "Rexinoids for prevention and treatment of cancer: opportunities and challenges", Curr Top Med Chem 17 (6), 721-730 (2017, available online 2016).

Liby, et al., "Synthetic Triterpenoids Prolong Survival in a Transgenic Mouse Model of Pancreatic Cancer", Cancer Prevention Research 3(11), 1427-1434 (2010).

Liby, et al., "Triterpenoids and rexinoids as multifunctional agents for the prevention and treatment of cancer", Nat Rev Cancer 7(5), 357-369 (2007).

Liby, et al., "Triterpenoids CDDO-methyl ester or CDDO-ethyl amide and rexinoids LG100268 or NRX194204 for prevention and treatment of lung cancer in mice", Cancer Prev Res (Phila) 2(12), 1050-1058 (2009).

Lindeblad, et al., "Assessment of oral toxicity and safety of 9-cis-UAB30, a potential chemopreventive agent, in rat and dog studies", Drug and Chemical Toxicology 34(3), 300-310 (2011).

Liu, et al., "IRX4204 in combination with erlotinib to target distinct pathways in lung cancer cells", J Clin Oncol 35(15 suppl), abstract e14095 (2017), http://ascopubs.org/doi/abs/10.1200/JCO.2017.35.15_suppl.e14095 (downloaded Aug. 3, 2018).

Love, et al., "The structural basis for the specificity of retinoid-X receptor-selective agonists: new insights into the role of helix H12", J. Biol. Chem. 277(13), 11385-11391 (2002).

Schinelli, et al., "1-Methyl-4-phenyl-1,2,3,6-tetrahydropyridine metabolism and 1-methyl-4-phenylpyridinium uptake in dissociated cell cultures from the embryonic mesencephalon", J. Neurochem. 50(6), 1900-1907 (1988).

Sherman, et al., "Central hypothyroidism associated with retinoid X receptor-selective ligands", N. Engl. J. Med. 340(14), 1075-1079 (1999).

Shibakura, et al., "Anticoagulant Effects of Synthetic Retinoids Mediated Via Different Receptors on Human Leukemia and Umbilical Vein Endothelial Cells.", Blood 90(4), 1545-1551 (1997).

Simone, "Oncology: Introduction, Cecil Textbook of Medicine", 20th Edition, vol. 1, 1004-1010 (1996).

Sleiman, et al., "Characterisation of a novel NR4A2 mutation in Parkinson's diseasebrain", Neurosci. Lett. 457, 75-79 (2009).

Sporn, "Retinoids and Cancer Prevention.", Cancer Journal for Clinicians 29(2), 120-125 (1979).

Svensson, et al., "Crystal structure of the heterodimeric complex of LXRa and RXRb ligand-binding domains in a fully agonistic conformation", EMBO J. 22(18), 4625-4633 (2003).

Takahasi, et al., "2,5-Diaryl-1,3,2-dioxaborinanes: A New Series of Liquid Crystals.", Bull Chem Soc 62(12), 3896-3901 (1989).

Takamatsu, et al., "The first potent subtype-selective retinoid X receptor (RXR) agonist possessing a 3-isopropoxy-4-

(56) References Cited

OTHER PUBLICATIONS isopropylphenylamino moiety, NEt-3IP (RXRalpha/beta-dual agonist)", ChemMedChem 3(5), 780-787 (2008).
Tan, et al., "Monitoring interactions between receptor tyrosine kinases and their downstream effector proteins in living cells using bioluminescence resonance energy transfer", Mol. Pharmacol. 72 (6), 1440-1446 (2007).
Tang, et al., "Myeloid-derived suppressor cell and macrophage exert distinct angiogenic and immunosuppressive effects in breast cancer", Oncotarget 8(33), 54173-54186 (2017).
Thacher, et al., "Receptor Specificity of Retinoid-Induced Epidermal Hyperplasia: Effect of RXR-Selective Agonists and Correlation with Topical Irritation", Journal Pharmacology and Experimental Therapeutics 282(2), 528-534 (1997).
Thalesnano Nanotechnology Inc., "H-Cube Continuous-flow hydrogenation reactor", www.thalesnano.com/n-cube, Published: Apr. 9, 2006, Retrieved: Dec. 29, 2014.
Thomas, "Retinoid Metabolism: a balancing act.", Nature Genetics 31, 7-8 (2002).
Thompson, et al., "Distinct retinoid X receptor activation dunction-2 residues mediate transactivation in homodimeric and vitamin D receptor heterodimeric contexts", J. Mol. Endocrinol. 27(2), 211-227 (2001).
Traynelis, et al., "Ylide Methylation of Aromatic Nitro Compounds.", J Org Chem 31, 243-247 (1964).
Uray, et al., "Retinoids and rexinoids in cancer prevention: from laboratory to clinic", Semin Oncol 43(1), 49-64 (2016, epub 2015).
Vahlquist, "What are Natural Retinoids.", Dermatology 199(Suppl 1), 3-11 (1999).
Vuligonda, et al., "Enantioselective Synthesis of Potent Retinoid X Receptor Ligands: Differential Biological Activities of Individual Antipodes", J. Med. Chem. 44, 2298-2303 (2001).
Wagner, et al., "Modeling, synthesis and biological evaluation of potential retinoid X receptor (RXR) selective agonists: novel analogues of 4-[1-(3,5,5,8,8-pentamethyl-5,6,7,8-tetrahydro-2-naphthyl)ethynyl]benzoic acid (bexarotene).", J Med Chem 52(19), 5950-5966 (2009).
Wallen-Mackenzie, et al., "Nurr1-RXR heterodimers mediate RXR ligand-induced signaling in neuronal cells", Genes & Development 17, 3036-3047 (2003).
Wang, et al., "IL-6 Mediates Macrophage Infiltration after Irradiation via Up-regulation of CCL2/CCL5 in Non-small Cell Lung Cancer", Radiat Res 187(1), 50-59 (2017).
Wang, et al., "Structure and function ofNurr1 identifies a class of ligand-independent nuclear receptors", Nature 423, 555-560 (2003).
Wang, et al., "Up regulation of IL-6 is involved in di (2-ethylhexyl) phthalate (DEHP) induced migration and invasion of non small cell lung cancer (NSCLC) cells", Biomed Pharmacother 89, 1037-1044 (2017).
White, et al., "Identification of the retinoic acid-inducible all-trans-retinoic acid 4-hydroxylase.", Journal of Biological Chemistry 271, 29922-29927 (1996).
Whitworth, et al., "The impact of novel retinoids in combination with platinum chemotherapy on ovarian cancer stem cells", Gynecologic Oncology 125, 226-230 (2012).
Winum, et al., "Synthesis of New Targretin® Analogues that Induce Apoptosis in Leukemia HL-60 Cells.", Bioorg Med Chem Lett 12, 3529-3532 (2002).
Wojcik, et al., "IL-6 and VEGF in small cell lung cancer patients", Anticancer Res 30(5), 1773-1778 (2010).
Wu, et al., "An intermittent approach for cancer chemoprevention", Nat Rev Cancer 11(12), 879-885 (2011).
Wu, et al., "The retinoid X receptor-selective retinoid, LGD1069, prevents the development of estrogen receptor-negative mammary tumors in transgenic mice", Cancer Res 62(22), 6376-6380 (2002).
Yamauchi, et al., "Inhibition of RXR and PPARgamma ameliorate diet-induced obesity and type 2 diabetes", J. Clin. Invest. 108, 1001-1013 (2001).
Yen, et al., "A selective retinoid X receptor agonist bexarotene (Targretin) prevents and overcomes acquired paclitaxel (Taxol) resistance in human non-small cell lung cancer", Clinical Cancer Research 10(24), 8656-8664 (2004).
Yen, et al., "A Selective Retinoid X Receptor Agonist Bexarotene (Targretin) Prevents and Overcomes Acquired Paclitaxel (Taxol) Resistance in Human Non-Small Cell Lung Cancer.", British Journal of Cancer 94, 654-660 (2006).
Yen, et al., "Synergistic effect of a retinoid X receptor-selective ligand bexarotene (LGD1069, Targretin) and paclitaxel (Taxol) in mammary carcinoma", Breast Cancer Res. Treat. 88, 141-148 (2004).
Yeo, et al., "Chemopreventive effect of phosphodieasterase-4 inhibition in benzo(a)pyrene-induced murine lung cancer model", Exp Lung Res 40(10), 500-506 (2014).
You, et al., "Activation of the Ki-ras protooncogene in spontaneously occurring and chemically induced lung tumors of the strain A mouse", Proc Natl Acad Sci USA 86(9), 3070-3074 (1989).
Zacheis, et al., "Heteroarotinoids Inhibit Head and Neck Cancer Cell Lines in Vitro and in Vivo Through Both RAR and RXR Retinoic Acid Receiptors", J Med Chem 42, 4434-4445 (1999).
Zaynagetdinov, et al., "A critical role for macrophages in promotion of urethane-induced lung carcinogenesis", J Immunol 187(11), 5703-5711 (2011).
Zetterstrom, et al., "Dopamine neuronagenesis in Nurr1-deficient mice", Science 276, 248-250 (1997).
Zhang, et al., "Aerosolized bexarotene inhibits lung tumorigenesis without increasing plasma triglyceride and cholesterol levels in mice", Cancer Prev Res (Phila) 4(2), 270-276 (2011, epub 2010).
Zhang, et al., "Induction of Apoptosis by Bexarotene in Cutaneous T-Cell Lymphoma Cells.", Clin Cancer Res 8, 1234-1240 (2002).
Zhang, et al., "Syntheses of isotopically labeled 4-[1-(3,5,5,8,8-pentamethyl-5,6,7,8-tetrahydro-2-naphthyl)ethenyl]benzoic acid (LGD1069), a potent retinoid x receptor-selective ligand", Journal of Labelled Compounds and Radiopharmaceuticals 36(7), 701-712 (1995).
Zimmermann, et al., "A yeast strain for simultaneous detection of mitotic crossing over, mitotic gene conversion, and reverse mutation", Mutat. Res. 28, 381-388, (1975).
Zimmermann, "Procedures used in the induction of mitotic recombination and mutation in the yeast *Saccharomyeces cerevisiae*", Mutat. Res. 31, 71-86 (1975).

\* cited by examiner

DIHYDROINDENE AND TETRAHYDRONAPHTHALENE COMPOUNDS

PRIORITY OF INVENTION

This application claims priority to U.S. Provisional Application No. 62/449,501, filed 23 Jan. 2017. The entire content of this provisional application is hereby incorporated herein by reference.

GOVERNMENT FUNDING

This invention was made with government support under R15 CA139364 awarded by the National Institutes of Health. The government has certain rights in the invention.

BACKGROUND OF THE INVENTION

The human retinoid X receptors (hRXRs) consist of three identified isoforms (α, β, γ) that function as transcription promoters often in partnership with other members of a larger nuclear receptor (NR) family of transcription regulators including the thyroid receptor (TR), the vitamin D receptor (VDR), the liver X receptor (LXR), the peroxisome proliferator-activated receptor (PPAR), and the retinoic acid receptor (RAR). While 9-cis-retinoic acid (9-cis-RA) and docosahexaenoic acid (DHA) have been shown to bind to hRXRs and promote RXR element (RXRE) regulated transcription (i.e. function as RXR agonists), it is still unclear if RXR has a bona fide endogenous molecular ligand. RXR has been described as the central NR regulator, because it often plays a critical role, either as a permissive or non-permissive partner, in heterodimer complexes that must be formed with the other NRs to regulate their respective response elements.

Recent studies have identified several RXR-selective-binding molecular ligands (rexinoids) that can modulate not only RXRE regulated transcription but also the heterodimer regulated transcription of other NRs. For instance, RXR is a subordinate partner in the RXR-RAR heterodimer, otherwise referred to as a non-permissive heterodimer, since transcription is not promoted in the RAR unliganded (apo-RAR) heterodimer with RXR. Additionally, the RXR-TR heterodimer is non-permissive. In contrast to these non-permissive heterodimers, permissive heterodimers such as RXR-PPAR allow transcription to be promoted in the presence of either RXR or PPAR agonists. The RXR-LXR heterodimer is also permissive. Hence, there is enormous potential for RXR agonists to activate or repress various biological pathways and effect therapeutic results for various conditions that would benefit from activation or repression of a specific pathway.

Six rexinoids described in the literature include Bexarotene (60), CD3254 (61), LGD100268 (62), a pyridyl-bexarotene analog (1), an unsaturated bexarotene analog (2), and the mono-fluorinated bexarotene analog (3).

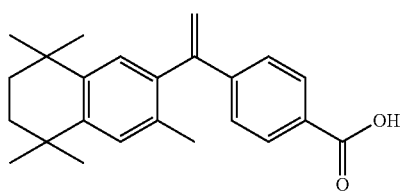

Bexarontene

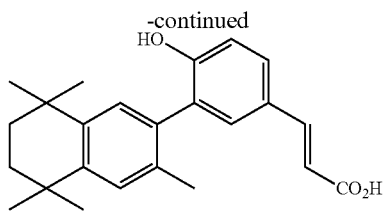

CD 3254

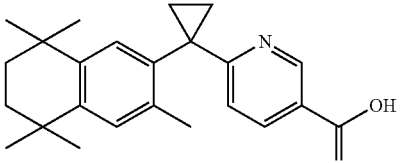

LGD100268

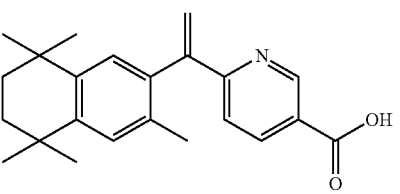

1

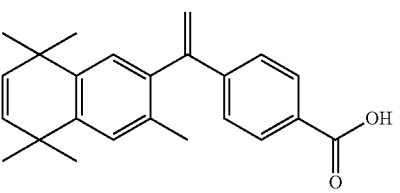

2

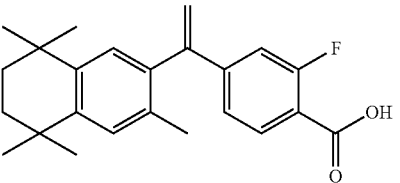

3

Bexarotene has been documented to have an $EC_{50}$ of 33, 24 and 25 nm for the RXR α,β,γ subtypes, respectively, and a $K_d$ of 14, 21, and 29 nm for the RXR α,β,γ subtypes, respectively, in a CV-1 cell line (Boehm, M. F., et al., "Synthesis and Structure-Activity Relationships of Novel Retinoid X Receptor-Selective Retinoids" *J. Med. Chem.* 1994, 37, 2930-2941). CD3254 appears to have an $EC_{50}$ on the order of 10 nm for the hRXRβ isoform (Santin, E. P., et al., "Modulating Retinoid X Receptor with a Series of (E)-3-[4-Hydroxy-3-(3-alkoxy-5,5,8,8-tetramethyl-5,6,7,8-tetrahydronaphthalen-2-yl)phenyl]acrylic Acids and Their 4-Alkoxy Isomers" *J. Med. Chem.* 2009, 52, 3150-3158). LGD100268 and 1 have been documented to have $EC_{50}$s of 4, 3, and 4 nm and 6, 9, and 5 nm for the RXR α,β,γ subtypes, respectively, and $K_d$s of 3, 3, and 3 nm and 22, 61, and 39 nm for the RXR α,β,γ subtypes, respectively, in a CV-1 cell line (Boehm, M. F., et al., "Design and Synthesis of Potent Retinoid X Receptor Selective Ligands That Induce Apoptosis in Leukemia Cells" *J. Med. Chem.* 1995, 38, 3146-3155). While the unsaturated-bexarotene analog (2) has been reported, its ability to serve as an RXR agonist has not been published. Finally, the mono-fluorinated bexarotene analog (3) has an $EC_{50}$ of 43 nm and a $K_d$ of 12 nm in hRXR in Caco-2 cells (Wagner, C. E., et al., "Modeling, Synthesis and Biological Evaluation of Potential Retinoid X Receptor (RXR) Selective Agonists: Novel Analogues of 4-[1-(3,5,5,8,8-Pentamethyl-5,6,7,8-tetrahydro-2-naphthyl) ethynyl]benzoic Acid (Bexarotene)" *J. Med. Chem.* 2009, 52, 5950-5966).

Currently there is a need for additional chemical agents that are useful for treating or preventing cancer or treating or preventing Alzheimer's disease. There is also a need for anti-cancer or anti-Alzheimer's agents that have enhanced activity or that have improved pharmacologic properties such as increased solubility or better bioavailability.

Additionally, studies suggest that the retinoid X receptor pathway is associated with CNS remyelination processes (see M. Natrajan, et al., *Brain*, 2015, 1-17; and J. K. Huang et al., *Nature Neuroscience*, 2010, 1). Currently there is a need for additional chemical agents that are useful for treating conditions associated with demyelination, such as, for example, multiple sclerosis.

SUMMARY OF THE INVENTION

This invention provides compounds for treating cancers, Alzheimer's disease, or conditions associated with demyelination.

Accordingly in one embodiment the invention provides a compound of invention which is a compound of formula I:

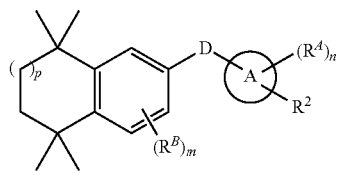

wherein:
p is 0 and D is

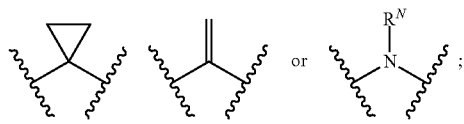

or p is 1 and D is

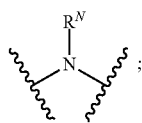

$R^N$ is $(C_1\text{-}C_6)$alkyl, $(C_3\text{-}C_6)$cycloalkyl, $(C_2\text{-}C_6)$alkenyl, or $(C_2\text{-}C_6)$alkynyl, wherein the $(C_1\text{-}C_6)$alkyl, $(C_3\text{-}C_6)$cycloalkyl, $(C_2\text{-}C_6)$alkenyl, and $(C_2\text{-}C_6)$alkynyl are optionally substituted with one or more groups independently selected from halo, hydroxy, nitro, cyano, and oxo (=O);

$R^2$ is —COOH, —B(OH)$_2$, or —SO$_3$H;

ring A is phenyl or 6-membered heteroaryl;

each $R^4$ is independently selected from the group consisting of halo, hydroxy, cyano, nitro, $(C_1\text{-}C_6)$alkyl, $(C_3\text{-}C_6)$cycloalkyl, $(C_2\text{-}C_6)$alkenyl, $(C_2\text{-}C_6)$alkynyl, $(C_1\text{-}C_6)$alkoxy, $(C_1\text{-}C_6)$alkoxycarbonyl, and $(C_1\text{-}C_6)$alkanoyloxy, wherein the $(C_1\text{-}C_6)$alkyl, $(C_3\text{-}C_6)$cycloalkyl, $(C_2\text{-}C_6)$alkenyl, $(C_2\text{-}C_6)$alkynyl, $(C_1\text{-}C_6)$alkoxy, $(C_1\text{-}C_6)$alkoxycarbonyl, and $(C_1\text{-}C_6)$alkanoyloxy are optionally substituted with one or more groups independently selected from halo, hydroxy, nitro, cyano, $(C_1\text{-}C_6)$alkoxy, and oxo (=O);

each $R^B$ is independently selected from the group consisting of halo, hydroxy, cyano, nitro, $(C_1\text{-}C_6)$alkyl, $(C_3\text{-}C_6)$cycloalkyl, $(C_2\text{-}C_6)$alkenyl, $(C_2\text{-}C_6)$alkynyl, $(C_1\text{-}C_6)$alkoxy, $(C_1\text{-}C_6)$alkoxycarbonyl, and $(C_1\text{-}C_6)$alkanoyloxy, wherein the $(C_1\text{-}C_6)$alkyl, $(C_3\text{-}C_6)$cycloalkyl, $(C_2\text{-}C_6)$alkenyl, $(C_2\text{-}C_6)$alkynyl, $(C_1\text{-}C_6)$alkoxy, $(C_1\text{-}C_6)$alkoxycarbonyl, and $(C_1\text{-}C_6)$alkanoyloxy are optionally substituted with one or more groups independently selected from halo, hydroxy, nitro, cyano, $(C_1\text{-}C_6)$alkoxy, and oxo (=O);

n is 0, 1, 2, 3, or 4; and
m is 0, 1, 2, 3, or 4;
or a salt thereof;
provided that the compound is not

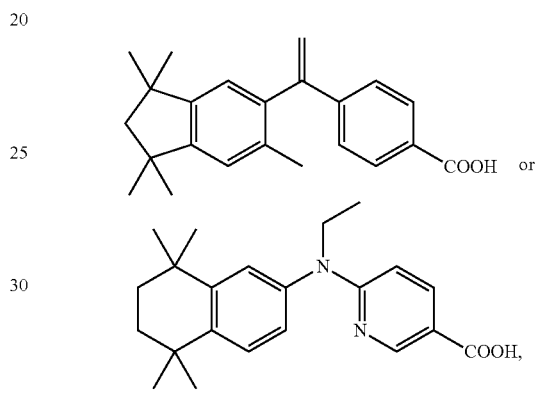

or a salt thereof.

The invention also provides a pharmaceutical composition comprising a compound of the invention, or a pharmaceutically acceptable salt thereof, in combination with a pharmaceutically acceptable diluent or carrier.

The invention also provides a method for inhibiting cancer cell (e.g., glioblastoma multiforme, breast, lung, colon, pancreatic, skin, cutaneous T-cell lymphoma, acute promyelocytic leukemia, ovarian, bladder, kidney, and head and neck cancers, and Kaposi's sarcoma), growth comprising contacting the cell in vitro or in vivo with an effective amount of a compound of the invention, or a salt thereof. The off-label use of bexarotene, a known RXR agonist, and retinoids in other cancers is currently being researched.

The invention also provides a method for treating cancer (e.g., glioblastoma multiforme, breast, lung, colon, pancreatic, skin, cutaneous T-cell lymphoma, acute promyelocytic leukemia, ovarian, bladder, kidney, and head and neck cancers, and Kaposi's sarcoma) in a mammal (e.g. a human) comprising administering to the mammal an effective amount of a compound of the invention, or a pharmaceutically acceptable salt thereof.

The invention also provides a method for treating cancer (e.g., glioblastoma multiforme, breast, lung, colon, pancreatic, skin, cutaneous T-cell lymphoma, acute promyelocytic leukemia, ovarian, bladder, kidney, and head and neck cancers, and Kaposi's sarcoma) in a mammal (e.g. a human) in need of such treatment comprising administering to the mammal an effective amount of a compound of the invention, or a pharmaceutically acceptable salt thereof.

The invention also provides a method for treating cancer (e.g., glioblastoma multiforme, breast, lung, colon, pancreatic, skin, cutaneous T-cell lymphoma, acute promyelocytic leukemia, ovarian, bladder, kidney, and head and neck cancers, and Kaposi's sarcoma) in a mammal (e.g. a human) diagnosed with cancer comprising administering to the mammal an effective amount of a compound of the invention, or a pharmaceutically acceptable salt thereof.

The invention also provides a method for activating RXR in a cell comprising contacting the cell in vitro or in vivo with an effective amount of a compound of the invention, or a salt thereof.

The invention also provides a compound of the invention, or a pharmaceutically acceptable salt thereof, for use in medical therapy.

The invention also provides a compound of the invention, or a pharmaceutically acceptable salt thereof, for the manufacture of a medicament useful for the treatment of cancer (e.g., glioblastoma multiforme, breast, lung, colon, pancreatic, skin, cutaneous T-cell lymphoma, acute promyelocytic leukemia, ovarian, bladder, kidney, and head and neck cancers, and Kaposi's sarcoma) in a mammal (e.g. a human).

The invention also provides a compound of the invention, or a pharmaceutically acceptable salt thereof, for use in the prophylactic or therapeutic treatment of cancer (e.g., glioblastoma multiforme, breast, lung, colon, pancreatic, skin, cutaneous T-cell lymphoma, acute promyelocytic leukemia, ovarian, bladder, kidney, and head and neck cancers, and Kaposi's sarcoma) in a mammal.

The invention also provides a method for treating Alzheimer's disease in a human comprising administering to the human an effective amount of compound of the invention, or a pharmaceutically acceptable salt thereof.

The invention also provides a method for treating Alzheimer's disease in a human in need of such treatment comprising administering to the human an effective amount of compound of the invention, or a pharmaceutically acceptable salt thereof.

The invention also provides a method for treating Alzheimer's disease in a human diagnosed with Alzheimer's disease comprising administering to the human an effective amount of compound of the invention, or a pharmaceutically acceptable salt thereof.

The invention also provides a compound of the invention, or a pharmaceutically acceptable salt thereof, for the manufacture of a medicament useful for the treatment of Alzheimer's disease in a human.

The invention also provides a compound of the invention, or a pharmaceutically acceptable salt thereof, for use in the prophylactic or therapeutic treatment of Alzheimer's disease in a human.

The invention also provides a method for treating a disease associated with demyelination in a human comprising administering to the human an effective amount of compound of the invention, or a pharmaceutically acceptable salt thereof.

The invention also provides processes and novel intermediates that are useful for preparing the compounds of the invention.

DETAILED DESCRIPTION

Figures 1A, 1B, 1C:
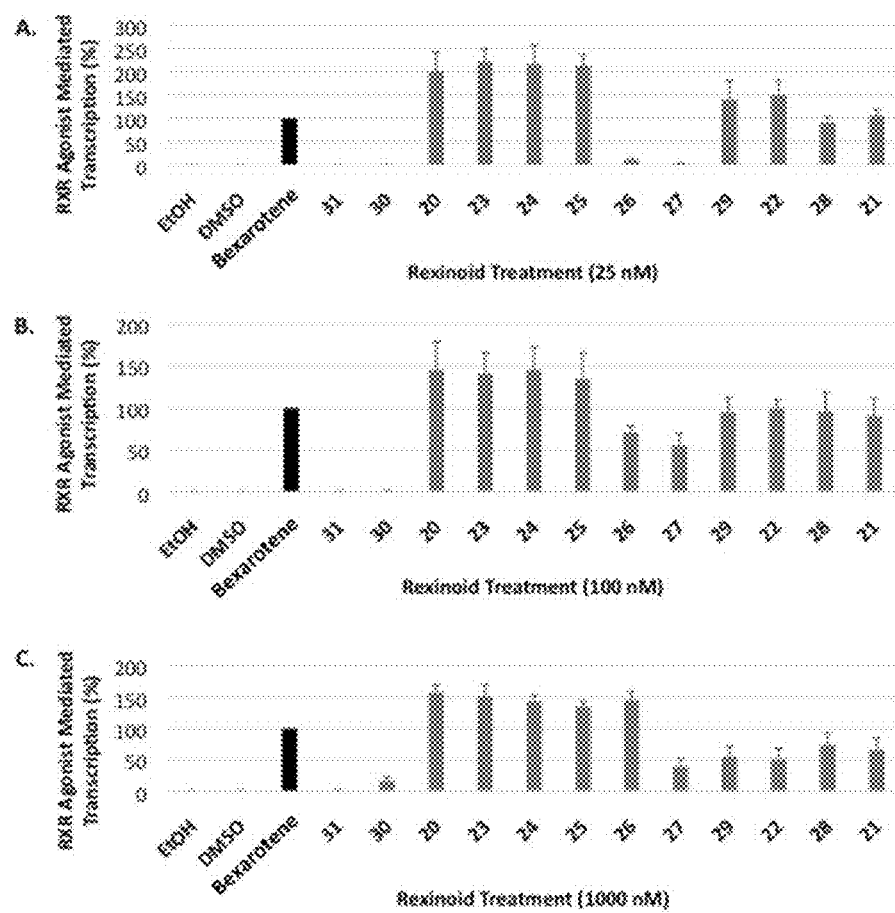
FIGS. 1A-1C show data for representative compounds from Test A below.

The term "activating", such as used in the phrase "activating RXR", means to promote transcriptional activity.

The term "treatment" or "treating," to the extent it relates to a disease or condition includes preventing the disease or condition from occurring, inhibiting the disease or condition, eliminating the disease or condition, and/or relieving one or more symptoms of the disease or condition.

The term "alkyl", by itself or as part of another substituent, means, unless otherwise stated, a straight or branched chain hydrocarbon radical, having the number of carbon atoms designated.

The term "alkenyl" refers to an unsaturated alkyl radical having one or more double bonds. Similarly, the term "alkynyl" refers to an unsaturated alkyl radical having one or more triple bonds.

The term "alkoxy" refers to an alkyl groups attached to the remainder of the molecule via an oxygen atom ("oxy").

The term "cycloalkyl" refers to a saturated all carbon ring having 3 to 6 carbon atoms (i.e., ($C_3$-$C_6$)carbocycle).

The term "6-membered heteroaryl ring" includes single aromatic rings with at least two carbon atoms and 1, 2, 3, or 4 heteroatoms selected from N, O or S.

Specifically, ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)alkanoyl can be acetyl, propanoyl or butanoyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkanoyloxy can be formyloxy, acetoxy, propanoyloxy, butanoyloxy, isobutanoyloxy, pentanoyloxy, or hexanoyloxy; and heteroaryl can be pyrazinyl, pyridazine, triazine, pyridyl, or pyrimidinyl, or an N-oxide thereof.

In one embodiment, the invention provides a compound of formula I, which is a compound of formula Ia:

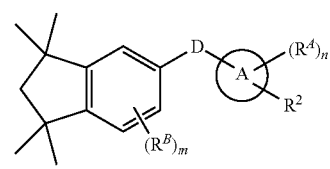

Ia or a salt thereof.

In one embodiment, the invention provides a compound of formula I which is a compound of formula Ib:

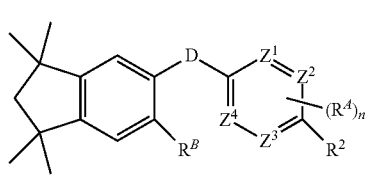

Ib wherein:
Z$^1$ is N or CH;
Z$^2$ is N or CH;
Z$^3$ is N or CH; and
Z$^4$ is N or CH;
or a salt thereof.

In one embodiment, the invention provides a compound of formula I which is a compound of formula Ic:

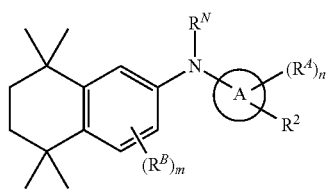

or a salt thereof.

In one embodiment, the invention provides a compound of formula I which is a compound of formula Id:

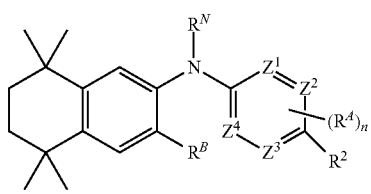

wherein:
Z$^1$ is N or CH;
Z$^2$ is N or CH;
Z$^3$ is N or CH; and
Z$^4$ is N or CH;
or a salt thereof.

In one embodiment, D is

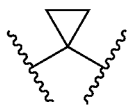

In one embodiment, D is

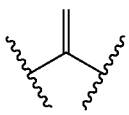

In one embodiment, D is

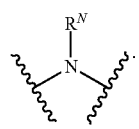

In one embodiment, R$^N$ is (C$_1$-C$_6$)alkyl that is optionally substituted with one or more groups independently selected from halo, hydroxy, nitro, cyano, and oxo (=O).

In one embodiment, R$^N$ is ethyl.

In one embodiment, R$^2$ is —COOH.

In one embodiment, ring A is 6-membered heteroaryl comprising 1 to 3 nitrogen atoms.

In one embodiment, ring A is

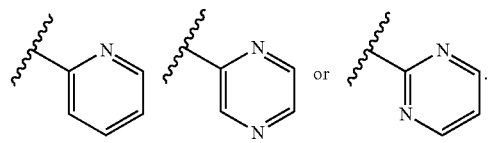

In one embodiment, ring A is phenyl.

In one embodiment, R$^A$ is —F.

In one embodiment, R$^B$ is (C$_1$-C$_6$)alkyl that is optionally substituted with one or more groups independently selected from halo, hydroxy, nitro, cyano, and oxo (=O).

In one embodiment, R$^B$ is methyl.

In one embodiment, n is 0 or 1.

In one embodiment, p is 0;

D is

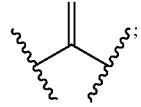

and ring A is not phenyl.

In one embodiment, the compound of invention is selected from the group consisting of:

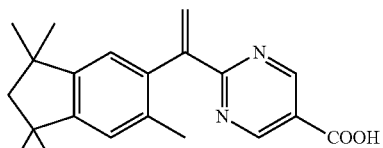

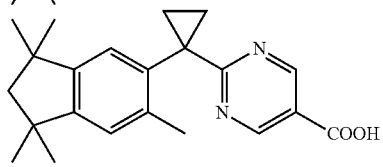

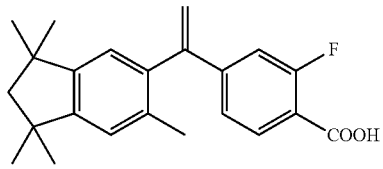

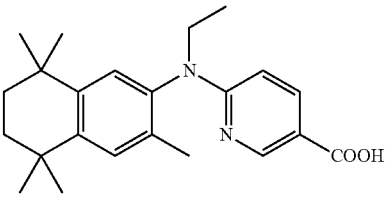

-continued
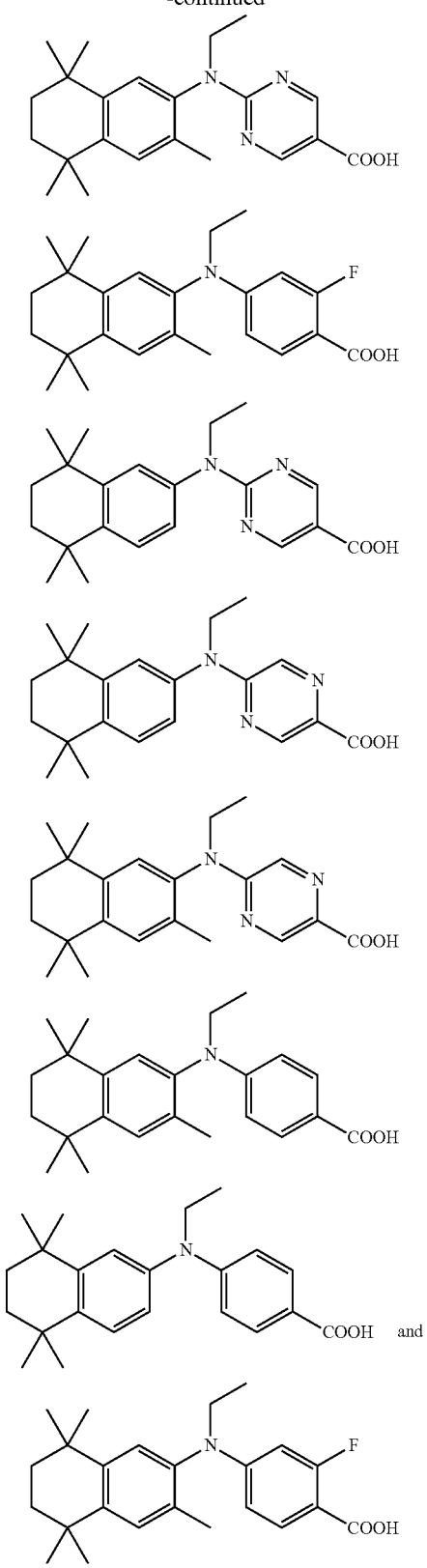
and salts thereof.
In one embodiment, the compound of invention is selected from the group consisting of:
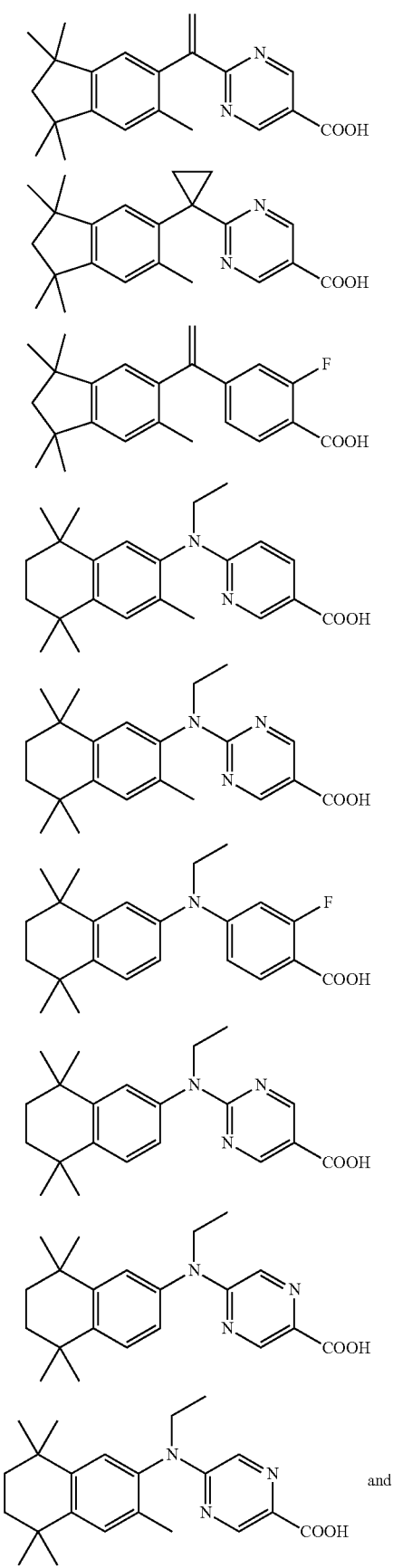
and -continued
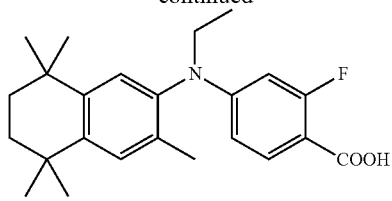
and salts thereof.
In one embodiment, the invention also provides a compound of invention that is selected from the group consisting of:
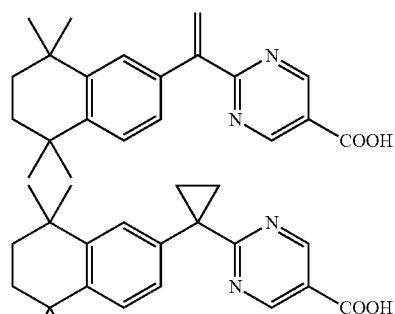
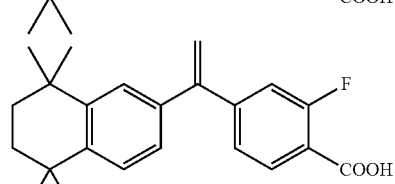
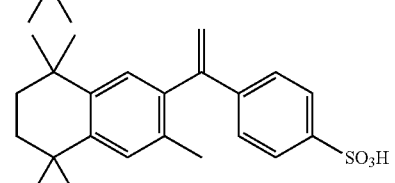
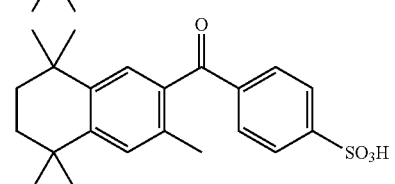
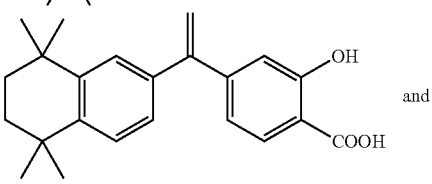
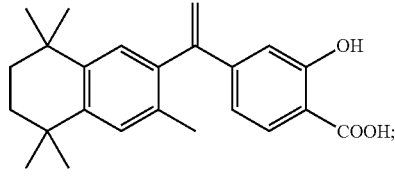
and salts thereof.
In one embodiment, the invention also provides a compound of invention that is selected from the group consisting of:
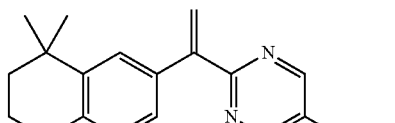
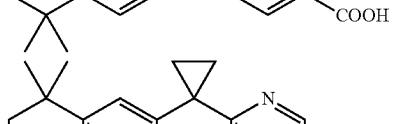
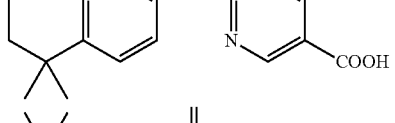
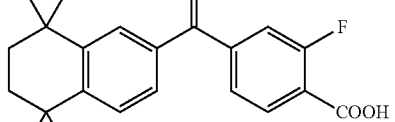
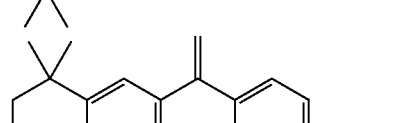
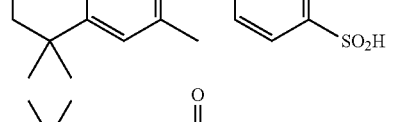
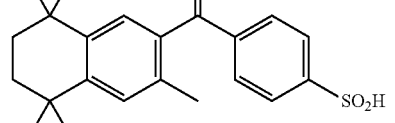
and salts thereof.
In one embodiment, the compound of invention is not:
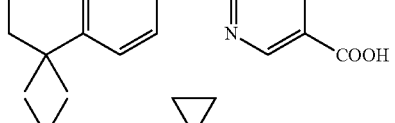
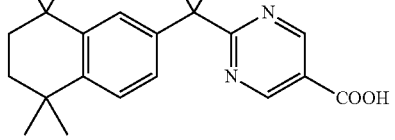

-continued

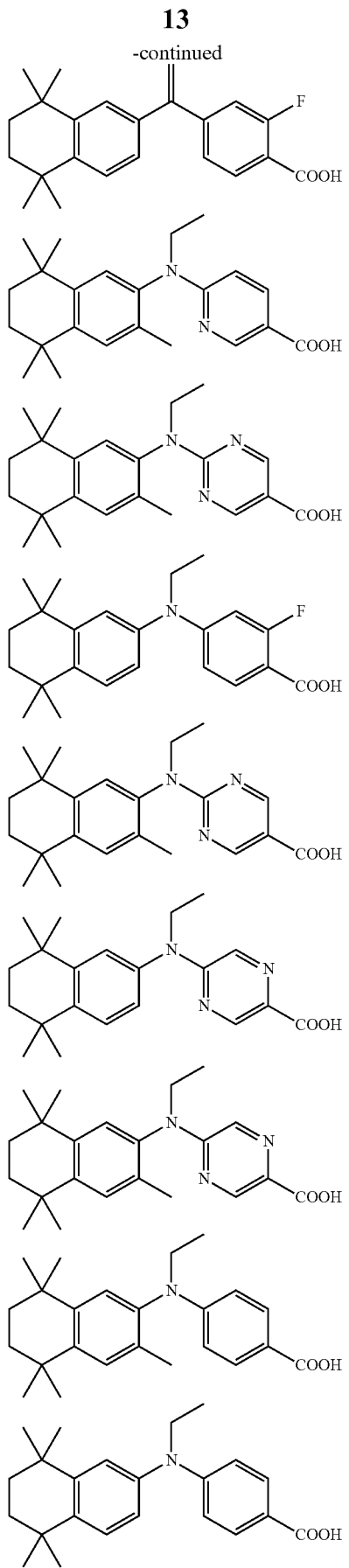

-continued

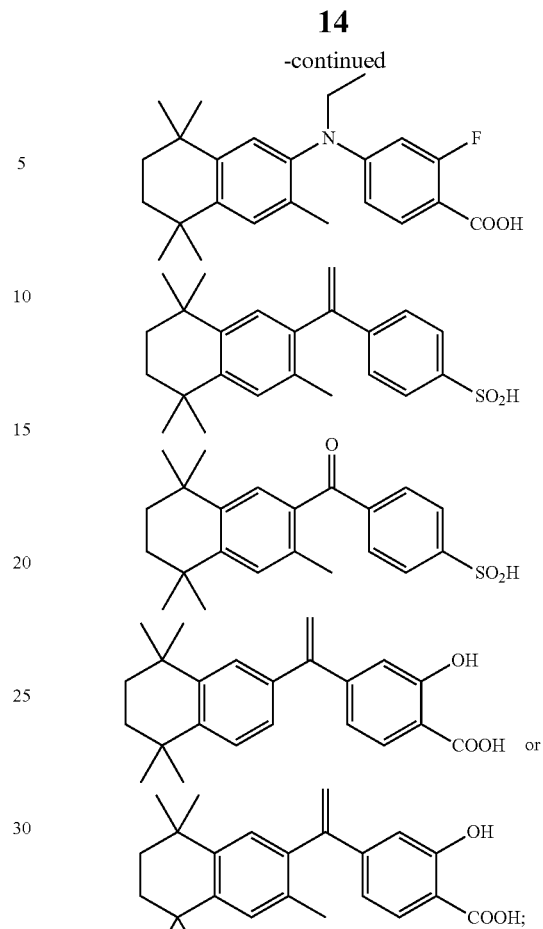

or a salt thereof.

In one embodiment, the invention provides a compound of formula I, which is a compound of formula Ic:

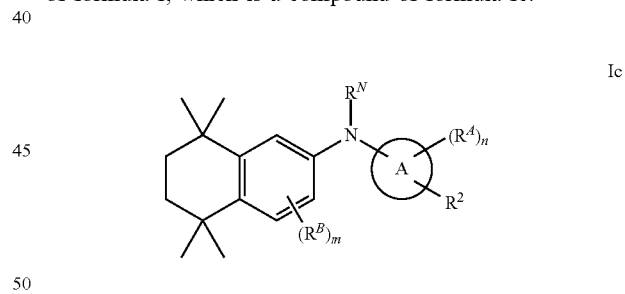

Ic wherein each $R^A$ is independently selected from the group consisting of hydroxy, cyano, nitro, ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_1$-$C_6$)alkoxycarbonyl, and ($C_1$-$C_6$)alkanoyloxy, wherein the ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_1$-$C_6$)alkoxycarbonyl, and ($C_1$-$C_6$)alkanoyloxy are optionally substituted with one or more groups independently selected from halo, hydroxy, nitro, cyano, ($C_1$-$C_6$)alkoxy, and oxo (=O); and n is 1, 2, or 3.

In cases where compounds are sufficiently basic or acidic, a salt of a compound of the invention can be useful as an intermediate for isolating or purifying a compound of the invention. Additionally, administration of a compound of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949. Compounds that are non-toxic and non-mutagenic at typical dose levels will have useful doses. (Mortelmans, K.; Zeiger, E. "The Ames Salmonella/microsome mutagenicity assay." Mutat. Res. 2000, 455, 29-60.)

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents. In certain embodiments, compounds of the invention can be administered in combination with agents that are useful for the treatment of breast cancer. (Yen, W. et al. "Synergistic effect of a retinoid X receptor-selective ligand bexarotene (LGD1069, Targretin) and paclitaxel (Taxol) in mammary carcinoma" Breast Cancer Research and Treatment, 2004, 88, 141-148.) In certain embodiments, compounds of the invention can be administered in combination with agents that are useful for the treatment of lung cancer. (Yen, W.-C.; Corpuz, M. R.; Prudente, R. Y.; Cooke, T. A.; Bissonnette, R. P.; Negro-Vilar, A.; Lamph, W. W. "A Selective Retinoid X Receptor Agonist Bexarotene (Targretin) Prevents and Overcomes Acquired Paclitaxel (Taxol) Resistance in Human Non-Small Cell Lung Cancer." Clin. Cancer Res. 2004, 10, 8656-8664.). In certain embodiments, compounds of the invention can be administered in combination with agents that are useful for the treatment of glioblastoma multiforme. (Heo, J., et al., *Clin Exp Metastasis*, 2016, 33, 417-429) In certain embodiments, compounds of the invention can be administered in combination with agents that are useful for the treatment of diabetes. (Mukherjee, R.; Davies, P. J. A.; Crombie, D. L.; Bischoff, E. D.; Cesario, R. M.; Jow, L.; Hamanns, L. G.; Boehm, M. F.; Mondon, C. E.; Nadzan, A. M.; Paterniti, J. R.; Heyman, R. A. "Sensitization of diabetic and obese mice to insulin by retinoid X receptor agonists." Nature 1997, 386, 407-410.) Accordingly, in one embodiment the invention also provides a composition comprising a compound of the invention, or a pharmaceutically acceptable salt thereof, at least one other therapeutic agent, and a pharmaceutically acceptable diluent or carrier. The invention also provides a kit comprising a compound of the invention, or a pharmaceutically acceptable salt thereof, at least one other therapeutic agent, packaging material, and instructions for administering the compound of the invention or the pharmaceutically acceptable salt thereof and the other therapeutic agent or agents to an animal to treat cancer or diabetes.

The ability of a compound of the invention to act as an RXR agonist (e.g. to promote or activate RXR, i.e., promote or activate RXR regulated gene expression) may be determined using pharmacological models which are well known to the art, or using Test A or Test B described below.

Test A. RXR Selective Agonist Assay (Mammalian Two-Hybrid Assay).

Representative compounds were tested for RXR selective agonist activity via a mammalian two-hybrid assay in human colon cancer cells, HCT-116. The cell line was transfected with pCMVhRXR binding domain vector (BD), hRXR activation domain (AD), pFR-Luc reporter gene containing BD-binding sites, and a renilla control plasmid. Cells were transfected for 24 hours utilizing a liposome-mediated transfection protocol then exposed to either ethanol vehicle or compound at 25 nM (FIG. 1A), 100 nM (FIG. 1B), 1000 nM (FIG. 1C). After 24 hours the cells were lysed and a luciferase assay was completed. Analog dependent RXR binding and homodimerization, as measured by luciferase output, was compared to bexarotene (see FIGS. 1A-1C). These results demonstrate that representative compounds of the invention are RXR agonists. Accordingly, compounds of the invention may be useful as therapeutic agents for the treatment of cancer or Alzheimer's disease. Such cancers include but are not limited to, colon, glioblastoma multiforme, breast, lung, pancreatic, skin, cutaneous T-cell lymphoma, acute promyelocytic leukemia, ovarian, bladder, kidney, and head and neck cancers, and Kaposi's sarcoma. Additionally, compounds of the invention may be useful as pharmacological tools for the further investigation of RXR function.

Test B. RXR Agonist Assay (RXRE-Luciferase Based Assay).

Figures 2A, 2B, 2C:
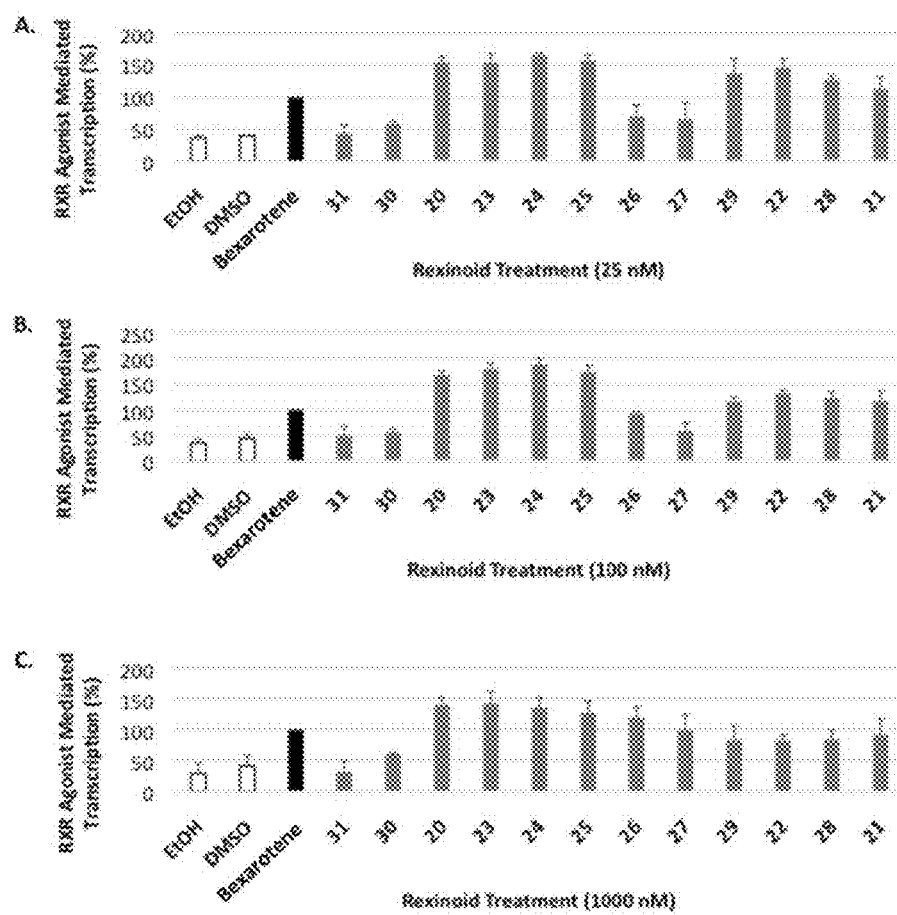
FIGS. 2A-2C show data for representative compounds from Test B below.

Representative compounds were tested for RXR agonist activity via an RXRE-luciferase based system utilizing human colon cancer cells HCT-116. The cell line was transfected with hRXRα, an RXRE luciferase reporter gene, renilla control plasmid, and carrier DNA (pTZ18U). Cells were transfected for 24 hours utilizing a liposome-mediated transfection protocol then exposed to either ethanol vehicle or compound at 25 nM (FIG. 2A), 100 nM (FIG. 2B), 1000 nM (FIG. 2C). After 24 hours the cells were lysed and a luciferase assay was completed. Analog dependent, RXR-mediated transcription, as measured by luciferase output, was compared to bexarotene (see FIGS. 2A-2C).

These results demonstrate that compounds of the invention are RXR agonists. Accordingly compounds of the invention may be useful as therapeutic agents for the treatment of cancer or Alzheimer's disease. Such cancers include but are not limited to, glioblastoma multiforme, breast, lung, colon, pancreatic, skin, cutaneous T-cell lymphoma, acute promyelocytic leukemia, ovarian, bladder, kidney, and head and neck cancers, and Kaposi's sarcoma. Additionally, compounds of the invention may be useful as pharmacological tools for the further investigation of RXR function.

Compounds of invention can be prepared using known methods or using procedures analogous to those described in the examples herein. For example, compounds of invention can be prepared as illustrated in the following schemes.

Scheme 1
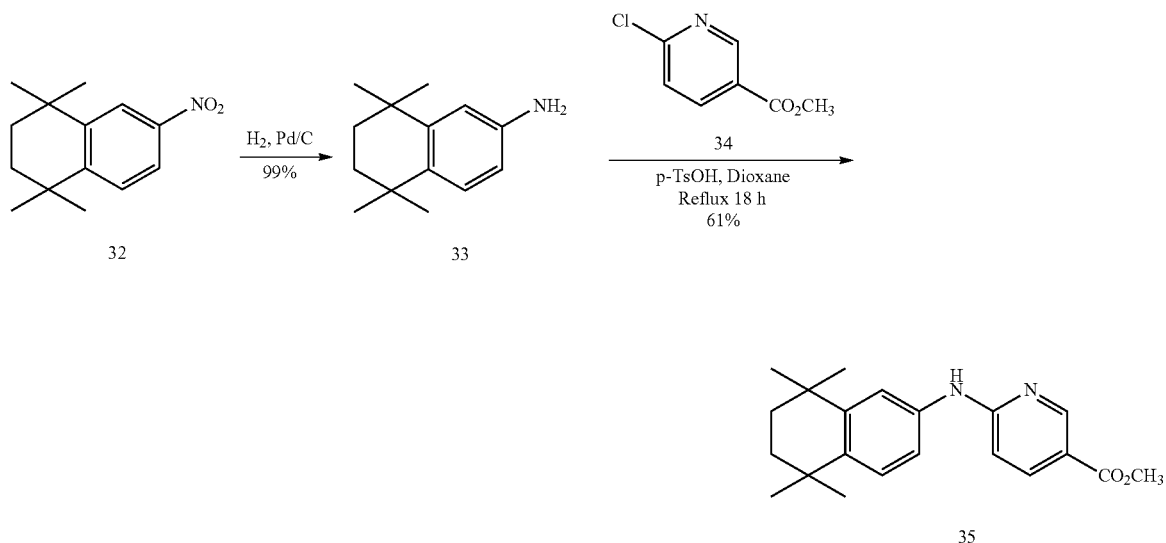
Scheme 2
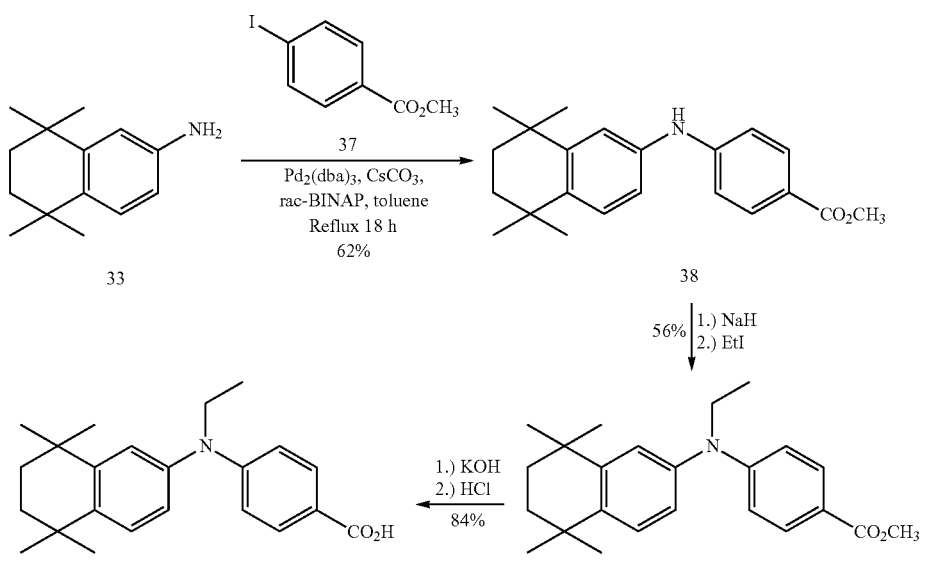

Scheme 3
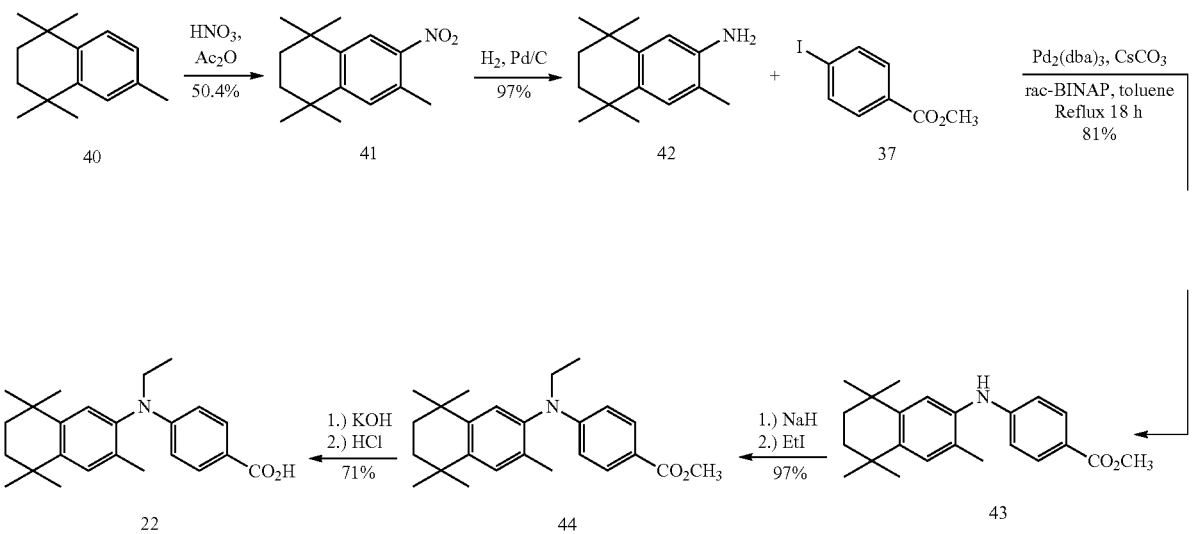
Scheme 4
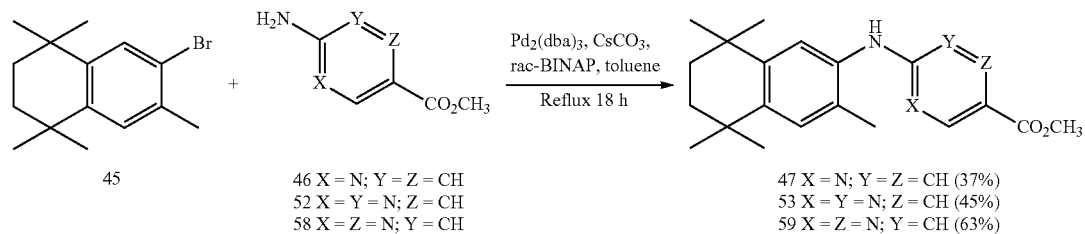
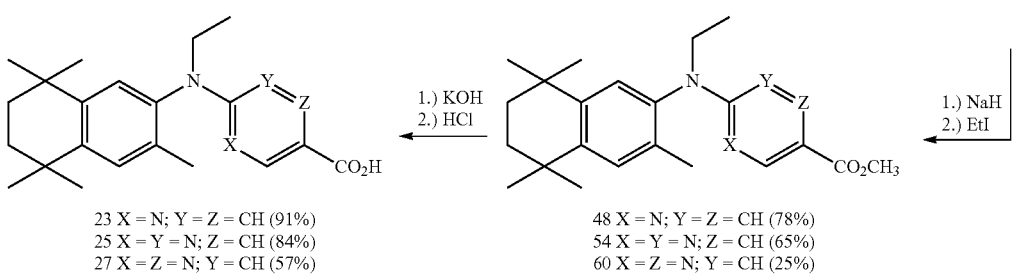
Scheme 5
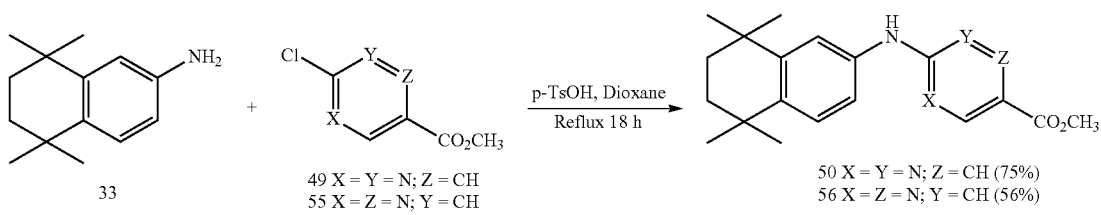

-continued

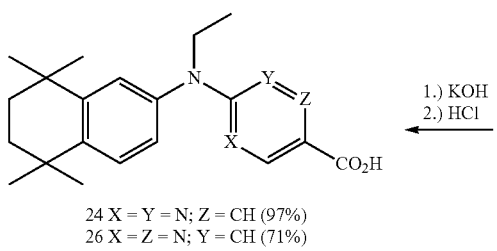

24 X = Y = N; Z = CH (97%)
26 X = Z = N; Y = CH (71%)

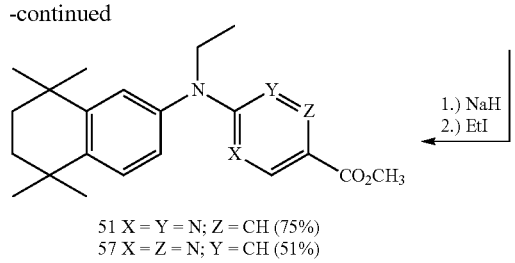

51 X = Y = N; Z = CH (75%)
57 X = Z = N; Y = CH (51%)

Scheme 6

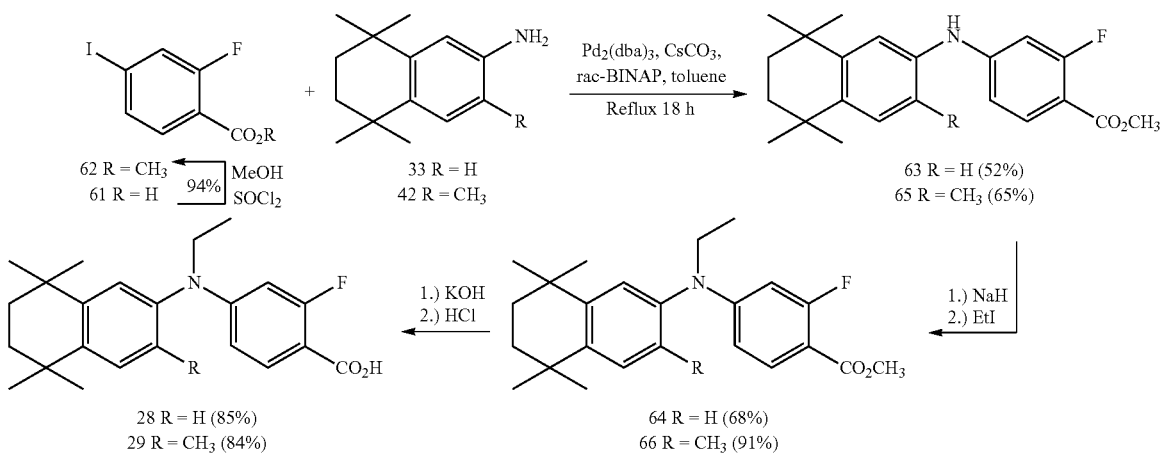

62 R = CH₃
61 R = H   MeOH / SOCl₂  94%

33 R = H
42 R = CH₃

63 R = H (52%)
65 R = CH₃ (65%)

28 R = H (85%)
29 R = CH₃ (84%)

64 R = H (68%)
66 R = CH₃ (91%)

The invention will now be illustrated by the following non-limiting Examples.

EXAMPLES

Example 1. 6-(ethyl(5,5,8,8-tetramethyl-5,6,7,8-tetrahydronaphthalen-2-yl)amino)nicotinic acid (20)

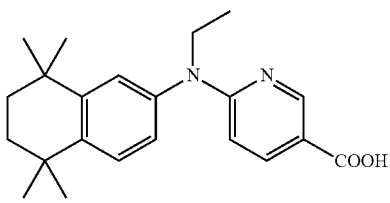 [SMILES: CCN(c1ccc2c(c1)C(C)(C)CCC2(C)C)c1ccc(C(=O)O)cn1]

To a 100 mL round-bottomed flask equipped with a stir bar and charged with methyl ester 36 (0.3674 g, 1.002 mmol) suspended in methanol (3.5 mL) was added a solution of potassium hydroxide (0.1767 g, 3.15 mmol) in water (0.22 mL). This reaction was stirred at reflux in an oil bath at 87° C. for 1 hour. The reaction was then cooled to room temperature and acidified with 20% HCl (52 mL). The crude white precipitate was filtered and washed with cold water to provide crude compound 20 (0.3238 g, 91%) and this crude material was purified by column chromatography (25 mL SiO₂, 30% ethyl acetate:hexanes to pure ethyl acetate to 2% methanol:ethyl acetate) to give compound 20 (0.2677 g, 76%) as a white crystalline solid, m.p. 230-232° C. (lit. 235.7-237.7° C.): $^1$H NMR (400 MHz, d6-DMSO) δ 12.44 (br s, 1H), 8.66 (dd, J=2.4, 0.4, 1H), 7.78 (dd, J=8.8, 2.4, 1H), 7.43 (d, J=8.0, 1H), 7.18 (d, J=2.0, 1H), 7.01 (dd, J=8.4, 2.4, 1H), 6.19 (dd, J=9.2, 0.4, 1H), 3.94 (q, J=6.8, 2H), 1.66 (s, 4H), 1.26 (s, 6H), 1.22 (s, 6H), 1.22 (t, J=6.8, 3H); $^{13}$C NMR (100.6 MHz, d6-DMSO) δ 166.6, 159.7, 150.5, 146.5, 143.1, 140.7, 137.6, 128.1, 125.4, 124.8, 114.7, 106.7, 44.7, 34.5, 34.4, 34.0, 33.8, 31.5, 31.4, 12.7; IR (neat) 2925, 1666, 1592, 1409, 1274 cm$^{-1}$; ES-MS (M−H)− calcd for $C_{22}H_{27}N_2O_2$ 351.2072, found 351.2073. Anal. Calcd for $C_{22}H_{28}N_2O_2$: C, 74.97; H, 8.01; N, 7.95. Found: C, 74.74; H, 8.38; N, 7.56.

The intermediate compound 36 was prepared as follows.

a. 5,5,8,8-Tetramethyl-5,6,7,8-tetrahydronaphthalen-2-amine (33)

A 0.05 M solution of 1,1,4,4-tetramethyl-6-nitro-1,2,3,4-tetrahydronaphthalene (32) (2.5 g, 10.7 mmol) in ethyl acetate (210 mL) was passed through a 10% Pd/C cartridge at 1.0 mL/minute, twice, in the ThalesNano H-cube® at 70° C. and 2-5 bar pressure. The resulting solution was concentrated in vacuo to give compound 33 (2.1532 g, 99%) as a yellow, crystalline solid, m.p. 58-60° C.: $^1$H NMR (400 MHz, CDCl₃) δ 7.11 (d, J=8.4, 1H), 6.65 (d, J=2.4, 1H), 6.54 (dd, J=8.4, 2.4, 1H), 3.62 (br s, 2H), 1.66 (s, 4H), 1.26 (s, 6H), 1.25 (s, 6H); $^{13}$C NMR (100.6 MHz, CDCl₃) δ 145.8, 143.3, 135.4, 127.3, 113.7, 112.9, 35.2, 34.1, 33.5, 31.9, 31.7; IR (neat) 3405, 3208, 2952, 2920, 1612, 1499 cm$^{-1}$; LC-MS-CI (M+H)+ calcd for $C_{14}H_{22}N$ 204.1752, found 204.1747.

b. Methyl 6-((5,5,8,8-tetramethyl-5,6,7,8-tetrahydronaphthalen-2-yl)amino)nicotinate (35)

To a 100 mL, one-neck, round-bottomed flask equipped with a magnetic stir bar and charged with 33 (0.8047 g, 3.958 mmol), methyl 6-chloronicotinate (34) (0.6897, 4.02 mmol), and p-TsOH (0.7605 g, 4.0 mmol) was added 1,4-dioxane (15 mL). The flask was fitted with a reflux condenser, evacuated and back-filled with nitrogen, heated to reflux and stirred in an oil bath at 111° C. for 14 hours. After cooling the reaction to room temperature, the reaction mixture was poured into water (50 mL) and extracted with ethyl acetate. The combined organic layers were washed with brine, dried over sodium sulfate, filtered, and concentrated in vacuo to yield a crude product that was purified by column chromatography (150 mL $SiO_2$, 10% ethyl acetate:hexanes) to give compound 35 (0.8152 g, 61%) as a white crystalline solid, m.p. 167-171° C.: $^1$H NMR (400 MHz, $CDCl_3$) δ 8.81 (dd, J=2.0, 0.4, 1H), 8.02 (dd, J=8.8, 2.0, 1H), 7.94 (s, 1H), 7.31 (d, J=7.6, 1H), 7.21 (d, J=2.4, 1H), 7.12 (dd, J=8.4, 2.4, 1H), 6.82 (dd, J=8.8, 0.4, 1H), 3.87 (s, 3H), 1.70 (s, 4H), 1.29 (s, 12H); $^{13}$C NMR (100.6 MHz, $CDCl_3$) δ 166.0, 159.4, 151.2, 146.3, 141.5, 138.9, 136.1, 127.5, 120.4, 120.0, 116.3, 106.0, 51.6, 35.0, 34.9, 34.3, 33.9, 31.8, 31.7; IR (neat) 3224, 2954, 1715, 1597, 1535, 1261 $cm^{-1}$; ES-MS (M+Na)+ calcd for $C_{21}H_{26}N_2O_2Na$ 361.1892, found 361.1899.

c. Methyl 6-(ethyl(5,5,8,8-tetramethyl-5,6,7,8-tetrahydronaphthalen-2-yl)amino)nicotinate (36)

To a flame-dried, 100 mL round-bottomed flask equipped with a magnetic stir bar was added a 60% dispersion of sodium hydride in mineral oil (0.210 g, 5.25 mmol). The dispersion of sodium hydride was washed with hexanes (3 mL, twice) and dried under vacuum and suspended in 3.1 mL of DMF under nitrogen. To this solution of sodium hydride in DMF was added a solution of 35 (0.8386 g, 2.478 mmol) in DMF (8.3 mL), and the reaction was stirred for 15 minutes, and then ethyl iodide (0.34 mL, 4.25 mmol) was added, and the reaction was stirred for 1 hour. The reaction was poured into water and extracted with ethyl acetate. The combined organic layers were washed with brine, dried over sodium sulfate, filtered, and concentrated in vacuo to yield a crude product that was purified by column chromatography (150 mL $SiO_2$, 6% ethyl acetate:hexanes) to give compound 36 (0.619 g, 68%) as a white crystalline solid, m.p. 114-116° C.: $^1$H NMR (400 MHz, $CDCl_3$) δ 8.83 (dd, J=2.4, 0.4, 1H), 7.78 (dd, J=9.2, 2.4, 1H), 7.35 (d, J=8.4, 1H), 7.11 (d, J=2.0, 1H), 6.95 (dd, J=8.4, 2.4, 1H), 6.21 (d, J=9.2, 1H), 4.02 (q, J=7.2, 2H), 3.85 (s, 3H), 1.70 (s, 4H), 1.31 (s, 6H), 1.25 (s, 6H), 1.22 (t, J=7.2, 3H); $^{13}$C NMR (100.6 MHz, $CDCl_3$) δ 166.6, 160.4, 151.0, 146.9, 143.8, 140.9, 137.2, 128.1, 125.8, 124.8, 114.2, 107.4, 51.5, 45.3, 35.0, 34.9, 34.4, 34.1, 31.8, 31.8, 13.0; IR (neat) 2956, 1708, 1596, 1267 $cm^{-1}$; ES-MS (M+Na)+ calcd for $C_{23}H_{30}N_2O_2Na$ 389.2205, found 389.2211.

Example 2. 4-(Ethyl(5,5,8,8-tetramethyl-5,6,7,8-tetrahydronaphthalen-2-yl)amino)benzoic acid (21)

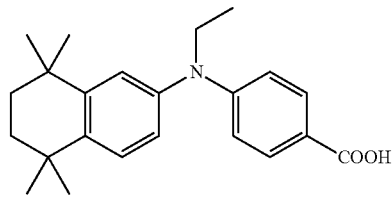 [SMILES: CCN(c1ccc(C(=O)O)cc1)c1ccc2c(c1)C(C)(C)CCC2(C)C]

To a 100 mL round-bottomed flask equipped with a stir bar and charged with methyl ester 39 (0.3742 g, 1.02 mmol) suspended in methanol (3.6 mL) was added a solution of potassium hydroxide (0.2029 g, 3.62 mmol) in water (0.24 mL). This reaction was stirred at reflux in an oil bath at 87° C. for 1 h. The reaction was then cooled to room temperature and acidified with 20% HCl (56 mL). The precipitate was filtered to give 0.3516 g (97%) of a crude product that was purified by column chromatography (25 mL $SiO_2$, 20% ethyl acetate:hexanes to 50% ethyl acetate:hexanes) to give pure 21 (0.3043 g, 84%) as a white crystalline solid, m.p. 247.8-250.6° C.: $^1$H NMR (400 MHz, d6-DMSO) δ 12.14 (br s, 1H), 7.69 (d, J=9.2, 2H), 7.38 (d, J=8.4, 1H), 7.12 (d, J=2.0, 1H), 6.95 (dd, J=8.4, 2.4, 1H), 6.64 (d, J=8.8, 2H), 3.72 (q, J=7.2, 1H), 1.65 (s, 4H), 1.26, (s, 6H), 1.21 (s, 6H), 1.13 (t, J=7.2, 3H); $^{13}$C NMR (100.6 MHz, d6-DMSO) δ 167.2, 151.1, 146.1, 142.6, 141.9, 130.9, 127.9, 124.6, 124.1, 118.2, 112.6, 34.5, 34.4, 34.0, 33.7, 31.5, 31.4, 12.1; IR (neat) 2955, 1661, 1594, 1270, 1180 $cm^{-1}$; ES-MS (M−H)− calcd for $C_{23}H_{28}NO_2$ 350.2120, found 350.2122. Anal. Calcd for $C_{23}H_{29}NO_2$: C, 78.59; H, 8.32; N, 3.99. Found: C, 78.30; H, 8.70; N, 3.87.

The intermediate compound 39 was prepared as follows.

a. Methyl 4-((5,5,8,8-tetramethyl-5,6,7,8-tetrahydronaphthalen-2-yl)amino)benzoate (38)

To a solution of compound 33 (0.8360 g, 4.11 mmol), compound 37 (1.0919 g, 4.17 mmol), $CsCO_3$ (3.12 g, 9.58 mmol), and rac-BINAP (0.1992 g, 0.32 mmol) in toluene (4.5 mL) in a 100 mL round-bottomed flask was added $Pd_2(dba)_3$ (0.1870 g, 0.20 mmol). The solution was sparged with nitrogen for 5 minutes, then a reflux condenser was fitted to the flask, the atmosphere was evacuated and back-filled with nitrogen (three times), and the reaction was heated to reflux with stirring in an oil bath (125-120° C.) for 22 hours. After cooling the reaction to room temperature, excess cesium carbonate and other solid particulates were filtered and washed with ethyl acetate, and the organic filtrate was concentrated in vacuo to give a crude product that was purified by column chromatography (150 mL $SiO_2$, 3.5% ethyl acetate:hexanes) to give compound 38 (0.8569 g, 62%) as a crystalline solid, m.p. 118-124.7° C.: $^1$H NMR (400 MHz, $CDCl_3$) δ 7.90 (d, J=6.8, 1H), 7.27 (d, J=8.4, 1H), 7.10 (d, J=2.4, 1H), 6.96 (dd, J=8.4, 2.8, 1H), 6.93 (d, J=6.8, 2.0 1H), 6.01 (br s, 1H), 3.87 (s, 3H), 1.70 (s, 4H), 1.29 (s, 6H), 1.27 (s, 6H); $^{13}$C NMR (100.6 MHz, $CDCl_3$) δ 167.0, 148.7, 146.1, 140.2, 137.8, 131.8, 127.5, 120.3, 118.9, 118.7, 113.9, 51.6, 35.0, 34.3, 33.8, 31.8, 31.7; IR (neat) 3354, 2954, 1693, 1586, 1276 $cm^{-1}$; ES-MS (M+Na)+ calcd for $C_{22}H_{27}NO_2Na$ 360.1939, found 360.1936.

b. Methyl 4-(ethyl(5,5,8,8-tetramethyl-5,6,7,8-tetrahydronaphthalen-2-yl)amino)benzoate (39)

To a flame-dried, 100 mL round-bottomed flask equipped with a magnetic stir bar was added a 60% dispersion of sodium hydride in mineral oil (0.1933 g, 4.8 mmol). The dispersion of sodium hydride was washed with hexanes (2.6 mL, twice) and dried under vacuum and suspended in 2.7 mL of DMF under nitrogen. To this solution of sodium hydride in DMF was added a solution of compound 38 (0.7204 g, 2.13 mmol) in DMF (8.0 mL), and the reaction was stirred for 15 minutes, and then ethyl iodide (0.26 mL, 3.3 mmol) was added, and the reaction was stirred for 1 hour. The reaction was poured into water and extracted with ethyl acetate. The combined organic layers were washed with brine, dried over sodium sulfate, filtered, and concentrated in vacuo to yield a crude product that was purified by column chromatography (150 mL $SiO_2$, 6% ethyl acetate:hexanes) to give compound 39 (0.7803 g, 56%) as a white crystalline solid, m.p. 105.3-106.3° C.: $^1$H NMR (400 MHz, $CDCl_3$) δ 7.83 (d, J=12.0, 1H), 7.31 (d, J=8.4, 1H), 7.10 (d, J=2.4, 1H), 6.92 (dd, J=8.4, 2.4, 1H), 6.67 (d, J=12.0, 1H), 3.91 (s, 3H), 3.76 (q, J=7.2, 2H), 1.70 (s, 4H), 1.31 (s, 6H), 1.24 (s, 6H), 1.24 (t, J=7.2, 3H); $^{13}$C NMR (100.6 MHz, $CDCl_3$) δ 167.3, 151.7, 146.6, 142.9, 142.6, 131.0, 127.9, 125.2, 124.2, 117.8, 112.7, 51.4, 46.6, 35.0, 34.9, 34.3, 34.0, 31.8, 31.7, 12.4; IR (neat) 2953, 1702, 1596, 1266 $cm^{-1}$; ES-MS (M+Na)+ calcd for $C_{24}H_{31}NO_2Na$ 388.2253, found 388.2256.

Example 3. 4-(Ethyl(3,5,5,8,8-pentamethyl-5,6,7,8-tetrahydronaphthalen-2-yl)amino)benzoic acid (22)

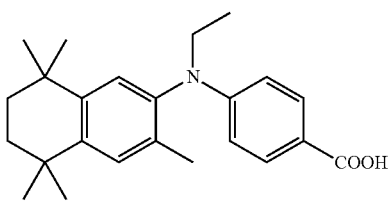 [SMILES: CCN(c1ccc(C(=O)O)cc1)c1cc2c(cc1C)C(C)(C)CCC2(C)C]

To a 100 mL round-bottomed flask equipped with a stir bar and charged with methyl ester 44 (0.5537 g, 1.46 mmol) suspended in methanol (5.0 mL) was added a solution of potassium hydroxide (0.2665 g, 4.75 mmol) in water (0.32 mL). This reaction was stirred at reflux in an oil bath at 87° C. for 1 h. The reaction was then cooled to room temperature and acidified with 20% HCl (76 mL). The precipitate was filtered to give a crude product that was purified by column chromatography (25 mL $SiO_2$, 20% ethyl acetate:hexanes to 50% ethyl acetate:hexanes) to give pure 22 (0.3815 g, 71%) as a white crystalline solid, m.p. 252.4-256.8° C.: $^1$H NMR (400 MHz, d6-DMSO) δ 12.06 (br s, 1H), 7.68 (d, J=9.2, 2H), 7.28 (s, 1H), 7.02 (s, 1H), 6.40 (d, J=8.8, 2H), 3.62 (br s, 2H), 1.97 (s, 3H), 1.63 (s, 4H), 1.25, (s, 6H), 1.19 (s, 6H), 1.14 (t, J=7.2, 3H); $^{13}$C NMR (100.6 MHz, d6-DMSO) δ 167.3, 151.1, 144.0, 143.2, 140.7, 132.8, 131.1, 129.1, 126.6, 117.3, 110.7, 45.4, 34.6, 34.4, 33.7, 33.6, 31.6, 31.5, 17.0, 12.2; IR (neat) 2957, 1665, 1597, 1274, 1176 $cm^{-1}$; ES-MS (M−H)− calcd for $C_{24}H_{30}NO_2$ 364.2277, found 364.2268. Anal. Calcd for $C_{24}H_{31}NO_2$: C, 78.86; H, 8.55; N, 3.83. Found: C, 78.87; H, 8.91; N, 3.76.

The intermediate ester 44 was prepared as follows.

a. 1. 1,1,4,4,6-pentamethyl-7-nitro-1,2,3,4-tetrahydronaphthalene (41)

To a solution of 1,1,4,4,6-pentamethyl-1,2,3,4-tetrahydronaphthalene (40) (2.0 g, 9.9 mmol) in acetic anhydride (10 mL) cooled to 0° C. was added concentrated nitric acid (0.80 mL), dropwise. A precipitate quickly formed (2 min.) and the heterogeneous solution was poured onto ice and then extracted with ethyl acetate. The combined organic layers were washed with brine and then dried over sodium sulfate, filtered and concentrated in vacuo to give a crude residue. This residue was dissolved in hot ethyl acetate (4.0 mL) and hexanes (6.0 mL) was added and the solution was cooled in an ice bath and the resulting precipitate was filtered to give compound 41 (1.23 g, 50%) as a white crystalline solid, m.p. 148-150° C.: $^1$H NMR (400 MHz, $CDCl_3$) δ 7.96 (s, 1H), 7.21 (s, 1H), 2.56 (s, 3H), 1.69 (s, 4H), 1.29 (s, 12H); $^{13}$C NMR (100.6 MHz, $CDCl_3$) δ 151.1, 146.8, 144.3, 130.9, 130.4, 123.1, 34.6, 34.5, 34.5, 34.2, 31.6, 31.5, 20.5; IR (neat) n 2960, 2924, 1515, 1347 $cm^{-1}$; LC-MS-CI $(M+NH_4)+$ calcd for $C_{15}H_{25}N_2O_2$ 265.1916, found 265.1927.

b. 3,5,5,8,8-pentamethyl-5,6,7,8-tetrahydronaphthalen-2-amine (42)

A 0.05 M solution of 1,1,4,4,6-pentamethyl-7-nitro-1,2,3,4-tetrahydronaphthalene (41) (2.5 g, 10.1 mmol) in ethyl acetate (205 mL) was passed through a 10% Pd/C cartridge at 1.0 mL/minute, twice, in the ThalesNano H-cube® at 70° C. and 2-5 bar pressure. The resulting solution was concentrated in vacuo to give compound 42 (2.13 g, 97%) as a yellow, crystalline solid, m.p. 76-89° C.: $^1$H NMR (400 MHz, $CDCl_3$) δ 7.00 (s, 1H), 6.63 (s, 1H), 3.34 (br s, 2H), 2.15 (s, 3H), 1.63 (s, 4H), 1.26 (s, 12H); $^{13}$C NMR (100.6 MHz, $CDCl_3$) δ 143.5, 142.0, 135.2, 128.3, 120.5, 112.6, 35.3, 35.2, 33.8, 33.4, 32.0, 31.8, 17.1; IR (neat) n 3404, 3335, 2956, 2925, 1626, 1504 $cm^{-1}$; LC-MS-CI (M+H)+ calcd for $C_{15}H_{24}N$ 218.1909, found 218.1908.

c. Methyl 4-((3,5,5,8,8-pentamethyl-5,6,7,8-tetrahydronaphthalen-2-yl)amino)benzoate (43)

To a solution of compound 42 (1.7092 g, 7.86 mmol), compound 37 (2.1030 g, 8.03 mmol), $CsCO_3$ (6.24 g, 19.2 mmol), and rac-BINAP (0.3836 g, 0.616 mmol) in toluene (9.0 mL) in a 100 mL round-bottomed flask was added $Pd_2(dba)_3$ (0.3596 g, 0.20 mmol). The solution was sparged with nitrogen for 5 minutes, then a reflux condenser was fitted to the flask, the atmosphere was evacuated and backfilled with nitrogen (three times), and the reaction was heated to reflux with stirring in an oil bath (125-120° C.) for 22 hours. After cooling the reaction to room temperature, excess cesium carbonate and other solid particulates were filtered and washed with ethyl acetate, and the organic filtrate was concentrated in vacuo to give a crude product that was purified by column chromatography (150 mL $SiO_2$, 3.5% ethyl acetate:hexanes) to give compound 43 (2.2557 g, 81%) as a crystalline solid, m.p. 132-147° C.: $^1$H NMR (400 MHz, $CDCl_3$) δ 7.88 (d, J=8.8, 2H), 7.21 (s, 1H), 7.16 (s, 1H), 6.77 (d, J=9.2, 2H), 5.68 (br s, 1H), 3.86 (s, 3H), 2.19 (s, 3H), 1.69 (s, 4H), 1.30 (s, 6H), 1.24 (s, 6H); $^{13}$C NMR (100.6 MHz, $CDCl_3$) δ 167.1, 149.7, 143.7, 141.5, 136.0, 131.4, 129.1, 129.0, 121.3, 119.8, 113.5, 51.5, 35.1, 35.0, 34.0, 33.8, 31.8, 17.6; IR (neat) 3352, 2956, 1687, 1597, 1276 cm$^{-1}$; ES-MS (M+Na)+ calcd for $C_{23}H_{29}NO_2Na$ 374.2096, found 374.2092.

d. Methyl 4-(ethyl(3,5,5,8,8-pentamethyl-5,6,7,8-tetrahydronaphthalen-2-yl)amino)benzoate (44)

To a flame-dried, 100 mL round-bottomed flask equipped with a magnetic stir bar was added a 60% dispersion of sodium hydride in mineral oil (0.2646 g, 6.62 mmol). The dispersion of sodium hydride was washed with hexanes (3.7 mL, twice) and dried under vacuum and suspended in 3.8 mL of DMF under nitrogen. To this solution of sodium hydride in DMF was added a solution of compound 43 (1.018 g, 2.90 mmol) in DMF (11.4 mL), and the reaction was stirred for 15 minutes, and then ethyl iodide (0.36 mL, 4.5 mmol) was added, and the reaction was stirred for 1 hour. The reaction was poured into water and extracted with ethyl acetate. The combined organic layers were washed with brine, dried over sodium sulfate, filtered, and concentrated in vacuo to yield a crude product that was purified by column chromatography (150 mL $SiO_2$, 2.5% ethyl acetate: hexanes) to give compound 44 (1.073 g, 97%) as a white crystalline solid, m.p. 104.6-106.0° C.: $^1$H NMR (400 MHz, $CDCl_3$) δ 7.82 (d, J=9.2, 2H), 7.20 (s, 1H), 7.00 (s, 1H), 6.44 (d, J=8.8, 2H), 3.83 (s, 3H), 3.66 (q, J=7.2, 2H), 2.03 (s, 3H), 1.69 (s, 4H), 1.31 (s, 6H), 1.25 (t, J=6.8, 3H), 1.23 (s, 6H); $^{13}$C NMR (100.6 MHz, $CDCl_3$) δ 167.4, 151.7, 144.4, 143.9, 140.9, 133.1, 131.2, 129.3, 127.1, 116.9, 111.0, 51.3, 45.8, 35.1, 34.9, 34.0, 34.0, 31.9, 31.8, 17.4, 12.4; IR (neat) 2954, 1701, 1602, 1275, 1176 cm$^{-1}$; ES-MS (M+Na)+ calcd for $C_{25}H_{33}NO_2Na$ 402.2409, found 402.2403.

Example 4. 6-(Ethyl(3,5,5,8,8-pentamethyl-5,6,7,8-tetrahydronaphthalen-2-yl)amino)nicotinic acid (23)

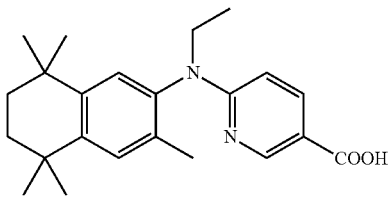 [SMILES: CCN(c1ccc(C(=O)O)cn1)c1cc2c(cc1C)C(C)(C)CCC2(C)C]

Using a procedure similar to that described for the preparation of compound 22, the title compound 23 (0.4448 g, 91%) was prepared as a white crystalline solid, m.p. 250.2-251.0° C.: $^1$H NMR (400 MHz, d6-DMSO) δ 12.42 (br s, 1H), 8.66 (d, J=2.0, 1H), 7.78 (dd, J=8.8, 2.0, 1H), 7.32 (s, 1H), 7.07 (s, 1H), 5.89 (br s, 1H), 4.19-4.05 (m, 1H), 3.65-3.55 (m, 1H), 1.98 (s, 3H), 1.64 (s, 4H), 1.26 (d, J=6.4, 6H), 1.20 (s, 6H), 1.13 (t, J=7.2, 3H); $^{13}$C NMR (100.6 MHz, d6-DMSO) δ 166.6, 159.5, 150.7, 144.1, 143.8, 139.0, 137.9, 132.5, 129.2, 126.5, 114.4, 105.9, 44.0, 34.5, 34.4, 33.7, 31.6, 31.5, 16.9, 12.7; IR (neat) 2960, 1669, 1595, 1509, 1412, 1266 cm$^{-1}$; ES-MS (M−H)− calcd for $C_{23}H_{29}N_2O_2$ 365.2229, found 365.2235. Anal. Calcd for $C_{23}H_{30}N_2O_2$: C, 75.37; H, 8.25; N, 7.64. Found: C, 75.33; H, 8.46; N, 7.56.

The intermediate compound 48 was prepared as follows.

a. Methyl 6-((3,5,5,8,8-pentamethyl-5,6,7,8-tetrahydronaphthalen-2-yl)amino)nicotinate (47)

Using a procedure similar to that described for the preparation of compound 43, the title compound 47 (0.5072 g, 37%) was prepared as a crystalline solid, m.p. 169-175.8° C.: $^1$H NMR (400 MHz, $CDCl_3$) δ 8.79 (dd, J=2.4, 0.8, 1H), 8.00 (dd, J=8.8, 2.0, 1H), 7.25 (s, 1H), 7.18 (s, 1H), 7.05 (br s, 1H), 6.49 (dd, J=8.8, 0.8, 1H), 3.87 (s, 3H), 2.20 (s, 3H), 1.68 (s, 4H), 1.29 (s, 6H), 1.25 (s, 6H); $^{13}$C NMR (100.6 MHz, $CDCl_3$) δ 166.1, 160.0, 151.3, 143.8, 143.0, 138.9, 134.1, 130.3, 129.1, 123.1, 116.1, 105.5, 51.7, 35.0, 34.9, 34.0, 33.9, 31.8, 31.8, 17.6; IR (neat) 2961, 1722, 1605, 1399, 1273 cm$^{-1}$; ES-MS (M+Na)+ calcd for $C_{22}H_{28}N_2O_2Na$ 375.2048, found 375.2050.

b. Methyl 6-(ethyl(3,5,5,8,8-pentamethyl-5,6,7,8-tetrahydronaphthalen-2-yl)amino)nicotinate (48)

Using a procedure similar to that described for the preparation of compound 44, the title compound 48 (0.9012 g, 78%) was prepared as a white crystalline solid, m.p. 100.1-102.4° C.: $^1$H NMR (400 MHz, $CDCl_3$) δ 8.85 (dd, J=2.4, 0.4, 1H), 7.78 (dd, J=9.2, 2.4, 1H), 7.21 (s, 1H), 7.00 (s, 1H), 5.91 (d, J=8.8, 1H), 4.32-4.23 (m, 1H), 3.84 (s, 3H), 3.67-3.59 (m, 1H), 2.04 (s, 3H), 1.69 (s, 4H), 1.30 (d, J=8.0, 6H), 1.23 (t, J=7.2, 9H); $^{13}$C NMR (100.6 MHz, $CDCl_3$) δ 166.7, 160.2, 151.2, 144.6, 144.5, 139.1, 137.5, 132.8, 129.4, 127.0, 113.9, 106.7, 51.5, 44.5, 35.0, 34.9, 34.1, 34.0, 31.8, 17.2, 13.0; IR (neat) 2953, 1708, 1598, 1504, 1269, 1111 cm$^{-1}$; ES-MS (M+Na)+ calcd for $C_{24}H_{32}N_2O_2Na$ 403.2361, found 403.2365.

Example 5. 2-(ethyl(5,5,8,8-tetramethyl-5,6,7,8-tetrahydronaphthalen-2-yl)amino)pyrimidine-5-carboxylic acid (24)

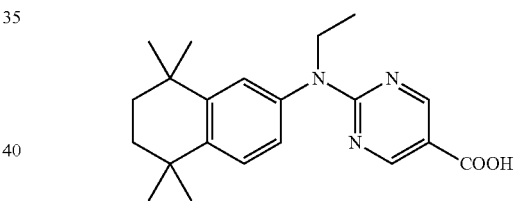

Using a procedure similar to that described for the preparation of compound 20, the title compound 24 (0.3668 g, 97%) was prepared as a white crystalline solid, m.p. 249.5-250.6° C.: $^1$H NMR (400 MHz, d6-DMSO) δ 12.62 (br s, 1H), 8.37 (s, 1H), 7.35 (d, J=8.4, 1H), 7.17 (d, J=2.4, 1H), 7.00 (dd, J=8.4, 2.0, 1H), 3.99 (q, J=7.2, 2H), 1.67 (s, 4H), 1.27 (s, 6H), 1.24 (s, 6H), 1.16 (t, J=7.2, 3H); $^{13}$C NMR (100.6 MHz, d6-DMSO) δ 165.1, 161.9, 159.1, 15.2, 142.3, 140.2, 126.8, 124.7, 124.6, 113.5, 45.3, 34.4, 34.4, 33.7, 33.5, 31.4, 31.3, 12.3; IR (neat) 2962, 1664, 1586, 1515, 1426, 1278 cm$^{-1}$; ES-MS (M−H)− calcd for $C_{21}H_{26}N_3O_2$ 352.2025, found 352.2024. Anal. Calcd for $C_{21}H_{27}N_3O_2$: C, 71.36; H, 7.70; N, 11.89. Found: C, 71.40; H, 7.98; N, 11.79.

The intermediate compound 51 was prepared as follows.

a. Methyl 2-((5,5,8,8-tetramethyl-5,6,7,8-tetrahydronaphthalen-2-yl)amino)pyrimidine-5-carboxylate (50)

Using a procedure similar to that described for the preparation of compound 35, the title compound 50 (1.0177 g, 75%) was prepared as a white crystalline solid, m.p. 143.2-149.3° C.: $^1$H NMR (400 MHz, $CDCl_3$) δ 8.95 (s, 2H), 8.25 (br s, 1H), 7.47 (dd, J=8.4, 2.4, 1H), 7.42 (d, J=2.0, 1H), 7.32

(d, J=8.4, 1H), 3.90 (s, 3H), 1.69 (s, 4H), 1.30 (s, 6H), 1.28 (s, 6H); $^{13}$C NMR (100.6 MHz, CDCl$_3$) δ 164.7, 161.4, 145.7, 141.1, 135.3, 127.1, 118.8, 118.7, 114.7, 51.9, 35.0, 34.3, 33.9, 31.8, 31.8; IR (neat) 3254, 2954, 1720, 1597, 1526, 1433, 1289, 1258, 1123 cm$^{-1}$; ES-MS (M+Na)+ calcd for C$_{20}$H$_{25}$N$_3$O$_2$Na 362.1844, found 362.1844.

b. Methyl 2-(ethyl(5,5,8,8-tetramethyl-5,6,7,8-tetrahydronaphthalen-2-yl)amino)pyrimidine-5-carboxylate (51)

Using a procedure similar to that described for the preparation of compound 36, the title compound 51 (0.7997 g, 75%) was prepared as a white crystalline solid, m.p. 181.2-183.9° C.: $^1$H NMR (400 MHz, CDCl$_3$) δ 8.85 (s, 1H), 7.33 (d, J=8.4, 1H), 7.13 (d, J=2.4, 1H), 7.00 (d, J=2.4, 1H), 6.98 (d, J=2.0, 1H), 4.03 (q, J=7.2, 2H), 3.86 (s, 3H), 1.69 (s, 4H), 1.30 (s, 6H), 1.26 (s, 6H), 1.24 (t, J=7.2, 3H); $^{13}$C NMR (100.6 MHz, CDCl$_3$) δ 165.3, 162.4, 159.7, 146.0, 143.3, 140.3, 127.4, 125.1, 124.2, 112.9, 51.6, 46.5, 35.0, 34.9, 34.3, 34.1, 31.8, 31.8, 12.8; IR (neat) 2930, 1706, 1594, 1504, 1284, 1122 cm$^{-1}$; ES-MS (M+Na)+ calcd for C$_{22}$H$_{29}$N$_3$O$_2$Na 390.2158, found 390.2155.

Example 6. 2-(Ethyl(3,5,5,8,8-pentamethyl-5,6,7,8-tetrahydronaphthalen-2-yl)amino)pyrimidine-5-carboxylic acid (25)

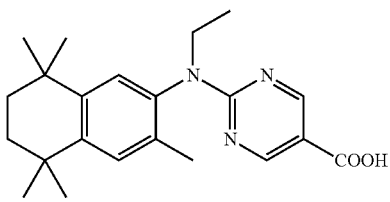 [SMILES: CCN(c1ncc(C(=O)O)cn1)c1cc2c(cc1C)C(C)(C)CCC2(C)C]

Using a procedure similar to that described for the preparation of compound 22, the title compound 25 (0.3203 g, 84%) was prepared as a white crystalline solid, m.p. 231.9-233.1° C.: $^1$H NMR (400 MHz, d6-DMSO) δ 12.60 (br s, 1H), 8.74 (br s, 2H), 7.23 (s, 1H), 7.05 (s, 1H), 4.04 (sextet, J=7.2, 1H), 3.76 (sextet, J=7.2, 1H), 1.97 (s, 3H), 1.65 (s, 4H), 1.29, (s, 3H), 1.26 (s, 3H), 1.23 (s, 3H), 1.20 (s, 3H), 1.16 (t, J=7.2, 3H); $^{13}$C NMR (100.6 MHz, d6-DMSO) δ 165.2, 161.7, 159.3, 143.0, 142.9, 139.1, 132.0, 128.2, 125.4, 113.2, 45.0, 34.5, 34.4, 33.4, 33.3, 31.5, 31.4, 31.2, 16.9, 12.3; IR (neat) 2952, 1663, 1591, 1508, 1426, 1281 cm$^{-1}$; ES-MS (M-H)– calcd for C$_{22}$H$_{28}$N$_3$O$_2$ 366.2181, found 366.2185. Anal. Calcd for C$_{22}$H$_{29}$N$_3$O$_2$: C, 71.90; H, 7.95; N, 11.43. Found: C, 71.81; H, 8.23; N, 11.31.

The intermediate compound 54 was prepared as follows.

a. Methyl 2-((3,5,5,8,8-pentamethyl-5,6,7,8-tetrahydronaphthalen-2-yl)amino)pyrimidine-5-carboxylate (53)

Using a procedure similar to that described for the preparation of compound 43, the title compound 53 (0.6206 g, 45%) was prepared as a crystalline solid, m.p. 135.6-145.6° C.: $^1$H NMR (400 MHz, CDCl$_3$) δ 8.92 (s, 2H), 7.65 (s, 1H), 7.45 (br s, 1H), 7.16 (s, 1H), 3.89 (s, 3H), 2.24 (s, 3H), 1.68 (s, 4H), 1.29 (s, 6H), 1.28 (s, 6H); $^{13}$C NMR (100.6 MHz, CDCl$_3$) δ 164.8, 162.0, 160.2, 143.4, 133.2, 128.7, 128.4, 122.1, 114.6, 51.8, 35.1, 35.0, 34.1, 33.9, 31.8, 31.7, 17.8; IR (neat) 3250, 2954, 1718, 1598, 1527, 1430, 1286 cm$^{-1}$; ES-MS (M+Na)+ calcd for C$_{21}$H$_{27}$N$_3$O$_2$Na 376.2001, found 376.1998.

b. Methyl 2-(ethyl(3,5,5,8,8-pentamethyl-5,6,7,8-tetrahydronaphthalen-2-yl)amino)pyrimidine-5-carboxylate (54)

Using a procedure similar to that described for the preparation of compound 44, the title compound 54 (0.688 g, 65%) was prepared as a white crystalline solid, m.p. 159.2-161.0° C.: $^1$H NMR (400 MHz, CDCl$_3$) δ 8.93 (s, 1H), 8.78 (s, 1H), 7.19 (s, 1H), 7.00 (s, 1H), 4.15 (sextet, J=7.2, 1H), 3.85 (s, 3H), 3.74 (sextet, J=7.2, 1H), 2.05 (s, 3H), 1.68-1.66 (m, 4H), 1.32 (s, 3H), 1.27 (s, 3H), 1.26 (s, 3H), 1.25 (s, 3H), 1.24 (t, J=7.2, 3H); $^{13}$C NMR (100.6 MHz, CDCl$_3$) δ 165.4, 162.3, 160.0, 159.8, 143.8, 143.7, 139.2, 132.1, 129.0, 125.8, 112.6, 51.6, 46.0, 35.1, 34.9, 34.0, 34.0, 32.0, 32.0, 31.7, 31.6, 17.5, 12.7; IR (neat) 2955, 1703, 1594, 1513, 1279, 1267, 1126, 1099 cm$^{-1}$; ES-MS (M+Na)+ calcd for C$_{23}$H$_{31}$N$_3$O$_2$Na 404.2314, found 404.2312.

Example 7. 5-(Ethyl(5,5,8,8-tetramethyl-5,6,7,8-tetrahydronaphthalen-2-yl)amino)pyrazine-2-carboxylic acid (26)

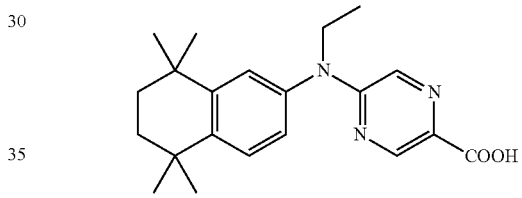

Using a procedure similar to that described for the preparation of compound 20, the title compound 26 (0.2516 g, 71%) was prepared as a white crystalline solid, m.p. 213.1-214.4° C.: $^1$H NMR (400 MHz, d6-DMSO) δ 12.59 (br s, 1H), 8.70 (d, J=1.6, 1H), 7.61 (d, J=1.2, 1H), 7.47 (d, J=8.0, 1H), 7.29 (d, J=2.4, 1H), 7.10 (dd, J=8.4, 2.4, 1H), 3.94 (q, J=7.1, 2H), 1.66 (s, 4H), 1.27 (s, 6H), 1.23 (s, 6H), 1.14 (t, J=7.2, 3H); $^{13}$C NMR (100.6 MHz, d6-DMSO) δ 165.4, 154.4, 146.7, 144.6, 143.8, 139.2, 130.8, 130.7, 128.4, 125.2, 124.4, 44.9, 34.4, 34.4, 34.1, 33.8, 31.5, 31.4, 12.2; IR (neat) 2931, 1671, 1556, 1416, 1276 cm$^1$; ES-MS (M–H)– calcd for C$_{21}$H$_{26}$N$_3$O$_2$ 352.2025, found 352.2020. Anal. Calcd for C$_{21}$H$_{27}$N$_3$O$_2$: C, 71.36; H, 7.70; N, 11.89. Found: C, 70.43; H, 7.64; N, 11.61.

The intermediate compound 57 was prepared as follows.

a. Methyl 5-((5,5,8,8-tetramethyl-5,6,7,8-tetrahydronaphthalen-2-yl)amino)pyrazine-2-carboxylate (56)

Using a procedure similar to that described for the preparation of compound 35, the title compound 56 (0.7674 g, 56%) was prepared as a white crystalline solid, m.p. 183.2-184.8° C.: $^1$H NMR (400 MHz, CDCl$_3$) δ 8.83 (d, J=1.6, 1H), 8.26 (d, J=1.2, 1H), 7.53 (br s, 1H), 7.33 (d, J=8.4, 1H), 7.32 (d, J=2.4, 1H), 7.21 (dd, J=8.4, 2.4, 1H), 3.95 (s, 3H), 1.68 (s, 4H), 1.27 (s, 6H), 1.26 (s, 6H); $^{13}$C NMR (100.6 MHz, CDCl$_3$) δ 164.9, 153.8, 146.3, 145.4, 142.1, 134.9, 132.6, 131.6, 127.7, 119.5, 119.2, 52.3, 34.9, 34.8, 34.3, 34.0, 31.7; IR (neat) 3325, 2952, 1713, 1527, 1281 cm$^{-1}$; ES-MS (M+Na)+ calcd for $C_{20}H_{25}N_3O_2Na$ 362.1844, found 362.1846.

b. Methyl 5-(ethyl(5,5,8,8-tetramethyl-5,6,7,8-tetrahydronaphthalen-2-yl)amino)pyrazine-2-carboxylate (57)

Using a procedure similar to that described for the preparation of compound 36, the title compound 57 (0.4189 g, 51%) was prepared as a white crystalline solid, m.p. 125.0-126.9° C.: $^1$H NMR (400 MHz, CDCl$_3$) δ 8.82 (d, J=1.6, 1H), 7.66 (d, J=1.2, 1H), 7.39 (d, J=8.4, 1H), 7.12 (d, J=2.4, 1H), 6.95 (dd, J=8.4, 2.4, 1H), 4.00 (q, J=7.2, 2H), 3.92 (s, 3H), 1.69 (s, 4H), 1.29 (s, 6H), 1.24 (s, 6H), 1.23 (t, J=7.2, 3H); $^{13}$C NMR (100.6 MHz, CDCl$_3$) δ 165.4, 155.2, 147.3, 145.3, 144.7, 139.2, 131.7, 131.7, 130.3, 128.6, 125.4, 124.3, 52.1, 45.4, 34.9, 34.8, 34.4, 34.2, 31.8, 31.7; IR (neat) 2956, 1703, 1564, 1527, 1279 cm$^{-1}$; ES-MS (M+Na)+ calcd for $C_{22}H_{29}N_3O_2Na$ 390.2158, found 390.2146.

Example 8. 5-(Ethyl(3,5,5,8,8-pentamethyl-5,6,7,8-tetrahydronaphthalen-2-yl)amino)pyrazine-2-carboxylic acid (27)

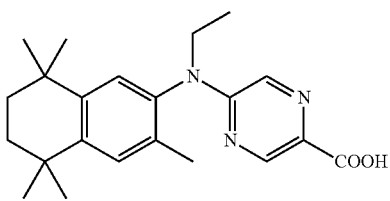 [SMILES: CCN(c1cnc(C(=O)O)cn1)c1cc2c(cc1C)C(C)(C)CCC2(C)C]

Using a procedure similar to that described for the preparation of compound 42, the title compound 27 (0.126 g, 57%) was prepared as a white crystalline solid, m.p. 203.6-205.1° C.: $^1$H NMR (400 MHz, d6-DMSO) δ 12.69 (br s, 1H), 8.70 (s, 1H), 7.36 (br s, 2H), 7.15 (s, 1H), 4.15-4.05 (m, 1H), 3.59 (sextet, J=7.2, 1H), 2.03 (s, 3H), 1.65 (s, 4H), 1.29, (s, 3H), 1.26 (s, 3H), 1.22 (s, 3H), 1.20 (s, 3H), 1.15 (t, J=7.2, 3H); $^{13}$C NMR (100.6 MHz, d6-DMSO) δ 165.4, 154.2, 144.8, 144.4, 144.3, 137.6, 132.3, 130.8, 130.0, 129.5, 126.4, 44.1, 34.5, 34.4, 33.7, 31.6, 31.5, 16.8, 12.1; IR (neat) 2959, 1671, 1557, 1524, 1417, 1286 cm$^{-1}$; ES-MS (M−H)− calcd for $C_{22}H_{28}N_3O_2$ 366.2181, found 366.2179. Anal. Calcd for $C_{22}H_{29}N_3O_2$: C, 71.90; H, 7.95; N, 11.43. Found: C, 71.62; H, 8.21; N, 11.19.

The intermediate compound 60 was prepared as follows a. Methyl 5-((3,5,5,8,8-pentamethyl-5,6,7,8-tetrahydronaphthalen-2-yl)amino)pyrazine-2-carboxylate (59)

Using a procedure similar to that described for the preparation of compound 43, the title compound 59 (0.8727 g, 63%) was prepared as a crystalline solid, m.p. 134.9-137.1° C.: $^1$H NMR (400 MHz, CDCl$_3$) δ 8.81 (d, J=1.2, 1H), 8.08 (d, J=1.6, 1H), 7.32 (s, 1H), 7.20 (s, 1H), 7.03 (br s, 1H), 3.95 (s, 3H), 2.22 (s, 3H), 1.68 (s, 4H), 1.28 (s, 6H), 1.24 (s, 6H); $^{13}$C NMR (100.6 MHz, CDCl$_3$) δ 164.8, 154.3, 145.4, 144.1, 143.6, 132.8, 130.7, 129.5, 129.3, 122.2, 52.3, 34.9, 34.8, 34.1, 33.9, 31.8, 31.7, 17.6; IR (neat) 3162, 2961, 1712, 1542, 1306, 1271, 1129 cm$^{-1}$; ES-MS (M+Na)+ calcd for $C_{21}H_{27}N_3O_2Na$ 376.2001, found 376.2006.

b. Methyl 5-(ethyl(3,5,5,8,8-pentamethyl-5,6,7,8-tetrahydronaphthalen-2-yl)amino)pyrazine-2-carboxylate (60)

Using a procedure similar to that described for the preparation of compound 44, the title compound 60 (0.226 g, 25%) was prepared as a white crystalline solid, m.p. 115.0-119.5° C.: $^1$H NMR (400 MHz, CDCl$_3$) δ 8.84 (d, J=1.2, 1H), 7.38 (br s, 1H), 7.24 (s, 1H), 7.00 (s, 1H), 4.24 (sextet, J=7.2, 1H), 3.91 (s, 3H), 3.59 (sextet, J=7.2, 1H), 2.06 (s, 3H), 1.68 (s, 4H), 1.29 (s, 6H), 1.24 (s, 3H), 1.24 (t, J=7.2, 3H), 1.19 (s, 3H); $^{13}$C NMR (100.6 MHz, CDCl$_3$) δ 165.4, 155.0, 150.0, 137.5, 132.4, 131.2, 130.2, 129.8, 126.6, 52.1, 44.5, 34.9, 34.8, 34.1, 34.0, 31.9, 31.8, 31.7, 17.1, 12.4; IR (neat) 2928, 1702, 1567, 1524, 1273, 1129 cm$^{-1}$; ES-MS (M+Na)+ calcd for $C_{23}H_{31}N_3O_2Na$ 404.2314, found 404.2305.

Example 9. 4-(Ethyl(5,5,8,8-tetramethyl-5,6,7,8-tetrahydronaphthalen-2-yl)amino)-2-fluorobenzoic acid (28)

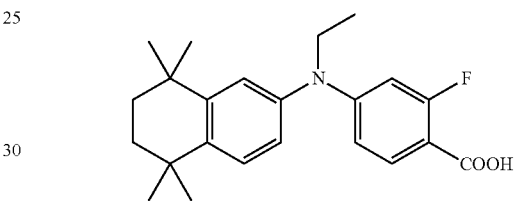

Using a procedure similar to that described for the preparation of compound 20, the title compound 28 (0.3342 g, 85%) was prepared as a white crystalline solid, m.p. 252.4-256.8° C.: $^1$H NMR (400 MHz, d6-DMSO) δ 12.35 (br s, 1H), 7.62 (t, J=9.2, 1H), 7.41 (d, J=8.4, 1H), 7.14 (d, J=2.4, 1H), 6.97 (dd, J=8.4, 2.4, 2H), 6.38 (dd, J=9.2, 2.4, 1H), 6.32 (dd, J=14.8, 2.4, 1H), 3.71 (q, J=7.2, 2H), 1.65 (s, 4H), 1.26, (s, 6H), 1.21 (s, 6H), 1.12 (t, J=7.2, 3H); $^{13}$C NMR (100.6 MHz, d6-DMSO) δ 164.9, 164.8, 164.5, 161.9, 153.0 152.9, 146.4, 142.7, 141.9, 133.2, 128.1, 125.1, 124.5, 108.6, 105.7, 105.6, 99.7, 99.4, 46.3, 34.5, 34.4, 34.0, 33.7, 31.5, 31.4, 12.0; IR (neat) 2964, 1668, 1617, 1282 cm$^{-1}$; ES-MS (M−H)− calcd for $C_{23}H_{27}FNO_2$ 368.2026, found 368.2043. Anal. Calcd for $C_{23}H_{28}FNO_2$: C, 74.77; H, 7.64; N, 3.79; F, 5.14. Found: C, 74.42; H, 8.00; N, 3.64; F, 4.1.

The intermediate compound 64 was prepared as follows.

a. Methyl 2-fluoro-4-iodobenzoate (62)

2-Fluoro-4-iodobenzoic acid (61) (5.35 g, 20.1 mmol) was dissolved in methanol (30 mL, 741 mmol) was added thionyl chloride (2.6 mL, 35.8 mmol), dropwise at 0° C. with stirring. The reaction solution was then refluxed in an oil bath at 85° C. for 1 hour. Excess methanol was removed in vacuo, and benzene (20 mL) was added to the residue and then removed in vacuo. To the residue was added ethyl acetate (150 mL), and the organic layer was washed with saturated NaHCO$_3$ (200 mL) and brine (60 mL) and then dried over sodium sulfate, filtered and concentrated in vacuo. The crude product was purified by column chromatography (150 mL SiO$_2$, ethyl acetate:hexanes 1:48) to give compound 62 (5.3066 g, 94%) as a white crystalline solid, m.p. 76-78° C.: $^1$H NMR (400 MHz, CDCl$_3$) δ 7.63 (t, J=8.0, 1H), 7.56 (dd, J=8.4, 1.6, 1H), 7.53 (dd, J=10.0, 1.2, 1H), 3.92 (s, 3H); $^{13}$C NMR (100.6 MHz, CDCl$_3$) δ 164.4, 164.3, 162.3, 159.7, 133.5, 133.4, 133.0, 126.5, 126.3, 118.2, 118.1, 99.8, 99.7, 52.5; IR (neat) n 2952, 1700, 1595, 1561 cm$^{-1}$; LC-FAB-MS (M)+ calcd for C$_8$H$_6$FIO$_2$ 279.9397, found 279.9394.

b. Methyl 2-fluoro-4-((5,5,8,8-tetramethyl-5,6,7,8-tetrahydronaphthalen-2-yl)amino)benzoate (63)

Using a procedure similar to that described for the preparation of compound 43, the title compound 63 (0.7449 g, 52%) was prepared as a crystalline solid, m.p. 121.8-136.7° C.: $^1$H NMR (400 MHz, CDCl$_3$) δ 7.80 (t, J=8.4, 1H), 7.27 (d, J=8.4, 1H), 7.08 (d, J=2.4, 1H), 6.96 (dd, J=8.4, 2.4, 1H), 6.65 (dd, J=8.8, 2.4, 1H), 6.62 (dd, J=12.4, 2.4, 1H), 5.95 (br s, 1H), 3.87 (s, 3H), 1.69 (s, 4H), 1.28 (s, 6H), 1.27 (s, 6H); $^{13}$C NMR (100.6 MHz, CDCl$_3$) δ 165.2, 164.9, 164.8, 162.6, 150.8, 150.7, 146.4, 141.2, 137.0, 133.6, 133.5, 127.6, 119.8, 119.4, 110.0, 108.0, 107.9, 101.4, 101.1, 51.7, 34.9, 34.9, 34.3, 33.9, 31.8, 31.7; IR (neat) 3344, 2956, 1703, 1620, 1601, 1273 cm$^{-1}$; ES-MS (M+Na)+ calcd for C$_{22}$H$_{26}$FNO$_2$Na 378.1845, found 378.1848.

c. Methyl 4-(ethyl(5,5,8,8-tetramethyl-5,6,7,8-tetrahydronaphthalen-2-yl)amino)-2-fluoro-benzoate (64)

Using a procedure similar to that described for the preparation of compound 36, the title compound 64 (0.4809 g, 68%) was prepared as a crystalline solid, m.p. 108.8-113.1° C.: $^1$H NMR (400 MHz, CDCl$_3$) δ 7.72 (t, J=9.2, 1H), 7.33 (d, J=8.4, 1H), 7.08 (d, J=2.0, 1H), 6.91 (dd, J=8.4, 2.4, 1H), 6.38 (dd, J=9.2, 2.4, 1H), 6.29 (dd, J=15.2, 2.4, 1H), 3.85 (s, 3H), 3.71 (q, J=7.2, 2H), 1.70 (s, 4H), 1.31 (s, 6H), 1.25 (s, 6H), 1.23 (t, J=7.2, 3H); $^{13}$C NMR (100.6 MHz, CDCl$_3$) δ 165.2, 165.1, 162.5, 153.6, 153.5, 146.8, 143.4, 142.2, 133.1, 133.0, 128.1, 125.5, 124.5, 108.5, 105.5, 100.3, 100.0, 51.5, 46.8, 34.9, 34.9, 34.4, 34.1, 31.8, 31.7, 12.3; IR (neat) 2954, 1712, 1621, 1266 cm$^{-1}$; ES-MS (M+Na)+ calcd for C$_{24}$H$_{30}$FNO$_2$Na 406.2158, found 406.2161.

Example 10. 4-(Ethyl(3,5,5,8,8-pentamethyl-5,6,7,8-tetrahydronaphthalen-2-yl)amino)-2-fluorobenzoic acid (29)

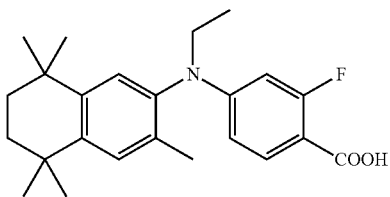 [SMILES: CCN(c1ccc(C(=O)O)c(F)c1)c1cc2c(cc1C)C(C)(C)CCC2(C)C]

Using a procedure similar to that described for the preparation of compound 20, the title compound 29 (0.4335 g, 84%) was prepared as a white crystalline solid, m.p. 241.4-243.8° C.: $^1$H NMR (400 MHz, d6-DMSO) δ 12.29 (br s, 1H), 7.62 (t, J=8.8, 1H), 7.31 (s, 1H), 7.03 (s, 1H), 6.19-6.11 (m, 2H), 3.61 (br s, 2H), 1.98 (s, 3H), 1.63 (s, 4H), 1.26, (s, 6H), 1.20 (s, 6H), 1.13 (t, J=7.2, 3H); $^{13}$C NMR (100.6 MHz, d6-DMSO) δ 164.9, 164.9, 164.7, 162.2, 153.0, 152.9, 144.1, 143.7, 140.0, 133.4, 132.6, 129.3, 126.5, 107.3, 105.1, 105.0, 98.3, 98.0, 45.6, 34.5, 34.4, 33.7, 31.6, 31.5, 16.9, 12.1; IR (neat) 2922, 1670, 1606, 1285 cm$^{-1}$; ES-MS (M−H)− calcd for C$_{24}$H$_{29}$FNO$_2$ 382.2182, found 382.2170.

Anal. Calcd for C$_{24}$H$_{30}$FNO$_2$: C, 75.16; H, 7.88; N, 3.65; F, 4.95. Found: C, 75.28; H, 8.45; N, 3.61; F, 4.3.

The intermediate compound 66 was prepared as follows.

a. Methyl 2-fluoro-4-((3,5,5,8,8-pentamethyl-5,6,7,8-tetrahydronaphthalen-2-yl)amino)-benzoate (65)

Using a procedure similar to that described for the preparation of compound 43, the title compound 65 (1.9009 g, 65%) was prepared as a crystalline solid, m.p. 159.7-165.1° C.: NMR (400 MHz, CDCl$_3$) δ 7.79 (t, J=8.8, 1H), 7.17 (d, J=3.6, 1H), 6.51 (dd, J=8.8, 2.0, 1H), 6.38 (dd, J=13.6, 2.0, 1H), 5.74 (br s, 1H), 3.87 (s, 3H), 2.17 (s, 3H), 1.68 (s, 4H), 1.29 (s, 6H), 1.24 (s, 6H); $^{13}$C NMR (100.6 MHz, CDCl$_3$) δ 165.3, 165.0, 164.9, 162.7, 151.9, 151.8, 143.9, 142.6, 135.2, 133.6, 133.5, 129.9, 129.1, 122.5, 109.6, 109.5, 107.5, 107.4, 100.9, 100.6, 51.7, 35.0. 34.9, 34.0, 33.9, 31.8; IR (neat) 3346, 2922, 1698, 1606, 1264 cm$^{-1}$; ES-MS (M+Na)+ calcd for C$_{23}$H$_{28}$FNO$_2$Na 392.2002, found 392.2003.

b. 2. Methyl 4-(ethyl(3,5,5,8,8-pentamethyl-5,6,7,8-tetrahydronaphthalen-2-yl)amino)-2-fluoro-benzoate (66)

Using a procedure similar to that described for the preparation of compound 36, the title compound 66 (1.0951 g, 91%) was prepared as a crystalline solid, m.p. 90.3-91.5° C.: $^1$H NMR (400 MHz, CDCl$_3$) δ 7.72 (t, J=8.8, 1H), 7.20 (s, 1H), 6.97 (s, 1H), 6.21 (d, J=8.4, 1H), 6.11 (d, J=14.8, 1H), 3.84 (s, 3H), 3.63 (br s, 2H), 2.03 (s, 3H), 1.69 (s, 4H), 1.30 (s, 6H), 1.24 (t, J=7.2, 3H), 1.23 (s, 6H); $^{13}$C NMR (100.6 MHz, CDCl$_3$) δ 165.3, 165.2, 165.1, 162.8, 153.6, 153.5, 144.6, 144.3, 140.3, 133.3, 133.2, 132.9, 129.4, 126.9, 107.3, 105.0, 104.9, 99.0, 98.7, 51.5, 46.1, 35.0, 34.9, 34.0, 34.0, 31.8, 17.3, 12.4; IR (neat) 2954, 1715, 1694, 1622, 1296, 1273 cm$^{-1}$; GC-MS (M+Na)+ calcd for C$_{25}$H$_{32}$FNO$_2$Na 420.2315, found 420.2321.

Example 11. 4-(3,5,5,8,8-pentamethyl-5,6,7,8-tetrahydronaphthalene-2-carbonyl)benzenesulfonic acid (31)

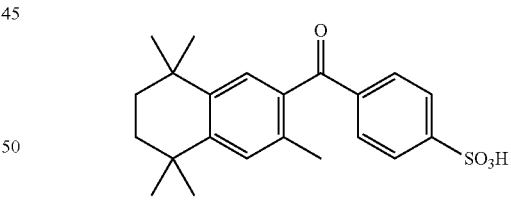

To a 20 dram vial charged with compound 69 (0.5621 g, 1.39 mmol) was added acetone (2.0 mL) and the vial was gently heated until the solution was homogeneous. To this solution of 69 in acetone was added a solution of potassium hydroxide (0.213 g, 3.80 mmol) in water (0.25 mL). The reaction was stirred and gently warmed to keep the solution homogeneous for 30 min at which point the reaction was quenched with 20% HCl (20 mL) and extracted with ethyl acetate (50 mL, thrice). The combined organic layers were washed with water (50 mL) and then brine (50 mL), dried over sodium sulfate, filtered, and concentrated in vacuo to give a crude produce that was purified by column chromatography (25 mL SiO$_2$, 10% methanol:ethyl acetate) to give 31 (0.300 g, 56%) as a white crystalline solid, decomp.

>200° C.: ¹H NMR (400 MHz, d6-DMSO) δ 7.75 (dd, J=6.4, 1.6, 2H), 7.66 (dd, J=6.4, 1.6, 2H), 7.30 (s, 1H), 7.21 (s, 1H), 2.21 (s, 3H), 1.65 (s, 4H), 1.28 (s, 6H), 1.18 (s, 6H); ¹³C NMR (100.6 MHz, d6-DMSO) δ 197.1, 152.3, 147.1, 141.4, 137.3, 135.3, 133.2, 129.4, 128.9, 127.0, 125.8, 34.4, 34.3, 33.9, 33.5, 31.4, 31.3, 19.3; IR (neat) 2925, 1673, 1191, 1123, 1038 cm⁻¹; ES-MS (M−H)− calcd for $C_{22}H_{25}SO_4$ 385.1474, found 385.1472. Anal. Calcd for $C_{22}H_{26}O_4S.(H_2O)_2$: C, 62.54; H, 7.16; S, 7.59. Found: C, 61.75; H, 6.76; S, 7.25.

The intermediate compound 69 was prepared as follows.

a. 4-(3,5,5,8,8-Pentamethyl-5,6,7,8-tetrahydronaphthalene-2-carbonyl)benzene-1-sulfonyl chloride (69)

A 100 mL round bottom flask was charged with potassium 4-carboxybenzenesulfonate (67) (1.61 g, 6.70 mmol), a few drops of DMF were added followed by thionyl chloride (11.0 mL, 151 mmol), and a reflux condenser fitted with a drying tube was attached and the heterogeneous reaction mixture was refluxed in an oil bath at 85° C. After 40 min at reflux, the reaction solution was homogeneous. After 1 hour at reflux, the reaction solution was cooled to room temperature, excess thionyl chloride was removed in vacuo, benzene (20 mL) was added and this was removed in vacuo, and the crude product (68) was dried on high vacuum for 10 minutes and used without further purification. To a 50 mL two-neck round bottom flask charged with 1,1,4,4,6-pentamethyl-1,2,3,4-tetrahydronaphthalene (40, 1.47 g, 7.26 mmol) was added a solution of compound 68 in 15 mL DCM followed by $AlCl_3$ (2.27 g, 17.0 mmol) in small portions. Upon the addition of aluminum chloride, the reaction solution boiled, and when the addition of aluminum chloride was complete, the reaction was refluxed in an oil bath at 55° C. for 15 minutes, cooled to room temperature and poured into an ice solution (25 mL) and 20% HCl (7 mL) was added. The layers were separated and the aqueous layer was extracted with ethyl acetate (50 mL, twice). The combined organic layers were dried over sodium sulfate, filtered, and concentrated in vacuo to yield a crude product that was purified by column chromatography (150 mL $SiO_2$, 5% ethyl acetate:hexanes) to give compound 69 (2.3592 g, 86%) as a yellow-brown crystalline solid, m.p. 111-114° C.: ¹H NMR (400 MHz, CDCl₃) δ 8.13 (d, J=8.8, 2H), 8.01 (d, J=8.4, 2H), 7.24-7.26 (m, 2H), 2.37 (s, 3H), 1.70 (s, 4H), 1.32 (s, 6H), 1.21 (s, 6H); ¹³C NMR (100.6 MHz, CDCl₃) δ 196.0, 149.2, 146.7, 144.0, 142.2, 135.0, 133.6, 131.0, 129.8, 128.7, 126.9, 34.8, 34.7, 34.4, 33.9, 31.7, 31.5, 20.1; IR (neat) 2928, 1661, 1374, 1256, 1186, 1174 cm⁻¹.

Example 12. 4-(1-(3,5,5,8,8-pentamethyl-5,6,7,8-tetrahydronaphthalen-2-yl)vinyl)benzenesulfonic acid (30)

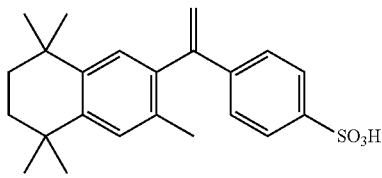 [SMILES: C=C(c1ccc(S(=O)(=O)O)cc1)c1cc2c(cc1C)C(C)(C)CCC2(C)C]

To a 100 mL round-bottomed flask equipped with a magnetic stir bar and charged with compound 71 (0.2046 g, 0.464 mmol) in methanol (3.0 mL) was added a solution of potassium hydroxide (0.0902 g, 1.61 mmol) in water (0.18 mL). The flask was fitted with a water condenser, and heated to reflux in an oil bath at 85° C. for 2 h. The reaction was cooled to room temperature and 20% HCl (30 mL) was added. The resulting solution was extracted with ethyl acetate (50 mL, twice), and the combined organic layers were dried over sodium sulfate, filtered, concentrated in vacuo and purified by column chromatography (25 mL $SiO_2$, 10% methanol:ethyl acetate) to give compound 30 (0.1436 g, 80%) as a white crystalline solid, decomp. >280° C.: ¹H NMR (400 MHz, d6-DMSO) δ 7.55 (d, J=8.4, 2H), 7.18 (d, J=8.4, 2H), 7.13 (s, 1H), 7.05 (s, 1H), 5.79 (d, J=1.2, 1H), 5.14 (d, J=1.2, 1H), 1.91 (s, 3H), 1.64 (s, 4H), 1.26 (s, 6H), 1.22 (s, 6H); ¹³C NMR (100.6 MHz, d6-DMSO) δ 148.5, 147.4, 143.5, 141.7, 140.2, 138.2, 132.1, 127.7, 127.2, 125.7, 125.4, 115.4, 34.7, 34.6, 33.6, 33.4, 31.7, 31.6, 19.5; IR (neat) 2961, 1455, 1179, 1043, 1008, 845, 669 cm⁻¹; ES-MS (M−H)− calcd for $C_{23}H_{27}SO_3$ 383.1681, found 383.1667. Anal. Calcd for $C_{23}H_{28}O_4S.(H_2O)_2$: C, 65.68; H, 7.67; S, 7.62. Found: C, 63.94; H, 7.35; S, 7.15.

The intermediate compound 71 was prepared as follows.

a. Isobutyl 4-(3,5,5,8,8-pentamethyl-5,6,7,8-tetrahydronaphthalene-2-carbonyl)benzene-sulfonate (70)

To a 20 dram vial charged with compound 69 (1.0064 g, 2.49 mmol) was added acetone (2.5 mL) and the solution was gently heated until it became homogenous. 2-Methyl-1-propanol (0.45 mL, 4.87 mmol) was added followed by triethylamine (0.40 mL, 2.87 mmol), and the reaction was gently warmed and stirred for 1 hour. TLC showed complete conversion, and the reaction solution was loaded directly onto a silica gel column (150 mL $SiO_2$, 2% ethyl acetate:hexanes) to give compound 70 (0.9568 g, 87%) as a white crystalline solid, m.p. 168-170° C.: ¹H NMR (400 MHz, CDCl₃) δ 8.00 (d, J=8.8, 2H), 7.94 (d, J=9.2, 2H), 7.24 (s, 1H), 7.22 (s, 1H), 3.87 (d, J=6.4, 2H), 2.35 (s, 3H), 1.95 (hept, J=6.8, 1H), 1.90 (s, 4H), 1.69 (s, 6H), 1.19 (s, 6H), 0.91 (d, J=6.8, 6H); ¹³C NMR (100.6 MHz, CDCl₃) δ 6196.7, 148.9, 142.8, 142.1, 139.4, 134.8, 134.0, 130.5, 129.6, 128.6, 127.7, 34.8, 34.7, 34.4, 33.9, 31.6, 31.5, 28.0, 20.1, 18.5; IR (neat) 2924, 1673, 1652, 1188 cm⁻¹; ES-MS (M+Na)+ calcd for $C_{26}H_{34}SO_4Na$ 465.2076, found 465.2069.

b. Isobutyl 4-(1-(3,5,5,8,8-pentamethyl-5,6,7,8-tetrahydronaphthalen-2-yl)vinyl)benzene-sulfonate (71)

To a flame-dried 100 mL round-bottomed flask was added THF (2.0 mL), isopropylamine (0.70 mL, 8.6 mmol) followed by 1.6 M n-butyllithium in hexanes (2.80 mL, 4.5 mmol) and the solution was stirred for 30 minutes. To this solution was added methyltriphenylphosphonium bromide (1.19 g, 3.33 mmol), and the reaction was stirred for 20 minutes and then added to a 20 dram vial containing a solution of compound 70 (0.89 g, 2.01 mmol) in THF (2.0 mL). The reaction was stirred for 1 hour, then poured into water (50 mL) and extracted with ethyl acetate (50 mL, twice). The combined organic layers were washed with brine, dried over sodium sulfate, filtered, and concentrated in vacuo to give a crude product that was run through a silica gel column (150 mL $SiO_2$, 1% ethyl acetate:hexanes) to give compound 71 with a 9 mol % contamination of triphenylphosphine oxide (0.8874 g, 48.9%) as a colorless, crystalline solid, m.p. 92-94° C.: ¹H NMR (400 MHz, CDCl₃) δ 7.83 (dd, J=6.8, 2.0, 2H), 7.44 (dd, J=6.8, 2.0, 2H), 7.12 (s, 1H), 7.09 (s, 1H), 5.84 (d, J=1.2, 1H), 5.39 (d, J=1.2, 1H), 3.81

(d, J=6.4, 1H) 1.97 (s, 3H), 1.95 (hept, J=6.8, 1H), 1.70 (s, 4H), 1.31 (s, 6H), 1.28 (s, 6H), 0.89 (d, J=6.4, 6H); IR (neat) 2960, 1673, 1190, 1039 cm$^{-1}$; ES-MS (M+Na)+ calcd for $C_{27}H_{36}SO_3Na$ 463.2283, found 463.2280.

Example 13. 2-(1-(1,1,3,3,6-pentamethyl-2,3-dihydro-1H-inden-5-yl)vinyl)pyrimidine-5-carboxylic acid (9)

To a solution of compound 20 (0.6637 g, 1.8938 mmols) in methanol (12.0 mL) in a 100

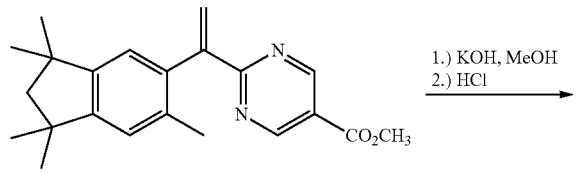

mL round bottom flask
was added a solution of potassium hydroxide (0.3032 g, 5.40 mmols) in water (0.45 mL). The resulting reaction solution was refluxed with stirring for 1 hr in an oil bath at 85° C. After cooling the reaction solution to room temperature, 1N HCl (90 mL) was added. The resulting precipitate was filtered and washed with cold water and dried to give crude 9 (0.6143 g, 96.4%). The crude 9 was dissolved in hot ethyl acetate (16.0 mL), hexanes (51 mL) was added, and the homogenous solution was concentrated, filtered and washed with hexanes to give pure 9 (0.3695 g, 58%) as a white solid (182.7-188.2° C.): $^1$H NMR (400 MHz, CDCl$_3$) δ 9.31 (s, 2H), 6.98 (s, 1H), 6.95 (s, 1H), 6.87 (d, J=2.0, 1H), 5.87 (d, J=1.6, 1H), 2.03 (s, 3H), 1.91 (s, 2H), 1.30 (s, 12H); $^{13}$C NMR (100.6 MHz, CDCl$_3$) δ 169.0, 168.0, 158.8, 151.1, 148.9, 148.3, 137.2, 134.2, 127.5, 124.0, 123.9, 120.7, 56.8, 42.4, 42.3, 31.5, 31.4, 20.3; IR (neat) 2954.25-2860.61 cm$^{-1}$, 1715.85 cm$^{-1}$, 802.43-760.52 cm$^{-1}$.

The intermediate compound 20 was prepared as follows.

a. 1,1,3,3,5-pentamethyl-2,3-dihydro-1H-indene (14)

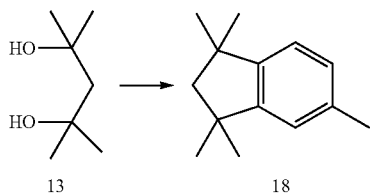

To 2,4-dimethylpentane-2,4-diol (5.00 g, 37.8 mmols) in a 100 mL round bottom flask was added concentrated hydrochloric acid (50.0 mL). The reaction was slightly diluted with water and extracted with hexanes. The hexanes was concentrated and the crude product was run through a column of silica gel (25 mL) in hexanes. The fractions containing the product were combined and concentrated to give crude 2,4-dichloro-2,4-dimethylpentane as a colorless oil (2.94 g, 46%) that was used without further purification. The crude 2,4-dichloro-2,4-dimethylpentane (2.94 g, 17.4 mmols) was dissolved in dichloromethane (10.0 mL) in a 100 mL round bottom flask and toluene (18.2 mL) was added. To this solution was slowly added aluminum chloride (1.80 g). The reaction was stirred at reflux in an oil bath for 15 minutes, then cooled to room temperature and poured into ice. The organics were extracted with ethyl acetate, and the organic layers were dried over sodium sulfate, filtered and concentrated to give a crude oil that was purified by column chromatography (silica gel; hexanes) to give compound 14 (3.024 g, 92%) as a colorless oil: $^1$H NMR (400 MHz, CDCl$_3$) δ 7.03-7.04 (m, 2H), 6.95 (s, 1H), 2.37 (s, 3H), 1.93 (s, 2H), 1.32 (s, 6H), 1.31 (s, 6H).

b. Methyl 2-(1,1,3,3,6-pentamethyl-2,3-dihydro-1H-indene-5-carbonyl)pyrimidine-5-carboxylate (19)

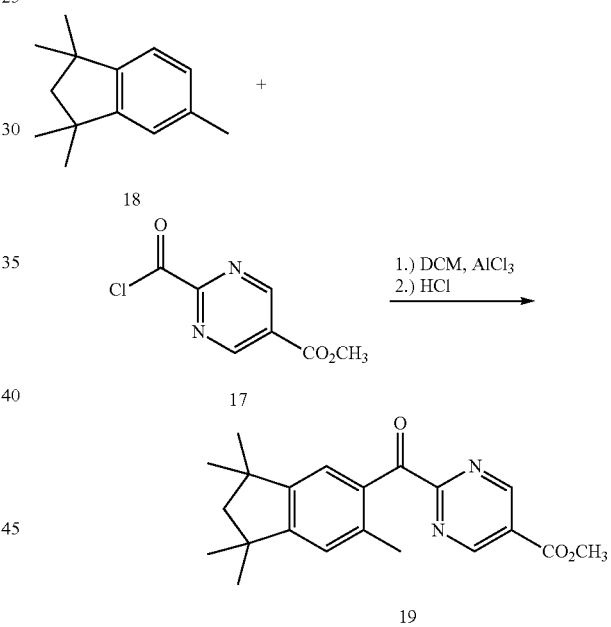

To a solution of compound 18 (3.05 g, 16.0 mmols) and methyl 2-(chlorocarbonyl)pyrimidine-5-carboxylate 17 (3.19 g, 15.9 mmols) in dichloromethane (35 mL) in a 100 mL round bottom flask was slowly added aluminum chloride (5.6 g) and the resulting mixture was stirred in an oil bath at reflux for 15 minutes. The reaction solution was cooled to room temperature and quenched by pouring onto 100 mL of an ice water solution. The solution was extracted with ethyl acetate, and the combined organic layers were dried over sodium sulfate, filtered and concentrated to give a crude product that was purified by column chromatography (silica gel; 1:9 ethyl acetate:hexanes to 1:4 ethyl acetate:hexane) to give compound 19 (1.5869 g, 28%) as an orange, crystalline solid (98.1-103.2° C.): $^1$H NMR (400 MHz, CDCl$_3$) δ 9.42 (s, 2H), 7.17 (s, 1H), 7.03 (s, 1H), 4.02 (s, 3H), 2.44 (s, 3H), 1.92 (s, 2H), 1.31 (s, 6H), 1.23 (s, 6H); $^{13}$C NMR (100.6 MHz, CDCl$_3$) δ 6193.2, 166.0, 163.5, 158.5, 156.6, 148.6, 138.9, 133.5, 126.1, 126.0, 124.1, 56.5, 52.9, 42.8, 42.2, 31.3, 31.1, 21.3; IR (neat) cm$^{-1}$.

c. Methyl 2-(1-(1,1,3,3,6-pentamethyl-2,3-dihydro-1H-inden-5-yl)vinyl)pyrimidine-5-carboxylate (20)

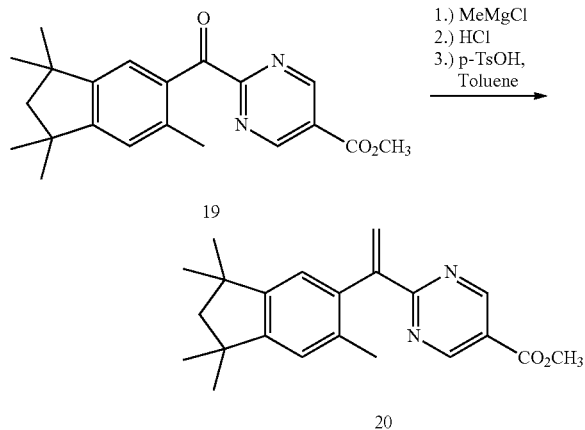

A solution of compound 19 (2.18 g, 6.18 mmols) in toluene (22.0 mL) in a 100 mL round bottom flask was cooled to −10° C. under nitrogen with stirring and a 3.0 M solution methyl magnesium chloride (2.72 mL, 8.16 mmols) was added dropwise. After 15 min. of stirring, the reaction solution was warmed to room temperature and stirred for an additional 35 minutes. The reaction mixture was then quenched by the slow addition of 1.0 N hydrochloric acid (14.0 mL, 14.0 mmols). The mixture was extracted with ethyl acetate, and the organic layers were washing with water and saturated sodium chloride, then dried over sodium sulfate, filtered and concentrated in a 300 mL round bottom flask to give a crude alcohol product that was used without further purification. The alcohol product was dissolved in toluene (98.0 mL) and p-TsOH.H$_2$O (1.197 g,) was added, and the reaction flask was fitted with a Dean Stark trap and a water condenser. The vessel was evacuated and back-filled with nitrogen three times, and then heated to reflux in an oil bath at 130° C. and stirred for 3 hours, during which time water collected in the Dean Stark trap. The reaction was cooled to room temperature, poured into water, and extracted with ethyl acetate. The combined organic layers were dried over sodium sulfate, filtered and concentrated to give a crude product that was purified by column chromatography (silica gel; 2.5% ethyl acetate: hexanes to 5% ethyl acetate:hexanes) to give compound 20 (0.7969 g, 36.8%) as a white solid (182.9-185.5° C.): $^1$H NMR (400 MHz, CDCl$_3$) δ 9.25 (s, 2H), 6.98 (s, 1H), 6.94 (s, 1H), 6.84 (d, J=2.0, 1H), 5.81 (d, J=2.0, 1H), 3.96 (s, 3H), 2.02 (s, 3H), 1.92 (s, 2H), 1.33 (s, 6H), 1.31 (s, 6H); $^{13}$C NMR (100.6 MHz, CDCl$_3$) δ168.7, 164.3, 158.2, 150.9, 148.8, 148.7, 137.6, 134.2, 126.6, 123.9, 123.8, 121.1, 56.9, 52.5, 42.4, 42.3, 31.6, 31.5, 20.3; IR (neat) 2953.18 cm$^{-1}$, 1722.25 cm$^{-1}$, 835.65-761.01 cm$^{-1}$.

Example 14. 2-(1-(1,1,3,3,6-pentamethyl-2,3-dihydro-1H-inden-5-yl)cyclopropyl)-pyrimidine-5-carboxylic acid (10)

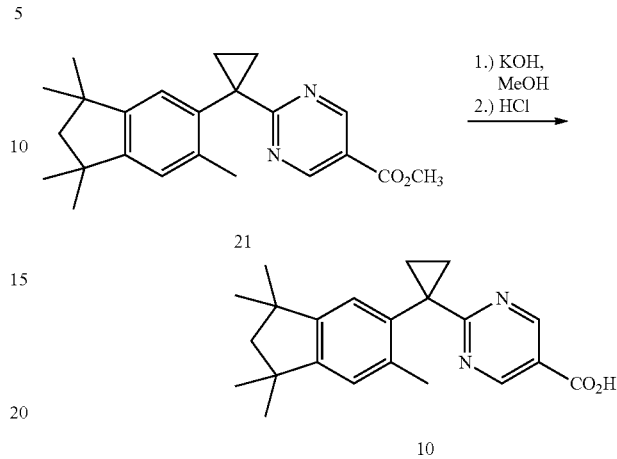

To a solution of 21 (0.5324 g, 1.4607 mmols) in methanol (9.4 mL) in a 100 mL round bottom flask was added a solution of potassium hydroxide (0.2492 g, 4.44 mmols) in water (0.34 mL). The resulting reaction solution was refluxed with stirring for 1 hr in an oil bath at 85° C. After cooling the reaction solution to room temperature, 1N HCl (90 mL) was added. The resulting precipitate was filtered and washed with cold water and dried to give crude 10 (0.4932 g, 96.3%). The crude 10 was dissolved in hot ethyl acetate (28.0 mL), hexanes (20 mL) was added, and the homogenous solution was concentrated, filtered and washed with hexanes to give pure 10 (0.3402 g, 66%) as a white solid (261.6-267.3° C.): $^1$H NMR (400 MHz, CDCl$_3$) δ 9.12 (s, 2H), 7.05 (s, 1H), 6.92 (s, 1H), 2.17 (s, 3H), 1.93 (m, 2H), 1.89 (s, 2H), 1.53 (m, 2H), 1.29 (s, 6H), 1.28 (s, 6H); $^{13}$C NMR (100.6 MHz, CDCl$_3$) δ 177.1, 167.3, 159.0, 158.5, 158.4, 150.4, 148.9, 137.3, 124.7, 124.1, 119.7, 56.8, 42.4, 42.3, 32.0, 31.6, 31.5, 31.4, 23.9, 22.8, 19.8; IR (neat) 2954.58 cm$^{-1}$, 1721.16-1679.81 cm$^{-1}$, 832.05-715.76 cm$^{-1}$.

The intermediate compound 21 was prepared as follows.

a. Methyl 2-(1-(1,1,3,3,6-pentamethyl-2,3-dihydro-1H-inden-5-yl)cyclopropyl)-pyrimidine-5-carboxylate (21)

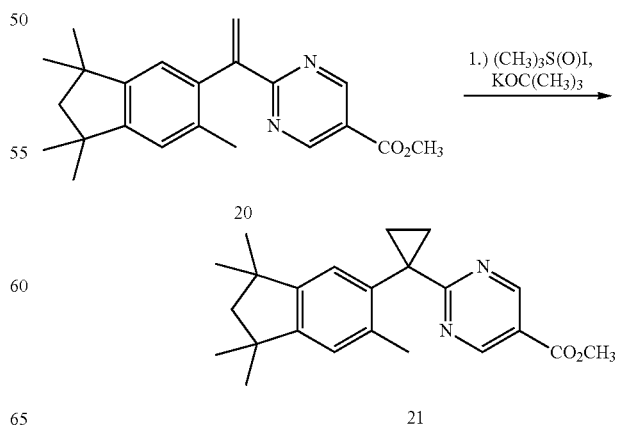

To a suspension of trimethylsulfoxonium iodide (0.760 g, 3.45 mmols) in DMSO (2.5 mL) in a 50 mL 2-neck round bottom flask was added a 20 wt % solution of potassium tert-butoxide in THF (1.94 mL, 3.45 mmols) with stirring at 35° C. The reaction mixture was stirred for 5 minutes and then a solution of 20 (0.8061 g, 2.30 mmols) in THF (9.9 mL) was added. The reaction was stirred for 1 hour at 35° C., then allowed to cool to room temperature at which point 1N hydrochloric acid (10.0 mL) was added. The resulting solution was extracted with ethyl acetate, the combined organic layers were washed with saturated sodium chloride, dried over sodium sulfate, filtered and concentrated to give a crude off-white solid that was purified by column chromatography (silica gel; 2.5% ethyl acetate:hexanes to 10% ethyl acetate:hexanes) to give compound 21 (0.6009 g, 71.7%) as a white solid (236.4-242.4° C.): $^1$H NMR (400 MHz, CDCl$_3$) δ 9.08 (s, 2H), 7.06 (s, 1H), 6.92 (s, 1H), 3.92 (s, 3H), 2.16 (s, 3H), 1.91 (s, 2H), 1.90 (t, J=2.8, 2H), 1.49 (t, J=3.2, 2H), 1.32 (s, 6H), 1.29 (s, 6H); $^{13}$C NMR (100.6 MHz, CDCl$_3$) δ 176.8, 164.6, 157.8, 149.8, 148.5, 138.2, 137.3, 124.5, 123.8, 119.9, 56.9, 52.3, 42.3, 42.2, 32.0, 31.6, 31.5, 23.8, 21.8, 19.8; IR (neat) 2963.25-2861.11 cm$^{-1}$, 1680.91 cm$^{-1}$, 836.07-794.93 cm$^{-1}$.

Example 15. 2-(1-(5,5,8,8-tetramethyl-5,6,7,8-tetrahydronaphthalen-2-yl)vinyl)pyrimidine-5-carboxylic acid (11)

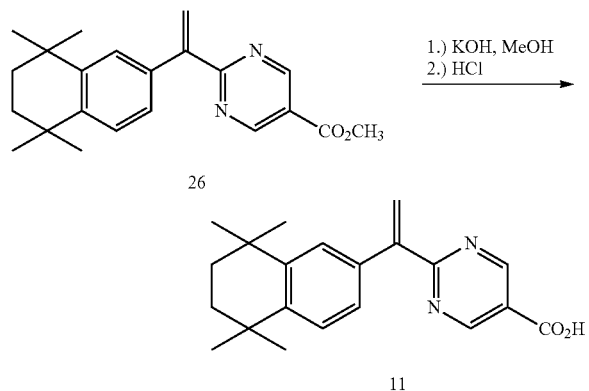

To a solution of 26 (0.6585 g, 1.879 mmols) in methanol (12.0 mL) in a 100 mL round bottom flask was added a solution of potassium hydroxide (0.3046 g, 5.43 mmols) in water (0.45 mL). The resulting reaction solution was refluxed with stirring for 1 hr in an oil bath at 85° C. After cooling the reaction solution to room temperature, 1N HCl (90 mL) was added. The resulting precipitate was filtered and washed with cold water and dried to give crude 11 (0.5526 g, 87%). The crude 11 was dissolved in hot ethyl acetate (17.0 mL), hexanes (50 mL) was added, and the homogenous solution was concentrated, filtered and washed with hexanes to give pure 11 (0.2572 g, 40%) as a white solid (224.0-227.8° C.): $^1$H NMR (400 MHz, CDCl$_3$) δ 9.35 (s, 2H), 7.35 (d, J=1.6, 1H), 7.32 (d, J=8.0, 1H), 7.17 (dd, J=8.4, 2.0, 1H), 6.62 (d, J=1.2, 1H), 5.98 (d, J=1.6, 1H), 1.69 (s, 4H), 1.29 (s, 6H), 1.28 (s, 6H); $^{13}$C NMR (100.6 MHz, CDCl$_3$) δ 169.4, 158.7, 147.5, 144.9, 144.5, 135.3, 126.8, 126.3, 125.8, 125.2, 120.7, 35.1, 35.0, 34.2, 34.1, 31.8, 31.7; IR (neat) 3009.82-2860.48 cm$^{-1}$, 1715.95 cm$^{-1}$, 802.26-760.40 cm$^{-1}$.

The intermediate compound 26 was prepared as follows.

a. 1,1,4,4-tetramethyl-1,2,3,4-tetrahydronaphthalene (24)

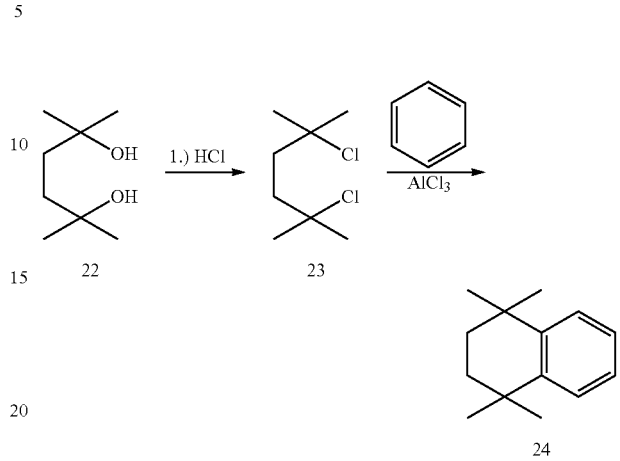

The procedure of Bruson and Kroeger (Bruson, H. A., et al., *J. Am. Chem. Soc.* 1940, 62, 36-44) was followed. To a solution of 2,5-dichloro-2,5-dimethylhexane (11.36 g, 62.04 mmols) in benzene (280 mL) was added aluminum chloride (1.5 g) in a 500 mL round bottom flask equipped with a stir bar and water condenser and the reaction was heated to 75-82° C. for 24 hours with stirring under nitrogen. After cooling to room temperature, the reaction solution was poured into 1N HCl (450 mL) and extracted with benzene. The combined organic layers were washed with water, saturated sodium bicarbonate, water and finally saturated sodium chloride. The combined organic layers were dried over sodium sulfate, concentrated to a crude oil that was then vacuum distilled with a short-path distillation head at an oil bath temperature of 95-100° C., and a head temperature of 78° C. for the major fraction, at 0.2-0.3 mm Hg to give compound 24 as a colorless oil: $^1$H NMR (400 MHz, CDCl$_3$) δ 7.35 (m, 2H), 7.16 (m, 2H), 1.72 (s, 4H), 1.32 (s, 12H); $^{13}$C NMR (100.6 MHz, CDCl$_3$) δ 144.7, 126.4, 125.5, 35.0, 34.1, 31.8; IR (neat) 3021.70-2860.29 cm$^{-1}$, 1715.96 cm$^{-1}$, 754.34 cm$^{-1}$.

b. Methyl 2-(5,5,8,8-tetramethyl-5,6,7,8-tetrahydronaphthalene-2-carbonyl)pyrimidine-5-carboxylate (25)

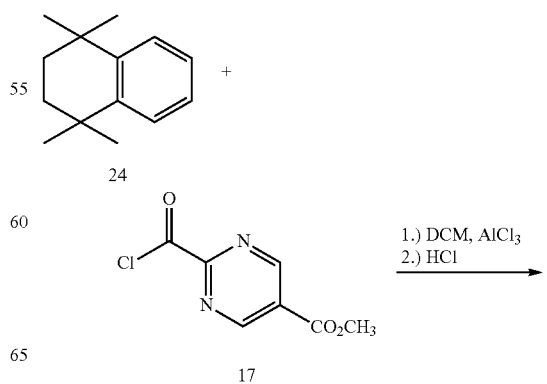

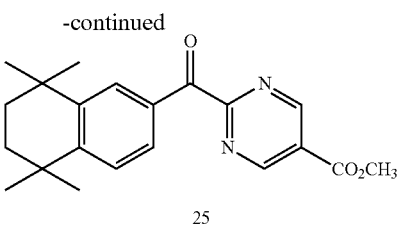

To a solution of compound 24 (5.3945 g, 28.646 mmols) and compound 17 (5.37 g, 26.772 mmols) in dichloromethane (60 mL) was slowly added aluminum chloride (8.8 g) and the resulting mixture was stirred at reflux in an oil bath at 55° C. for 15 minutes. The solution was then cooled to room temperature and poured into 200 mL of an ice water solution. The resulting mixture was extracted with ethyl acetate. The combined organic layers were washed with saturated sodium chloride, dried over sodium sulfate, filtered, and concentrated to give a crude product that was purified by column chromatography (silica gel; 15% ethyl acetate:hexanes to 20% ethyl acetate:hexanes) to give compound 25 as a bright canary yellow crystalline solid (79.1-83.4° C.): $^1$H NMR (400 MHz, CDCl$_3$) δ 9.43 (s, 2H), 8.02 (d, J=1.6, 1H), 7.63 (dd, J=7.6, 2.0, 1H), 7.39 (d, J=8.0, 1H), 4.03 (s, 3H), 1.70 (s, 4H), 1.29 (s, 12H); $^{13}$C NMR (100.6 MHz, CDCl$_3$) δ 190.3, 165.3, 163.5, 158.3, 152.1, 145.5, 131.9, 129.3, 128.0, 126.7, 124.1, 52.9, 34.8, 34.7, 34.6, 34.4, 31.7, 31.5; IR (neat) 2954.21 cm$^{-1}$, 1721.92-1675.86 cm$^{-1}$, 832.17-715.12 cm$^{-1}$.

c. methyl 2-(1-(5,5,8,8-tetramethyl-5,6,7,8-tetrahydronaphthalen-2-yl)vinyl)pyrimidine-5-carboxylate (26)

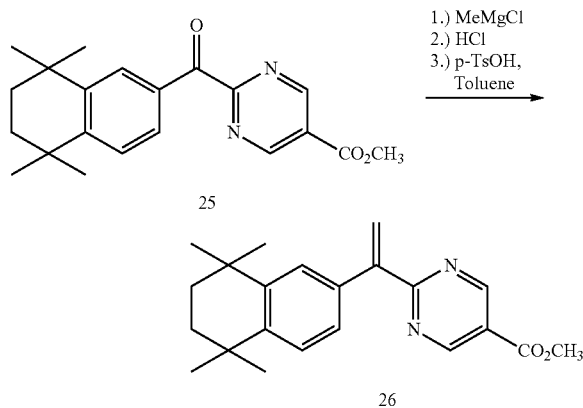

A solution of compound 25 (5.2603 g, 14.926 mmols) in toluene (53.0 mL) in a 250 mL round bottom flask was cooled to −10° C. under nitrogen with stirring and a 3.0 M solution methyl magnesium chloride (6.56 mL, 19.68 mmols) was added dropwise. After 15 minutes of stirring, the reaction solution was warmed to room temperature and stirred for an additional 35 minutes. The reaction mixture was then quenched by the slow addition of 1.0 N hydrochloric acid (35.0 mL, 35.0 mmols). The mixture was extracted with ethyl acetate, and the organic layers were washing with water and saturated sodium chloride, then dried over sodium sulfate, filtered and concentrated in a 300 mL round bottom flask to give a crude alcohol product that was used without further purification. The alcohol product was dissolved in toluene (110.0 mL) and p-TsOH.H$_2$O (5.7782 g,) was added, and the reaction flask was fitted with a Dean Stark trap and a water condenser. The vessel was evacuated and back-filled with nitrogen three times, and then heated to reflux in an oil bath at 130° C. and stirred for 3 hours, during which time water collected in the Dean Stark trap. The reaction was cooled to room temperature, poured into water, and extracted with ethyl acetate. The combined organic layers were dried over sodium sulfate, filtered and concentrated to give a crude product that was purified by column chromatography (silica gel; 2.5% ethyl acetate:hexanes to 5% ethyl acetate:hexanes) to give compound 26 (0.2936 g, 5.6%) as a white solid (171.3-174.1° C.): $^1$H NMR (400 MHz, CDCl$_3$) δ 9.28 (s, 2H), 7.35 (d, J=2.0, 1H), 7.31 (d, J=8.0, 1H), 7.17 (dd, J=8.4, 2.0, 1H), 6.58 (d, J=1.6, 1H), 5.93 (d, J=1.6, 1H), 3.98 (s, 3H), 1.70 (s, 4H), 1.30 (s, 6H), 1.28 (s, 6H); $^{13}$C NMR (100.6 MHz, CDCl$_3$) δ 168.9, 164.3, 158.0, 147.7, 144.7, 144.4, 135.5, 126.8, 126.2, 125.8, 124.4, 121.5, 52.5, 36.6, 35.1, 35.0, 34.2, 34.1, 31.8, 31.7, 24.6; IR (neat) 2952.33 cm$^{-1}$, 1721.95 cm$^{-1}$, 832.49-758.25 cm$^{-1}$.

Example 16. 2-(1-(5,5,8,8-tetramethyl-5,6,7,8-tetrahydronaphthalen-2-yl)cyclopropyl)pyrimidine-5-carboxylic acid (12)

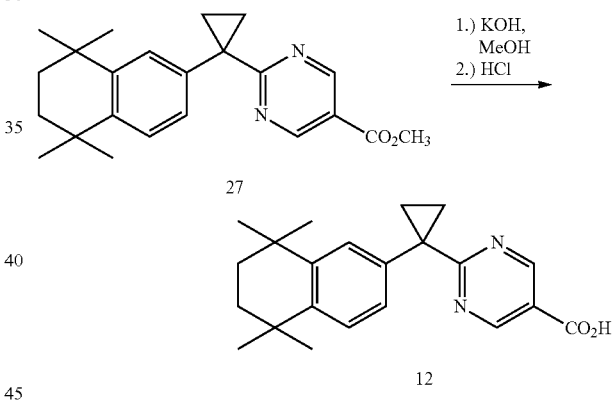

To a solution of compound 27 (0.1316 g, 0.361 mmols) in methanol (2.5 mL) in a 100 mL round bottom flask was added a solution of potassium hydroxide (0.0803 g, 1.43 mmols) in water (0.18 mL). The resulting reaction solution was refluxed with stirring for 1 hour in an oil bath at 85° C. After cooling the reaction solution to room temperature, 1N HCl (70 mL) was added. The resulting precipitate was filtered and washed with cold water and dried to give crude 12 (0.1041 g, 82%). The crude 12 was dissolved in hot ethyl acetate (5.0 mL), and the homogenous solution was concentrated, filtered and washed with hexanes to give compound 12 (0.0734 g, 58%) as a white solid (251.5-254.6°): $^1$H NMR (400 MHz, CDCl$_3$) δ 9.13 (s, 2H), 7.30 (d, J=1.6, 1H), 7.29 (d, J=8.4, 1H), 7.15 (dd, J=8.0, 2.0, 1H), 1.81 (m, 2H), 1.68 (s, 4H), 1.53 (m, 2H), 1.28 (s, 6H), 1.26 (s, 6H); $^{13}$C NMR (100.6 MHz, CDCl$_3$) δ 177.6, 167.7, 158.8, 158.3, 144.7, 143.4, 137.6, 128.9, 127.8, 126.4, 119.4, 35.1, 35.0, 34.2, 34.0, 33.2, 31.9, 31.8, 20.9, 20.9; IR (neat) 2957.90-2856.45 cm$^{-1}$, 1679.64 cm$^{-1}$, 798.85-741.51 cm$^{-1}$.

The intermediate compound 27 was prepared as follows.

a. Methyl 2-(1-(5,5,8,8-tetramethyl-5,6,7,8-tetrahydronaphthalen-2-yl)cyclopropyl)pyrimidine-5-carboxylate (27)

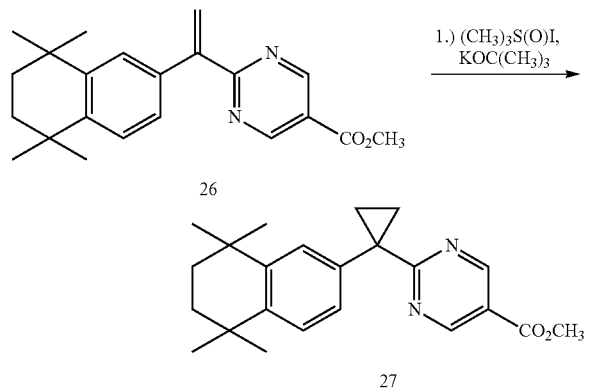

To a suspension of trimethylsulfoxonium iodide (0.3204 g, 1.45 mmols) in DMSO (1.05 mL) in a 50 mL 2-neck round bottom flask was added a 20 wt % solution of potassium tert-butoxide in THF (0.84 mL, 1.49 mmols) with stirring at 35° C. The reaction mixture was stirred for 5 minutes and then a solution of compound 26 (0.3408 g, 0.97 mmols) in THF (4.8 mL) was added. The reaction was stirred for 1 hour at 35° C., then allowed to cool to room temperature at which point 1N hydrochloric acid (5.0 mL) was added. The resulting solution was extracted with ethyl acetate, the combined organic layers were washed with saturated sodium chloride, dried over sodium sulfate, filtered and concentrated to give a crude off-white solid that was purified by column chromatography (silica gel; 2.5% ethyl acetate:hexanes to 10% ethyl acetate:hexanes) to give compound 27 (0.1533 g, 43%) as a white solid (168.7-171.8° C.): $^1$H NMR (400 MHz, CDCl$_3$) δ 9.08 (s, 2H), 7.30 (d, J=1.6, 1H), 7.27 (d, J=8.0, 1H), 7.15 (dd, J=8.0, 2.0, 1H), 3.92 (s, 3H), 1.79 (m, 2H), 1.68 (s, 4H), 1.50 (m, 2H), 1.29 (s, 6H), 1.26 (s, 6H); $^{13}$C NMR (100.6 MHz, CDCl$_3$) δ 177.0, 164.6, 157.7, 144.5, 143.1, 138.2, 129.5, 128.8, 127.6, 126.2, 120.4, 120.0, 115.2, 52.4, 36.5, 35.1, 35.0, 34.2, 34.0, 33.0, 31.8, 24.6, 20.2; IR (neat) 2954.32-2859.83 cm$^{-1}$, 1721.02 cm$^{-1}$, 832.0-758.90 cm$^{-1}$.

Example 17. 2-Fluoro-4-(1-(5,5,8,8-tetramethyl-5,6,7,8-tetrahydronaphthalen-2-yl)vinyl)benzoic acid (5)

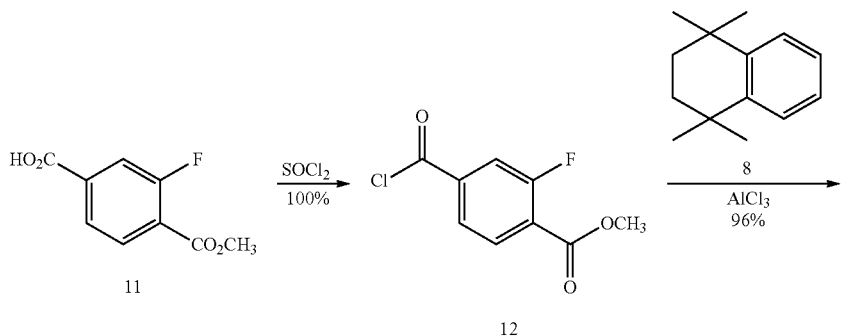

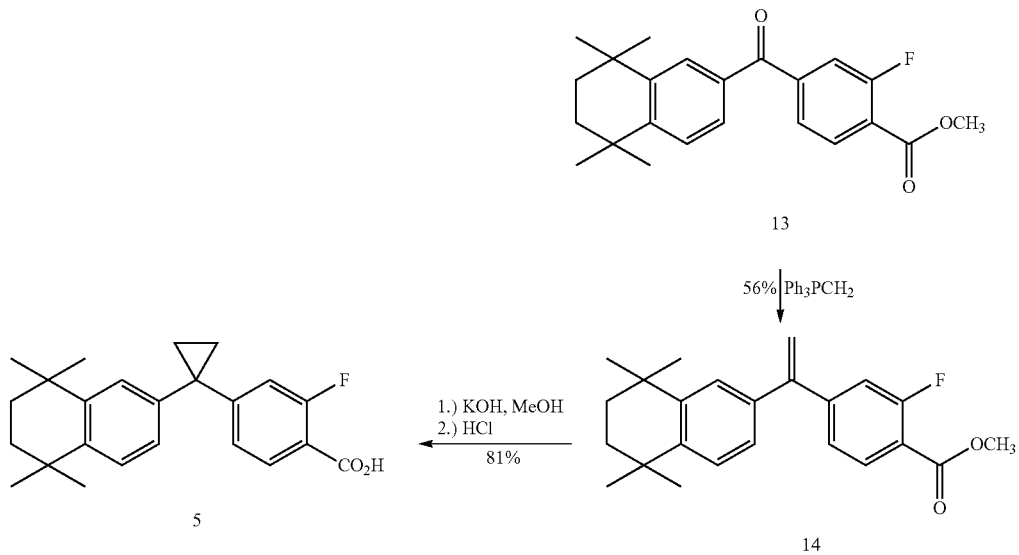

To a suspension of compound 14 (2.0486 g) in methanol (36.0 mL) was added a solution of potassium hydroxide (0.9348 g) in water (1.34 mL). The reaction was refluxed, following thin layer chromatography. After 70 minutes of reflux, the solution was cooled to room temperature and quenched by pouring into 1N hydrochloric acid (500 mL) to give a precipitate that was filtered to give crude 5 (1.75236 g), which was purified by column chromatography (150 mL SiO$_2$) 50% ethyl acetate/hexane to give compound 5 (1.5974 g, 81.0%) as a white solid, mp 172.5-183.0° C.: 1H NMR (400 MHz, CDCl3) δ 8.01 (t, J=8.0, 1H), 7.29 (d, J=8.4, 1H), 7.27 (dd, J=8.4, 1.6, 1H), 7.23 (d, J=2.0, 1H), 7.18 (dd, J=12.0, 1.6, 1H), 7.06 (dd, J=8.4, 2.0, 1H), 5.58 (d, J=0.4, 1H), 5.54 (d, J=0.4, 1H), 1.70 (s, 4H), 1.31 (s, 6H), 1.26 (s, 6H); 13C NMR (100.6 MHz, CDCl3) δ 169.5, 169.4, 163.8, 161.2, 149.7, 149.6, 148.2, 148.2, 145.1, 144.9, 136.8, 132.4, 126.5, 126.3, 125.3, 123.9, 123.8, 116.8, 116.6, 116.3, 116.3, 116.2, 116.1, 35.0, 34.9, 34.2, 34.1, 31.8, 31.7.

The intermediate compound 14 was prepared as follows.

a. Methyl 2-fluoro-4-(5,5,8,8-tetramethyl-5,6,7,8-tetrahydronaphthalene-2-carbonyl)benzoate (13)

To a 250 mL flask, 2-fluoro-terephthalic acid 4-methyl ester (11) (2.4067 g) was treated with thionyl chloride (20.0 mL), resulting in 100% yield. Furthermore, compound (8) (2.68 g) was combined utilizing aluminum chloride (4.24 g), benzene (20 mL) and DCM (30.0 mL) in a 250 mL flask, and left for 15 minutes. Thin layer chromatography was performed (300 mL SiO$_2$) inside a column with the addition of 2.5% ethyl acetate/hexane; 7.5% ethyl acetate/hexane; 20% ethyl acetate/hexane resulting in a pure ketone product (13) (4.2930 g, 96.0%) as white solid, mp 90.4-97.3° C.: 1H NMR (400 MHz, CDCl3) δ 8.04 (dd, J=8.0, 7.2, 1H), 7.78 (d, J=2.0, 1H), 7.58 (dd, J=8.0, 1.6, 1H), 7.56-7.50 (m, 2H), 7.41 (d, J=8.0, 1H), 3.97 (s, 3H), 1.72 (s, 4H), 1.31 (s, 6H), 1.29 (s, 6H); 13C NMR (100.6 MHz, CDCl3) δ 194.3, 194.2, 164.3, 164.3, 162.7, 160.1, 151.1, 145.5, 143.6, 143.6, 133.5, 132.0, 128.8, 127.2, 126.8, 124.9, 124.9, 121.4, 121.3, 118.2, 112.0, 52.6, 34.8, 34.7, 34.6, 34.4, 31.7, 31.5 b. Methyl 2-fluoro-4-(1-(5,5,8,8-tetramethyl-5,6,7,8-tetrahydronaphthalen-2-yl)vinyl)benzoate (14)

To a 250 mL flask charged with methyl 2-fluoro-4-(5,5,8,8-tetramethyl-5,6,7,8-tetrahydronaphthalene-2-carbonyl)benzoate (13) (3.988 g) and dry THF (25.0 mL) at room temperature was added a triphenylphosphonium methylide solution and the reaction was stirred for 1 hour. To synthesize the triphenylphosphonium methylide solution: a solution of diisopropylamine (3.3 mL) in THF (10 mL) was treated with 1.6M n-butyl lithium (13.5 mL) followed by methyltriphenylphosphonium bromide (5.75 g) and this solution was stirred for 1 hour. The reaction was monitored by TLC, and once complete was poured into water and extracted with ethyl acetate. The organic extracts were washed with water, dried over sodium sulfate and purified by column chromatography (150 mL SiO$_2$) with 2.5% ethyl acetate/hexanes to 5% ethyl acetate/hexane to give compound 14 (2.2275 g, 56.0%) as yellow solid, mp 80.8-96.5° C.: 1H NMR (400 MHz, CDCl3) δ 7.90 (t, J=8.0, 1H), 7.28 (d, J=8.0, 1H), 7.22 (dd, J=8.0, 1.6, 1H), 7.21 (d, J=2.0, 1H), 7.16 (dd, J=12.4, 1.6, 1H), 7.05 (dd, J=8.4, 2.0, 1H), 5.54 (d, J=0.8, 1H), 5.50 (d, J=0.8, 1H), 3.94 (s, 3H), 1.69 (s, 4H), 1.30 (s, 6H), 1.24 (s, 6H); 13C NMR (100.6 MHz, CDCl3) δ 164.8, 164.7, 163.0, 160.4, 148.5, 148.4, 148.3, 148.2, 145.0, 144.8, 136.9, 131.8, 126.5, 126.2, 125.3, 123.7, 123.7, 117.3, 117.2, 116.7, 116.4, 115.7, 52.2, 35.0, 34.9, 34.2, 34.1, 31.7.

Example 18. 2-Hydroxy-4-(1-(3,5,5,8,8-pentamethyl-5,6,7,8-tetrahydronaphthalen-2-yl)vinyl)benzoic acid (9)

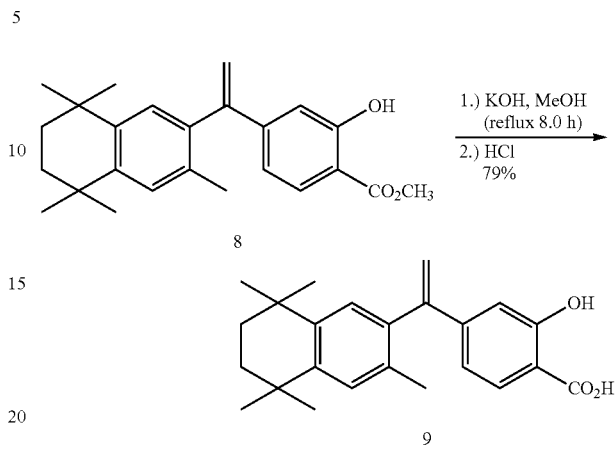

To a 100 mL round bottom flask containing a suspension of methyl 2-hydroxy-4-(1-(3,5,5,8,8-pentamethyl-5,6,7,8-tetrahydronaphthalen-2-yl)vinyl)benzoate (8) (0.3027 g, 0.800 mmols) in methanol (4.0 mL) was added a solution of potassium hydroxide (0.1634 g, 2.9 mmols) in water (0.20 mL), and the flask was fitted with a condenser and refluxed in an oil bath set to 85° C. for 1.2 h. The solution was cooled to room temperature and acidified with 1N hydrochloric acid (90 mL, 90 mmols), and the resulting precipitate was filtered and dried to give crude 9 (0.2380 g, 81.6%) as a white solid. This crude material was purified by column chromatography (25 mL SiO$_2$) with 40% ethyl acetate/hexanes to pure ethyl acetate to 8% methanol/ethyl acetate to give pure 9 (0.2316 g, 79%) as white solid, m.p. 220.4-224.9° C.: $^1$H NMR (400 MHz, CDCl3) δ 10.35 (br s, 1H), 7.85 (d, J=8.4, 1H), 7.11 (s, 1H), 7.07 (s, 1H), 6.92 (dd, J=8.4, 1.6, 1H), 6.86 (d, J=1.6, 1H), 5.84 (d, J=0.8, 1H), 5.36 (d, J=1.2, 1H), 1.96 (s, 3H), 1.69 (s, 4H), 1.30 (s, 6H), 1.27 (s, 6H); $^{13}$C NMR (100.6 MHz, CDCl3) δ 174.5, 162.1, 149.8, 148.8, 144.4, 142.3, 137.5, 132.6, 130.7, 128.0, 128.0, 118.0, 117.9, 115.7, 109.9, 35.2, 35.1, 33.9, 33.8, 31.9, 31.8, 19.8.

The intermediate compound 8 was prepared as follows.

a. Dimethyl-2-hydroxyterepthalate (2)

To a solution of hydroxyl-terepthalic acid (1) (9.93 g, 54.5 mmols) in methanol (189 mL) in a 500 mL round bottom flask equipped with a magnetic stir bar and cooled to 0° C. in an ice bath was added thionyl chloride (14.5 mL, 200 mmols) dropwise with stirring. After addition, the flask was equipped with a reflux condenser, placed under a nitrogen atmosphere, and warmed to reflux in an oil bath set at 85° C. and boiled for 2.5 hours. The solution was allowed to cool to room temperature, and most of the methanol was removed in vacuo. The crude product was dissolved in ethyl acetate, and the solvent was washed with water followed by brine and then dried over sodium sulfate. The solvent was filtered and the ethyl acetate was removed in vacuo to provide a crude product that was dissolved in warm ethyl acetate (20 mL) and purified by column chromatography (250 mL $SiO_2$) with 10% ethyl acetate/hexanes to give compound 2 (10.24 g, 90%) as white solid, m.p. 92.2-94.8° C.: $^1$H NMR (400 MHz, CDCl3) δ 10.75 (s, 1H), 7.89 (d, J=8.4, 1H), 7.62 (d, J=1.6, 1H), 7.51 (dd, J=8.4, 1.6, 1H), 3.97 (s, 3H), 3.92 (s, 3H); $^{13}$C NMR (100.6 MHz, CDCl3) δ 169.9, 165.9, 161.2, 136.3, 130.0, 119.6, 118.8, 115.6, 52.6, 52.4.

b. 3-Hydroxy-4-(methoxycarbonyl)benzoic acid (3)

Sodium hydroxide (0.7966 g, 19.9 mmols) was dissolved in water (32 mL), the solution was cooled to 0° C., and a finely ground powder of dimethyl-2-hydroxyterepthalate (2) (1.0119 g, 4.81 mmols) was added to the solution. The solution was stirred for 1.5 hours at 0° C., and then a solution of 1N hydrochloric acid was added (12 mL, 12 mmol) which brought the solution to pH=9.0, and the insoluble precipitate was filtered off. To the filtrate, an additional amount of 1N hydrochloric acid (9.5 mL, 9.5 mmol) was added that brought the pH=1.0 and the resulting precipitate was filtered and washed with cold water to give a crude product (0.67 g) that was purified by column chromatography (150 mL $SiO_2$) with 20% ethyl acetate/hexanes to 70% ethyl acetate/hexanes to give compound 3 (0.4606 g, 49%) as white solid, m.p. 213.7-216.2° C.: $^1$H NMR (400 MHz, CDCl3) δ 10.79 (s, 1H), 7.94 (d, J=8.0, 1H), 7.71 (d, J=1.6, 1H), 7.58 (dd, J=8.0, 1.6, 1H), 3.99 (s, 3H).

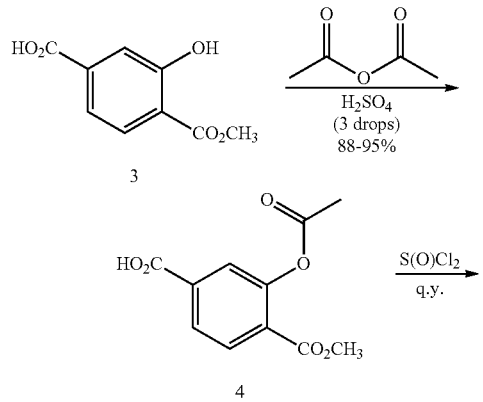

c. 3-Acetoxy-4-(methoxycarbonyl)benzoic acid (4)

To a solution of 3-hydroxy-4-(methoxycarbonyl)benzoic acid (3) (05328 g, 2.716 mmols) in acetic anhydride (20.0 mL) in 1 100 mL round bottom flask equipped with a stir bar was added concentrated sulfuric acid (3 drops) and the reaction was stirred in an oil bath at 45° C. for 40 minutes. The acetic anhydride was removed in vacuo and the crude oil was purified by column chromatography (150 mL $SiO_2$) with 10% ethyl acetate/hexanes to pure ethyl acetate to give compound 4 (0.5715 g, 88%) as white solid, m.p. 182.6-185.1° C.: $^1$H NMR (400 MHz, CDCl3) δ 8.10 (d, J=8.4, 1H), 8.03 (dd, J=8.4, 1.6, 1H), 7.84 (d, J=1.6, 1H), 3.91 (s, 3H), 2.38 (s, 3H); $^{13}$C NMR (100.6 MHz, CDCl3) δ 169.8, 169.5, 164.1, 150.5, 134.0, 131.9, 127.8, 127.4, 125.6, 52.6, 20.9.

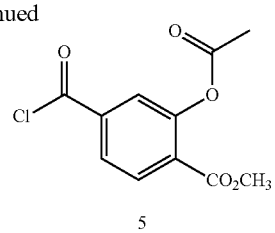

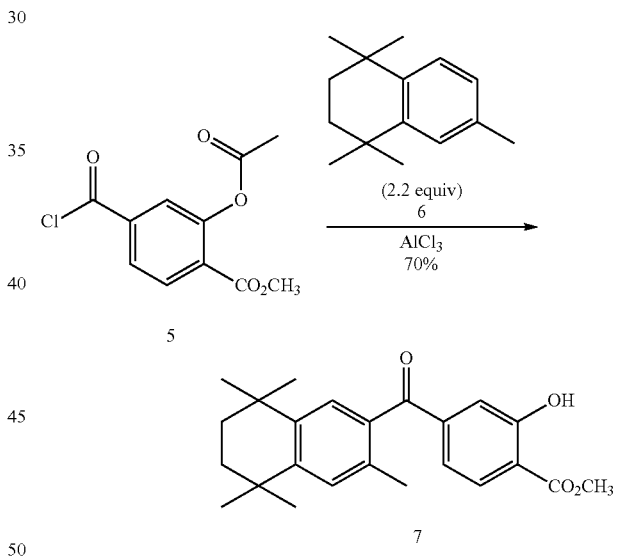

d. Methyl 2-hydroxy-4-(3,5,5,8,8-pentamethyl-5,6,7,8-tetrahydronaphthalene-2-carbonyl)benzoate (7)

To a 100 mL round bottom flask charged with 3-acetoxy-4-(methoxycarbonyl)benzoic acid (4) (3.236 g, 13.59 mmols) was added thionyl chloride (22 mL, 300 mmols) and a few drops of DMF. A water condenser was added to the flask, and the solution was refluxed in an oil bath for 1.2 hours to give methyl 2-acetoxy-4-(chlorocarbonyl)benzoate (5) in quantitative yield after the excess thionyl chloride was removed in vacuo. To the 100 mL round bottom flask containing compound 5 was added 1,1,4,4,6-pentamethyl-1,2,3,4-tetrahydronaphthalene (6) (6.0508 g, 29.9 mmols) and DCM (30 mL). To the resulting homogeneous solution was slowly added aluminum chloride (3.0 g) at room temperature, with the observed evolution of gas, and the reaction was refluxed for 15 minutes at 55° C. in an oil bath. The reaction solution was cooled to 0° C. in an ice bath and poured onto 100 mL of an ice water solution. The layers were separated, and the aqueous layer was extracted with ethyl acetate. The combined organic layers were washed with water and then brine, dried over sodium sulfate, filtered and concentrated in vacuo to give a crude product that was purified by column chromatography (250 mL $SiO_2$) with 1.5% to 5% ethyl acetate/hexanes to give compound 7 (3.64 g, 70%) as white solid, m.p. 104.2-106.3° C.: $^1$H NMR (400 MHz, CDCl3) δ 10.78 (s, 1H), 7.93 (d, J=8.0, 1H), 7.33 (d, J=1.2, 1H), 7.31 (dd, J=8.0, 1.6, 1H), 7.27 (s, 1H), 7.18 (s, 1H), 3.99 (s, 3H), 2.32 (s, 3H), 1.68 (s, 4H), 1.30 (s, 6H), 1.20 (s, 6H); $^{13}$C NMR (100.6 MHz, CDCl3) δ 197.5, 170.0, 161.3, 148.3, 144.5, 141.8, 134.5, 134.4, 129.9, 129.3, 128.3, 119.8, 119.4, 115.2, 52.6, 34.9, 34.8, 34.3, 33.8, 31.7, 31.6, 20.0.

e. Methyl 2-hydroxy-4-(1-(3,5,5,8,8-pentamethyl-5,6,7,8-tetrahydronaphthalen-2-yl)vinyl)benzoate (8)

To a 100 mL round bottom flask containing a solution of diisopropylamine (5.67 mL, 40.5 mmols) in THF (16.8 mL) was added a 1.6M solution of n-butyl lithium in hexanes (22.65 mL, 36.24 mmols) at room temperature, and the reaction was stirred for 15 minutes followed by the addition of methyl triphenylphosphonium bromide (9.7201 g, 27.21 mmols). After stirring this reaction for 1 hour, the resulting solution was added to a 100 mL round bottom flask contain a solution of methyl 2-hydroxy-4-(3,5,5,8,8-pentamethyl-5,6,7,8-tetrahydronaphthalene-2-carbonyl)benzoate (7) (3.8134 g, 10.02 mmols) in THF (8.86 mL) and the resulting reaction solution was stirred for 1 hour, poured into 1N hydrochloric acid (150 mL, 150 mmols) and extracted with ethyl acetate. The combined organic layers were washed with water and brine, dried over sodium sulfate, filtered and concentrated in vacuo to give a crude product that was purified by column chromatography (150 mL $SiO_2$) with 1.5% to 5% ethyl acetate/hexanes to give a mixture of spots containing 8 and this mixture was again purified by column chromatography (250 mL $SiO_2$) with 1% to 2% ethyl acetate/hexanes to give compound 8 (1.2997 g, 34%) as white solid, m.p. 103.6-106.6° C.: $^1$H NMR (400 MHz, CDCl3) δ 10.74 (s, 1H), 7.76 (d, J=8.4, 1H), 7.11 (s, 1H), 7.06 (s, 1H), 6.88 (dd, J=8.4, 1.6, 1H), 6.84 (d, J=2.0, 1H), 5.81 (d, J=1.2, 1H), 5.33 (d, J=1.2, 1H), 3.94 (s, 3H), 1.96 (s, 3H), 1.69 (s, 4H), 1.30 (s, 6H), 1.27 (s, 6H).

Example 19

The following illustrate representative pharmaceutical dosage forms, containing a compound of the invention, or a salt thereof ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 Ml |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula Ia:

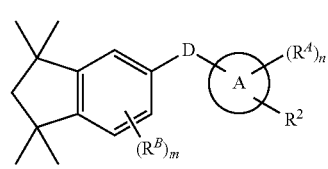

wherein:
D is

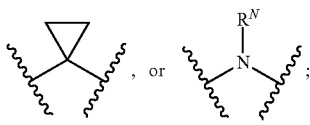, or ;

$R^N$ is $(C_3-C_6)$cycloalkyl, or $(C_2-C_6)$alkynyl, wherein the $(C_3-C_6)$cycloalkyl, and $(C_2-C_6)$alkynyl are optionally substituted with one or more groups independently selected from halo, hydroxy, nitro, and cyano;
$R^2$ is —COOH, —B(OH)$_2$, or —SO$_3$H;
ring A is phenyl or 6-membered heteroaryl;
each $R^A$ is independently selected from the group consisting of halo, hydroxy, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, wherein the $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy are optionally substituted with one or more groups independently selected from halo, hydroxy, nitro, cyano, $(C_1-C_6)$alkoxy, and oxo (=O);
each $R^B$ is independently selected from the group consisting of halo, hydroxy, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, wherein the $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy are optionally substituted with one or more groups independently selected from halo, hydroxy, nitro, cyano, $(C_1-C_6)$alkoxy, and oxo (=O);
n is 0, 1, 2, 3, or 4; and
m is 0, 1, 2, or 3;
or a salt thereof.

2. A compound of formula I:

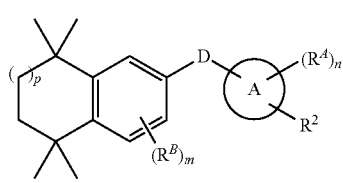

wherein:
p is 0 and D is

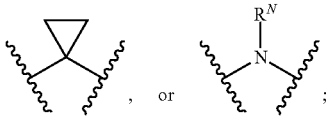, or ;

or p is 1 and D is

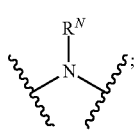;

$R^N$ is $(C_3-C_6)$cycloalkyl, or $(C_2-C_6)$alkynyl, wherein the $(C_3-C_6)$cycloalkyl, and $(C_2-C_6)$alkynyl are optionally substituted with one or more groups independently selected from halo, hydroxy, nitro, and cyano;
$R^2$ is —COOH, —B(OH)$_2$, or —SO$_3$H;
ring A is

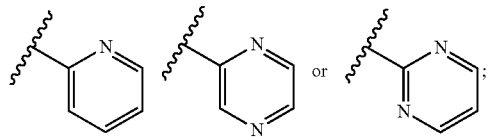;

each $R^A$ is independently selected from the group consisting of halo, hydroxy, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, wherein the $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy are optionally substituted with one or more groups independently selected from halo, hydroxy, nitro, cyano, $(C_1-C_6)$alkoxy, and oxo (=O);
each $R^B$ is independently selected from the group consisting of halo, hydroxy, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, wherein the $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy are optionally substituted with one or more groups independently selected from halo, hydroxy, nitro, cyano, $(C_1-C_6)$alkoxy, and oxo (=O);
n is 0, 1, 2, 3, or 4; and
m is 0, 1, 2, or 3;
or a salt thereof.

3. The compound of claim 2 that is selected from the group consisting of:

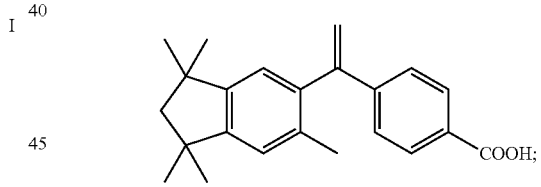

and salts thereof.

4. A compound selected from the group consisting of:

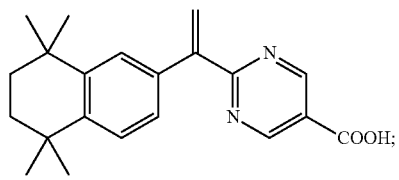 [SMILES: C=C(c1ccc2c(c1)C(C)(C)CCC2(C)C)c1ncc(C(=O)O)cn1]

and salts thereof.

5. A pharmaceutical composition comprising a compound as described in claim 2, or a pharmaceutically acceptable salt thereof, and a pharmaceutically acceptable diluent or carrier.

6. A method for inhibiting cancer cell growth comprising contacting the cell in vitro or in vivo with an effective amount of a compound as described in claim 2, or a salt thereof.

7. A method for treating cancer in a mammal having cancer comprising administering to the mammal an effective amount of compound as described in claim 2, or a pharmaceutically acceptable salt thereof.

8. The method of claim 7 wherein the cancer is glioblastoma multiforme, breast, lung, colon, pancreatic, skin, cutaneous T-cell lymphoma, acute promyelocytic leukemia, ovarian, bladder, kidney, head and neck cancers, or Kaposi's sarcoma.

9. A method for activating RXR in a cell comprising contacting the cell in vitro or in vivo with an effective amount of a compound as described in claim 2, or a salt thereof.

10. A method for treating Alzheimer's disease in a human having Alzheimer's disease comprising administering to the human an effective amount of compound as described in claim 2, or a pharmaceutically acceptable salt.

11. A method for treating multiple sclerosis, a disease associated with demyelination, in a human having multiple sclerosis comprising administering to the human an effective amount of compound as described in claim 2, or a pharmaceutically acceptable salt.

* * * * *